United States Patent
Cai et al.

(10) Patent No.: US 7,226,927 B2
(45) Date of Patent: Jun. 5, 2007

(54) SUBSTITUTED 2-ARYL-4-ARYLAMINOPYRIMIDINES AND ANALOGS AS ACTIVATORS OF CASPASES AND INDUCERS OF APOPTOSIS AND THE USE THEREOF

(75) Inventors: Sui Xiong Cai, San Diego, CA (US); John A Drewe, Carlsbad, CA (US); P. Sanjeeva Reddy, San Diego, CA (US); Bao Nguyen, San Diego, CA (US); Azra Pervin, San Marcos, CA (US)

(73) Assignee: Cytovia, Inc., San Diego, CA (US)

( * ) Notice: Subject to any disclaimer, the term of this patent is extended or adjusted under 35 U.S.C. 154(b) by 309 days.

(21) Appl. No.: 10/704,448

(22) Filed: Nov. 10, 2003

(65) Prior Publication Data

US 2004/0097503 A1    May 20, 2004

Related U.S. Application Data

(62) Division of application No. 10/012,444, filed on Dec. 12, 2001, now Pat. No. 6,716,851.

(60) Provisional application No. 60/254,581, filed on Dec. 12, 2000.

(51) Int. Cl.
   *A61K 31/53*    (2006.01)
   *A61K 31/505*   (2006.01)
   *A61K 31/506*   (2006.01)
   *C07D 239/02*   (2006.01)
   *C07D 409/00*   (2006.01)
   *C07D 251/00*   (2006.01)
   *C07C 49/00*    (2006.01)
   *C07C 255/17*   (2006.01)

(52) U.S. Cl. .................. 514/256; 514/241; 544/180; 544/326; 544/328

(58) Field of Classification Search .......... 514/241, 514/256; 544/180, 326, 328
   See application file for complete search history.

(56) References Cited

U.S. PATENT DOCUMENTS

| | | | | |
|---|---|---|---|---|
| 3,989,816 | A | 11/1976 | Rajadhyaksha | 424/60 |
| 4,041,030 | A | 8/1977 | Fauran et al. | 544/117 |
| 4,444,762 | A | 4/1984 | Rajadhyaksha | 514/24 |
| 5,250,530 | A | 10/1993 | Giencke et al. | 514/256 |
| 5,935,966 | A * | 8/1999 | Suto et al. | 514/275 |
| 6,103,737 | A | 8/2000 | Cocuzza et al. | 514/310 |
| 6,156,755 | A | 12/2000 | Geisen | 514/256 |
| 6,403,599 | B1 * | 6/2002 | Chen et al. | 514/269 |
| 6,610,677 | B2 * | 8/2003 | Davies et al. | 514/183 |
| 6,716,851 | B2 | 4/2004 | Cai et al. | 514/275 |
| 6,956,047 | B1 * | 10/2005 | Chen | 514/332 |

FOREIGN PATENT DOCUMENTS

| | | |
|---|---|---|
| EP | 0 407 899 A2 | 1/1991 |
| EP | 0 629 622 A1 | 12/1994 |
| EP | 0 640 599 A1 | 3/1995 |
| JP | 63-107966 | 5/1988 |
| WO | WO 95/06473 | 3/1995 |
| WO | 95-10506 * | 4/1995 |
| WO | WO 96/20721 | 7/1996 |
| WO | WO 97/09315 | 3/1997 |
| WO | WO 98/38171 | 9/1998 |
| WO | WO 99/18856 | 5/1999 |
| WO | WO 00/27824 | 5/2000 |
| WO | WO 01/25220 A1 | 4/2001 |
| WO | WO 01/27089 A1 | 4/2001 |
| WO | WO 02/47690 A1 | 6/2002 |

OTHER PUBLICATIONS

Cieplik, J. et. al., Chemical Abstract, vol. 120, Abstract # 298579.*
Batteux, F., et al., "Gene Therapy of Experimental Autoimmune Thyroiditis by In Vivo Administration of Plasmid DNA Coding for Fas Ligand," *J. Immunol.* 162:603-608, American Association of Immunologists (Jan. 1999).

(Continued)

*Primary Examiner*—James O. Wilson
*Assistant Examiner*—Tamthom N. Truong
(74) *Attorney, Agent, or Firm*—Sterne, Kessler, Goldstein & Fox P.L.L.C.

(57) ABSTRACT

The present invention is directed to substituted 2-aryl-4-arylaminopyrimidine and analogs thereof, represented by the general Formula I:

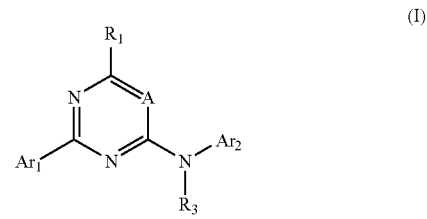

Figure 1A:
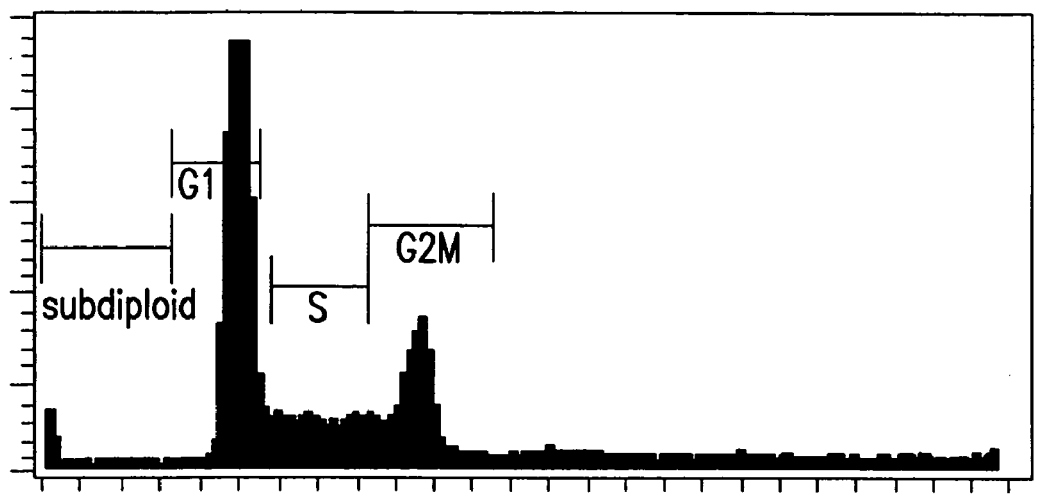

wherein A, $Ar_1$, $Ar_2$, $R_1$ and $R_3$ are defined herein. The present invention also relates to the discovery that compounds having Formula I are activators of caspases and inducers of apoptosis. The compounds of this invention may be used to induce cell death in a variety of clinical conditions in which uncontrolled growth and spread of abnormal cells occurs.

20 Claims, 2 Drawing Sheets

OTHER PUBLICATIONS

Boirivant, M., et al., "Lamina Propria T Cells in Crohn's Disease and Other Gastrointestinal Inflammation Show Defective CD2 Pathway-Induced Apoptosis," *Gastroent. 116*:557-565, American Gastroenterological Association (Mar. 1999).

Calabresi, P. and Chabner, B.A., "Section X. Chemotherapy of Neoplastic Diseases," in *Goodman & Gilman's The Pharmacological Basis of Therapeutics*, Wonsiewicz, M.J. and McCurdy, P., eds., McGraw-Hill Companies, Inc., New York, New York, pp. 1225-1287 (1996).

Coven, T.R., et al., "PUVA-induced lymphocyte apoptosis: Mechanism of action in psoriasis," *Photodermatol. Photoimmunol. Photomed. 15*:22-27, Munksgaard (Feb. 1999).

Ellis, R.E., et al., "Mechanisms and Functions of Cell Death," *Annu. Rev. Cell Biol. 7*:663-698, Annual Reviews, Inc. (1991).

Ellis, R.E. and Horvitz, H.R., "Two *C. elegans* genes control the programmed deaths of specific cells in the pharynx," *Develop. 112*:591-603, The Company of Biologists Ltd. (1991).

Friesen, C., et al., "Involvement of the CD95 (APO-1/Fas) receptor/ligand system in drug-induced apoptosis in leukemia cells," *Nature Med. 2*:574-577, Nature Publishing Group (1996).

Glücksmann, A., "Cell Deaths in Normal Vertebrate Ontogeny," *Biological Reviews Camb. Philos. Soc. 26*:59-86, The University Press (1951).

Glücksmann, A., "Cell death in normal development," *Arch. Biol. 76*:419-437, Vaillant-Carmanne (1965).

Greenwald, R.B., et al., "Drug Delivery Systems Employing 1,4- or 1,6-Elimination: Poly(ethylene glycol) Prodrugs of Amine-Containing Compounds," *J. Med. Chem. 42*:3657-3667, American Chemical Society (Aug. 1999).

Heenen, M., et al., "Methotrexate induces apoptotic cell death in human keratinocytes," *Arch. Dermatol. Res. 290*:240-245, Springer-Verlag (1998).

Infante, A.J., et al., "The clinical spectrum in a large kindred with autoimmune lymphoproliferative syndrome caused by a Fas mutation that impairs lymphocyte apoptosis," *J. Ped. 133*:629-633, Mosby, Inc. (1998).

Leu, Y.-L., et al., "Design and Synthesis of Water-Soluble Glucuronide Derivatives of Camptothecin for Cancer Prodrug Monotherapy and Antibody-Directed Enzyme Prodrug Therapy (ADEPT)," *J. Med. Chem. 42*:3623-3628, American Chemical Society (Aug. 1999).

López-Hoyos, M., et al., "Regulation of B cell apoptosis by Bcl-2 and Bcl-$X_L$ and its role in the development of autoimmune diseases (Review)," *Intl. J. Mol. Med. 1*:475-483, D.A. Spandidos (1998).

Los, M., et al., "Cross-Resistance of CD95- and Drug-Induced Apoptosis as a Consequence of Deficient Activation of Caspases (ICE/Ced-3 Proteases)," *Blood 90*:3118-3129, W.B. Saunders Company (1997).

Ohsako, S. and Elkon, K.B., "Apoptosis in the effector phase of autoimmune diabetes, multiple sclerosis and thyroiditis," *Cell Death Differ. 6*:13-21, Stockton Press (Jan. 1999).

O'Reilly, L.A. and Strasser, A., "Apoptosis and autoimmune disease," *Inflamm. Res. 48*:5-21, Birkhäuser Verlag (Jan. 1999).

Orrenius, S., "Apoptosis: molecular mechanisms and implications for human disease," *J. Int. Med. 237*:529-536, Blackwell Science Ltd. (1995).

Ozawa, M., et al., "312-nanometer Ultraviolet B Light (Narrow-Band UVB) Induces Apoptosis of T Cells within Psoriatic Lesions," *J. Exp. Med. 189*:711-718, The Rockefeller University Press (Feb. 1999).

Pettit, G.R. and Lippert III, J.W., "Antineoplastic agents 429. Syntheses of the combretastatin A-1 and combretastatin B-1 prodrugs," *Anti-Cancer Drug Des. 15*:203-216, Oxford University Press (Jun. 2000).

Reed, J.C., "Bcl-2 Family Proteins," in *Apoptosis and Cancer Chemotherapy*, Hickman, J.A. and Dive, C., eds., Humana Press, Totowa, NJ, pp. 99-116 (Apr. 1999).

Savill, J., "Apoptosis in resolution of inflammation," *J. Leuk. Biol. 61*:375-380, Society for Leukocyte Biology (1997).

Schmitt, E., et al., "The Bcl-xL and Bax-α control points: modulation of apoptosis induced by cancer chemotherapy and relation to TPCK-sensitive protease and caspase activation," *Biochem. Cell Biol. 75*:301-314, National Research Council of Canada (1997).

Thornberry, N.A., "The caspase family of cysteine proteases," *British Med. Bull. 53*:478-490, The Royal Society of Medicine Press Ltd. (1996).

Thornberry, N.A., "Caspases: key mediators of apoptosis," *Chem. & Biol. 5*:R97-R103, Current Biology, Ltd. (1998).

Vaishnaw, A.K., et al., "The molecular basis for apoptotic defects in patients with CD95 (Fas/Apo-1) mutations," *J. Clin. Invest. 103*:355-363, American Society for Clinical Investigation (Feb. 1999).

Vaux, D.L., et al., "An Evolutionary Perspective on Apoptosis," *Cell 76*:777-779, Cell Press (1994).

Wakisaka, S., et al., "Modulation by proinflammatory cytokines of Fas/Fas ligand-mediated apoptotic cell death of synovial cells in patients with rheumatoid arthritis (RA)," *Clin. Exp. Immunol. 114*:119-128, Blackwell Science (1998).

Wyllie, A.H., et al., "Cell Death: The Significance of Apoptosis," *Intl. Rev. Cyt. 68*:251-304, Academic Press (1980).

Wyllie, A.H., "Cell death: a new classification separating apoptosis from necrosis," in *Cell death in biology and pathology*, Bowen, I.D. and Lockshin, R.A., eds. Chapman and Hall, London, England, pp. 9-34 (1981).

Espace English language abstract of Japanese Patent Publication No. JP 63-107966 (Document AO2) available at http://v3.espacenet.com/textdoc?DB=EPODOC&IDX=JP63107966&F=0.

Supplementary Partial European Search Report for European Patent Application No. EP 01 99 0048.9, mailed May 6, 2005, European Patent Office, The Hague.

Zhou, T., et al., "Bisindolylmaleimide VIII facilitates Fas-mediated apoptosis and inhibits T cell-mediated autoimmune diseases," *Nature Med. 5*:42-48, Nature Publishing Group (Jan. 1999).

International Search Report for International Patent Application No. PCT/US01/47498, mailed May 30, 2002.

Dialog File 351, Accession No. 8512057, Derwent WPI English language abstract for EP 0 407 899 A2, published Jan. 16, 1991, Derwent Information Ltd, 2002 (3 pages).

\* cited by examiner

SUBSTITUTED 2-ARYL-4-ARYLAMINOPYRIMIDINES AND ANALOGS AS ACTIVATORS OF CASPASES AND INDUCERS OF APOPTOSIS AND THE USE THEREOF

This is a divisional of U.S. Ser. No. 10/012,444 filed Dec. 12, 2001, now U.S. Pat. No. 6,716,851 which claims the benefit of U.S. Provisional Application No. 60/254,581 filed Dec. 12, 2000.

BACKGROUND OF THE INVENTION

1. Field of the Invention

This invention is in the field of medicinal chemistry. In particular, the invention relates to substituted 2-aryl-4-arylaminopyrimidines and analogs, and the discovery that these compounds are activators of caspases and inducers of apoptosis. The invention also relates to the use of these compounds as therapeutically effective anti-cancer agents.

2. Related Art

Organisms eliminate unwanted cells by a process variously known as regulated cell death, programmed cell death or apoptosis. Such cell death occurs as a normal aspect of animal development as well as in tissue homeostasis and aging (Glucksmann, A., Biol. Rev. Cambridge Philos. Soc. 26:59–86 (1951); Glucksmann, A., Archives de Biologie 76:419–437 (1965); Ellis, et al., Dev. 112:591–603 (1991); Vaux, et al., Cell 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., J. Internal Medicine 237:529–536 (1995)).

Apoptosis is achieved through an endogenous mechanism of cellular suicide (Wyllie, A. H., in Cell Death in Biology and Pathology, Bowen and Lockshin, eds., Chapman and Hall (1981), pp. 9–34). A cell activates its internally encoded suicide program as a result of either internal or external signals. The suicide program is executed through the activation of a carefully regulated genetic program (Wyllie, et al., Int. Rev. Cyt. 68:251 (1980); Ellis, et al., Ann. Rev. Cell Bio. 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., J. Internal Medicine 237:529–536 (1995)).

It has been found that a group of proteases are a key element in apoptosis (see, e.g., Thornberry, Chemistry and Biology 5:R97–R103 (1998); Thornberry, British Med. Bull. 53:478–490 (1996)). Genetic studies in the nematode Caenorhabditis elegans revealed that apoptotic cell death involves at least 14 genes, two of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (Apoptosis and Cancer Chemotherapy, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., Biochem. Cell. Biol. 75:301–314 (1997)). BCL-like proteins include BCL-XL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., Blood 90:3118–3129 (1997); Friesen, et al., Nat. Med. 2:574 (1996)). The mechanism of action of current antineoplastic drugs frequently involves an attack at specific phases of the cell cycle. In brief, the cell cycle refers to the stages through which cells normally progress during their lifetimes. Normally, cells exist in a resting phase termed $G_o$. During multiplication, cells progress to a stage in which DNA synthesis occurs, termed S. Later, cell division, or mitosis occurs, in a phase called M. Antineoplastic drugs such as cytosine arabinoside, hydroxyurea, 6-mercaptopurine, and methotrexate are S phase specific, whereas antineoplastic drugs such as vincristine, vinblastine, and paclitaxel are M phase specific. Many slow growing tumors, for example colon cancers, exist primarily in the $G_o$ phase, whereas rapidly proliferating normal tissues, for example bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (See, e.g., Hardman, et al., eds., Goodman and Gilman's The Pharmacological Basis of Therapeutics, Ninth Edition, McGraw-Hill, New York (1996), pp. 1225–1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

Eur. Pat. Appl. EP 407899 discloses aminopyrimidine derivatives with activity as fungicide:

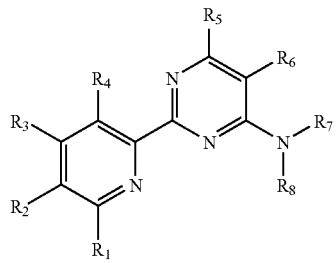

wherein, $R_1$ is H, alkyl, alkoxyalkyl, alkylthioalkyl, cycloalkyl, alkenyl, alkynyl, cycloalkyalkyl, substituted aminoalkyl, phenyl, phenylalkyl, phenoxyalkyl, phenylmercaptoalkyl or phenoxyphenoxyalkyl, wherein the phenyl-portions are optionally substituted;

$R_2$, $R_3$, $R_4$ independently are H, alkyl or optionally substituted phenyl;

$R_5$ is H, alkyl, cycloalkyl, cycloalkylalkyl, haloalkyl, alkoxy, alkylthio, alkoxyalkyl, $R_7R_8N-$, alkylthioalkyl, $R_7R_8$-alkyl, halogen, alkenyl, alkynyl, phenyl, phenoxy, phenylalkyl, phenoxyalkyl, phenylmercaptoalkyl, phenylmercapto, phenylalkoxy or phenylalkylthio, wherein the phenyl-portions are optionally substituted;

$R_6$ is H, alkyl, alkoxy, alkenyloxy, alkynyloxy, alkylthio, halogen or optionally substituted phenyl; or $R_5$ and $R_6$ are taken together to form a polymethylene group;

$R_7$ and $R_8$ independently are H, alkyl, alkoxyalkyl, hydroxyalkyl, alkylthioalkyl, alkenyl, substituted aminoalkyl, alkynyl, cycloalkyl, cycloalkylalkyl, which in the cycloalkyl-portion is optionally substituted, formyl, phenyl or phenylalkyl, which in the phenyl-portion is optionally substituted; or $R_7$ and $R_8$ are taken together with the nitrogen atom to which they are attached to form an optionally substituted 5- to 7-member, saturated or unsaturated, heterocycle with 1 or 3 heteroatoms, which are the same or different; and the acid addition salts which are functional as fungicides.

WO 0127089 patent application discloses pyrimidine derivatives for the treatment of diseases or medical conditions mediated by cytokines:

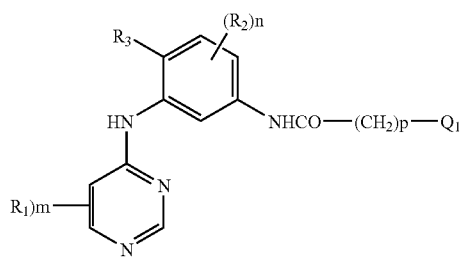

wherein, m is 0, 1, 2 or 3 are each $R^1$ group, which may be the same or different, is selected from hydroxy, halogeno, trifluoromethyl, cyano, mercapto, nitro, amino, carboxy, carbamoyl, formyl, sulphamoyl, (1–6C)alkyl, (1–6C)alkoxy, (1–6C)alkylthio, (1–6C)alkylsulphinyl, (1–6C)alkylsulphonyl, (1–6C)alkylamino, di[(1–6C)alkyl]amino, (1–6C)alkylsulphonyl, N-(1–6C)alkycarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$$Q^2-X^1-$$

wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)$, $N(R^4)SO_2$, $OC(R^4)_2$, $SC(R^4)_2$ and $N(R^4)C(R^4)_2$, wherein each $R^4$ is hydrogen or (1–6C)alkyl, and $Q^2$ is aryl-(1–6C)alkyl, heteroaryl-(1–6C)alkyl, heterocyclyl or heterocyclyl-(1–6C)alkyl, or $(R^1)_m$ is (1–3C)alkylenedioxy, and wherein any aryl, heteroaryl or heterocyclyl group within a substituted on $R^1$ optionally bears 1, 2 or 3 substituents, $R_3$ is hydrogen, halogeno or (1–6C)alkyl;

n is 0, 1 or 2 and each $R^2$ group, which may be the same or different is selected from hydroxy, halogeno, trifluoromethyl, cyano, mercapto, nitro, amino, carboxy, (1–6C)alkoxycarbonyl, (1–6C)alkyl, (1–6C)alkoxy, (1–6C)alkylamino and di[(1–6C)alkyl]amino;

p is 0, 1, 2, 3, or 4; and $Q^1$ is aryl or heteroaryl and $Q^1$ is optionally substituted with 1, 2, or 3 substituents, which may be the same of different, selected from hydroxy, halogeno, trifluoromethyl, cyano, mercapto, nitro, amino, carboxy, carbamoyl, formyl, (1–6C)alkyl, (1–6C)alkoxy, (1–6C)alkylthio, (1–6C)alkylsulphinyl, (1–6C)alkylsulphonyl, (1–6C)alkylamino, di[(1–6C)alkyl]amino, (1–6C)alkoxycarbonyl, N-(1–6C)alkycarbamoyl, N,N-di-[(1–6C)alkyl]carbamoyl, (2–6C)alkanoyl, (2–6C)alkanoyloxy, (2–6C)alkanoylamino, N-(2–6C)alkyl-(2–6C)alkanoylamino, N-(2–6C)alkylsulphamoyl, N,N-di-[(1–6C)alkyl]sulphamoyl, (1–6C)alkanesulphonylamino and N-(1–6C)alkyl-(1–6C)alkanesulphonylamino, or with a (1–3C)alkylenedioxy group, or from a group of the formula:

$$-X^3-Q^4$$

wherein $X^3$ is a direct a bond or is selected from O and $N(R^8)$, Wherein $R^8$ is hydrogen or (1–6C)alkyl, and $Q^4$ is aryl, aryl-(1–6C)alkyl, heteroaryl, heteroaryl-(1–6C)-alkyl, heterocyclyl or heterocyclyl(1–6C)alkyl, and any $Q^4$ group optionally bears 1 or 2 substituents, which may be the same of different, selected from halogeno, trifluoromethyl, cyano, hydroxy, amino, (1–6C)alkyl, (1–6C)alkoxy, (1–6C)alkylamino and di-[(1–6C)alkyl]amino.

WO 0027824 patent application discloses substituted pyrimidine compositions and methods of use. The compounds are said to have activity as inhibitors of phospholipase $A_2$, and are useful in treating disorders mediated by phospholipase $A_2$:

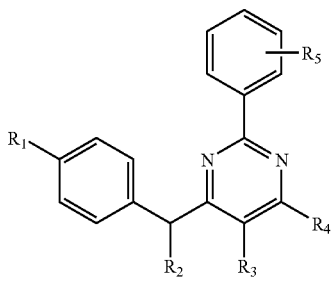

wherein,
the symbol $R_1$ represents a $C_1$–$C_6$ alkyl, $C_1$–$C_6$ alkoxy or halogen atom. The symbol $R_2$ represents a phenyl group, substituted phenyl group, benzyl moiety, substituted benzyl moiety, $C_3$–$C_7$ cycloalkyl, or substituted $C_3$–$C_7$ cycloalkyl. The symbol $R_3$ represents a hydrogen or $C_1$–$C_6$ alkyl group. The symbol $R_4$ represents —H, —OH, —$N_3$ or —NHCOCH$_3$. The symbol $R_5$ represents H or alkyl, preferably H.

U.S. Pat. No. 6,156,755 discloses the use of pyridine derivatives for the prevention of cancer:

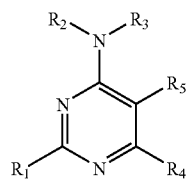

wherein,
$R^1$ is hydrogen, halogen, cyano, nitro, trifluoromethyl, amino, ($C_1$–$C_6$)-alkyl, ($C_1$–$C_6$)-hydroxyalkyl, ($C_1$–$C_6$)-alkoxy, ($C_6$–$C_{12}$)-aryl, ($C_1$–$C_6$)-alkoxycarbonyl-($C_1$–$C_6$)-alkyl, ($C_1$–$C_6$)-alkyl-S—($C_1$–$C_6$)-alkyl, ($C_1$–$C_6$)-alkyl-SO—($C_1$–$C_6$)-alkyl, ($C_1$–$C_6$)-alkyl-SO$_2$—($C_1$–$C_6$)-alkyl, dihydroxy-($C_1$–$C_6$)-alkyl, aryl, heteroaryl, heteroaryl-($C_1$–$C_6$)-alkyl, aryl-($C_1$–$C_6$)-alkyl, ($C_1$–$C_6$)-alkoxycarbonylaryl, aryl-($C_1$–$C_6$)-alkyloxy or heteroaryl-($C_1$–$C_6$)-alkyloxy, heteroaryl is pyridyl, furyl, tetrahydrofuryl, thienyl, imidazolyl, pyrazolyl, triazolyl, thiazolyl, oxazolyl, benzothiazolyl;

$R^2$, $R^3$ independently of one another are hydrogen, ($C_1$–$C_6$)-alkyl, ($C_6$–$C_{12}$)aryl, ($C_6$–$C_{12}$)-arylalkyl having 1–4 alkyl carbon atoms, where aryl can be substituted by one to three substituents selected from the group consisting of chlorine, bromine, trifluoromethyl, ($C_1$–$C_6$)-alkyl, ($C_1$–$C_6$)-alkoxy, or $R^2$, $R^3$, together with the nitrogen to which they are bonded, form the azetidino, pyrrolidino, piperidino, piperazino or morpholino group, where the heterocycles can be substituted by one or two substituents selected from the group consisting of chlorine, bromine, trifluoromethyl, ($C_1$–$C_6$)-alkyl, ($C_1$–$C_6$)-alkoxy, —S—($C_1$–$C_6$)-alkyl, —SO—($C_1$–$C_6$)-alkyl, —SO$_2$—($C_1$–$C_6$)-alkyl, sulfamoyl, N—($C_1$–$C_4$)-alkylsulfamoyl, N,N—($C_1$–$C_4$)-dialkylsulfamoyl, ($C_1$–$C_6$)-alkoxycarbonyl, N,N—($C_1$–$C_4$)-dialkylcarbamoyl, N—($C_1$–$C_4$)-alkylcarbamoyl, N—($C_6$–$C_{12}$)-arylcarbamoyl, ($C_6$–$C_{12}$)-arylcarbamoyl substituted in the aryl radical by ($C_1$–$C_4$)-alkyl, ($C_1$–$C_4$)-alkoxyl, halogen, NO$_2$, NH$_2$, CN or CF$_3$, ($C_6$–$C_{12}$)-arylcarbonyl substituted in the aryl radical by ($C_1$–$C_4$)-alkoxy, halogen, NO$_2$, NH$_2$, CN or CF$_3$, ($C_1$–$C_6$)-alkylsulfonyl, ($C_1$–$C_6$)-alkylsulfinyl, ($C_6$–$C_{12}$)-arylsulfonyl, ($C_6$–$C_{12}$)-arylsulfonyl substituted in the aryl radical by ($C_1$–$C_4$)-alkyl, ($C_1$–$C_4$)-alkoxy, halogen, NO$_2$, NH$_2$, CN or CF$_3$, heteroarylcarbonyl or heteroarylsulfonyl;

$R^4$ and $R^5$ independently of one another are hydrogen, halogen, cyano, nitro, trifluoromethyl, amino, ($C_1$–$C_6$)-alkyl, ($C_1$–$C_6$)-hydroxyalkyl, ($C_1$–$C_6$)-alkoxy, ($C_6$–$C_{12}$)-aryl, naphthyl, furyl, where ($C_6$–$C_{12}$)-aryl, naphthyl and furyl can be substituted by one or two substituents selected from the group consisting of chlorine, bromine, trifluoromethyl, ($C_1$–$C_6$)-alkyl, ($C_1$–$C_6$)-alkoxy, —S—($C_1$–$C_6$)-alkyl, —SO—($C_1$–$C_6$)-alkyl, —SO$_2$—($C_1$–$C_6$)-alkyl, hydroxyl; and their physiologically tolerable salts.

SUMMARY OF THE INVENTION

The present invention is related to the discovery that substituted 2-aryl-4-arylaminopyrimidines and analogs, as represented in Formula I, are activators of the caspase cascade and inducers of apoptosis. Thus, an aspect of the present invention is directed to the use of compounds of Formula I as inducers of apoptosis.

Compounds of the present invention are represented by Formula I:

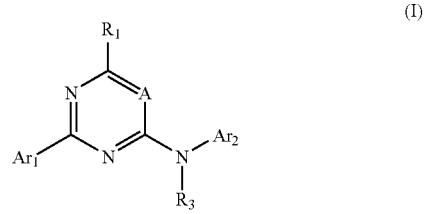

or pharmaceutically acceptable salts or prodrugs thereof, wherein:

Ar$_1$ and Ar$_2$ are independently and optionally substituted aryl or heteroaryl;

A is N or C—R$_2$;

R$_1$ and R$_2$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, aryloxy, arylalkoxy, haloalkoxy, carboxy, carbonylamido or alkylthiol; and R$_3$ is hydrogen, an optionally substituted alkyl or cycloalkyl.

A second aspect of the present invention is to provide a method for treating, preventing or ameliorating neoplasia and cancer by administering a compound of Formula I to a mammal in need of such treatment.

Many of the compounds within the scope of the present invention are novel compounds. Therefore, a third aspect of the present invention is to provide novel compounds of Formula I, and to also provide for the use of these novel compounds for treating, preventing or ameliorating neoplasia and cancer.

A fourth aspect of the present invention is to provide a pharmaceutical composition useful for treating disorders responsive to the induction of apoptosis, containing an effective amount of a compound of Formula I in admixture with one or more pharmaceutically acceptable carriers or diluents.

A fifth aspect of the present invention is directed to methods for the preparation of novel compounds of Formula I.

BRIEF DESCRIPTION OF THE DRAWINGS/FIGURES

Figure 1B:
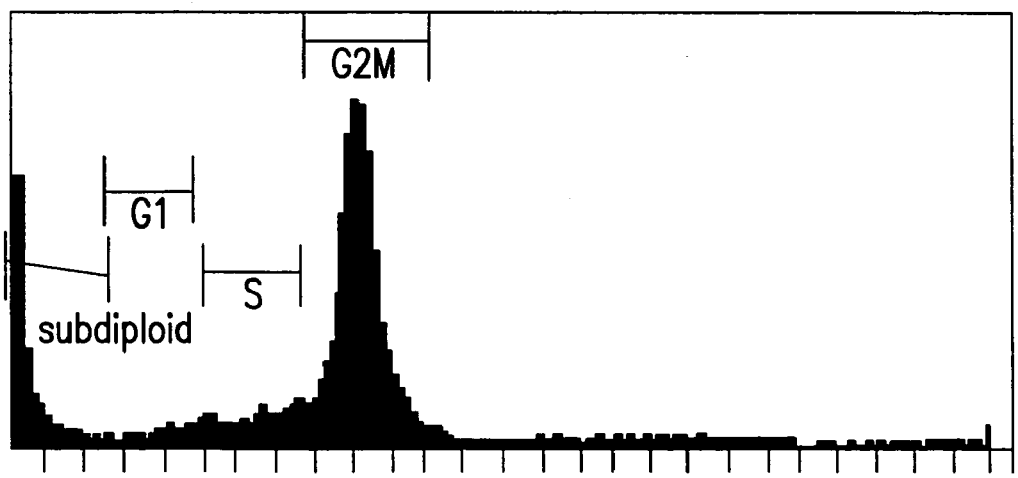

FIGS. 1A–B are graphs showing drug induced cell cycle arrest and apoptosis in T47D cells. FIG. 1A: control cells showing most of the cells in G1 phase of the cell cycle (M2). FIG. 1B: cells treated with 200 nM of 4-(3-methoxyanilino)-2-(2-pyridinyl)-6-(trifluoromethyl)pyrimidine for 48 h showing a reduction in the G1 population (M2), an increase in the G2/M population (M4) and the sub-diploid DNA population of cells (M1).

Figure 2:
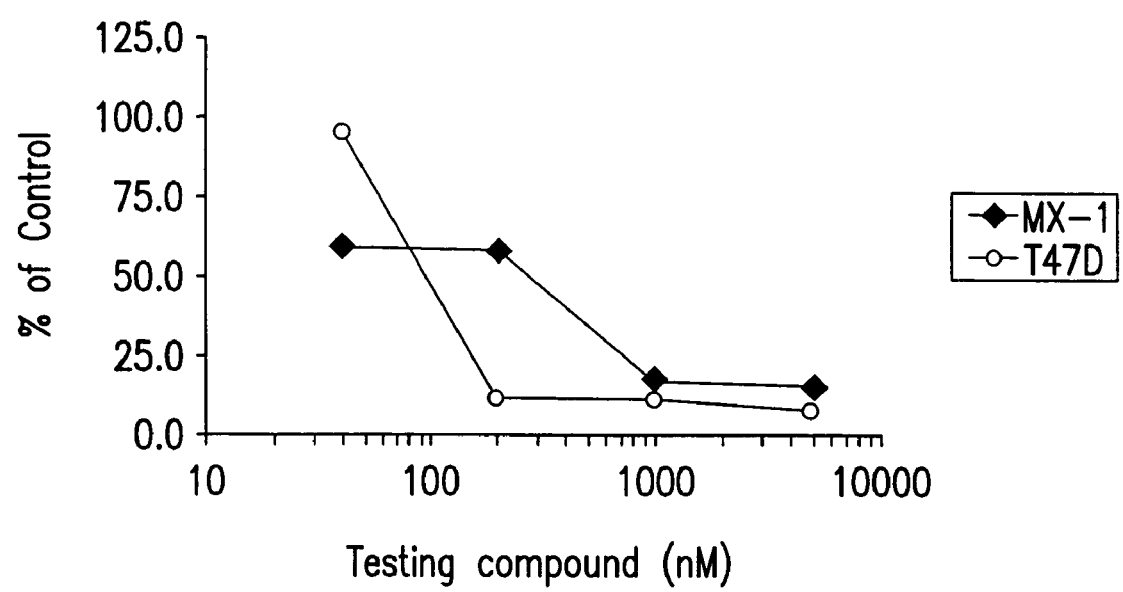

FIG. 2 is a graph showing inhibition of clonogenic survival of MX-1 and T47D cells treated for 48 h with different concentrations of 4-(3-methoxyanilino)-2-(2-pyridinyl)-6-(trifluoromethyl)pyrimidine. FIG. 2 shows increasing inhibition of clonogenicity with increasing drug concentration, with IC50 of about 100 nM and 300 nM for T47D and MX-1 cells, respectively.

DETAILED DESCRIPTION OF THE INVENTION

The present invention arises out of the discovery that substituted 2-aryl-4-arylaminopyrimidines and analogs, as represented in Formula I, are potent and highly efficacious activators of the caspase cascade and inducers of apoptosis. Therefore compounds of Formula I are useful for treating disorders responsive to induction of apoptosis.

Specifically, compounds of the present invention are represented by Formula I:

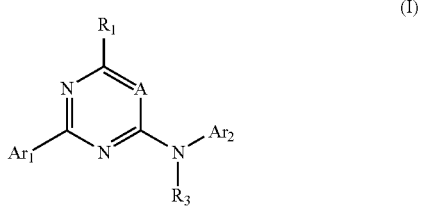

or pharmaceutically acceptable salts or prodrugs thereof, wherein:
$Ar_1$ and $Ar_2$ are independently and optionally substituted aryl or heteroaryl;
A is N or C—$R_2$;
$R_1$ and $R_2$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, aryloxy, arylalkoxy, haloalkoxy, carboxy, carbonylamido or alkylthiol; and
$R_3$ is hydrogen, an optionally substituted alkyl or cycloalkyl.

Preferred compounds of Formula I include compounds wherein $Ar_1$ or $Ar_2$ is optionally substituted phenyl, naphthyl, pyridinyl, pyrimidinyl, pyrazinyl, indolyl, quinolyl, isoquinolyl, thienyl, furyl, or pyrrolyl. Preferred compounds of Formula I also include compounds wherein $R_3$ is hydrogen. Preferred compounds of Formula I also include compounds wherein A is C—$R_2$. Especially preferred compounds of Formula I include compounds wherein $Ar_1$ is optionally substituted pyridinyl, pyrimidinyl and pyrazinyl. Especially preferred compounds of Formula I also include compounds wherein $Ar_2$ is optionally substituted phenyl, pyridinyl, pyrimidinyl, pyrazinyl and indolyl.

Preferred structures of Formula I are substituted 2-aryl-4-arylaminopyrimidines and analogs represented by Formula II:

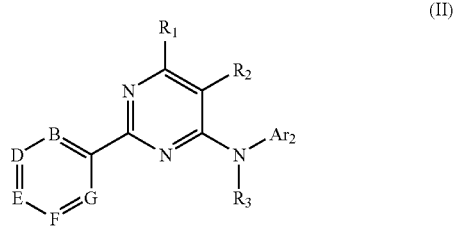

or pharmaceutically acceptable salts or prodrugs thereof, wherein $R_1$–$R_3$, and $Ar_2$ are as defined in Formula I;
B is N or C—$R_4$;
D is N or C—$R_5$;
E is N or C—$R_6$;
F is N or C—$R_7$;
G is N or C—$R_8$; and
$R_4$–$R_8$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, aryloxy, arylalkoxy, haloalkoxy, carboxy, carbonylamido or alkylthiol;

provided that not more than three of B, D, E, F and G are N.

Preferred compounds falling within the scope of Formula II include compounds wherein $R_1$ is an optionally substituted alkyl, haloalkyl or phenyl. Preferred compounds of Formula II also include compounds wherein $Ar_2$ is an optionally substituted phenyl, pyridinyl, pyrimidinyl, pyrazinyl and indolyl. Preferred compounds of Formula II also include compounds wherein B is nitrogen, D is C—$R_5$, E is C—$R_6$, F is C—$R_7$, and G is C—$R_9$. Preferred compounds of Formula II also include compounds wherein D is nitrogen, B is C—$R_4$, E is C—$R_6$, F is C—$R_7$, and G is C—$R_9$. Preferred compounds of Formula II also include compounds wherein E is nitrogen, D is C—$R_5$, B is C—$R_4$, F is C—$R_7$, and G is C—$R_8$. Preferred compounds of Formula II also include compounds wherein two of B, D, E, F and G are N.

Preferred structures of Formula I are substituted 2-aryl-4-arylaminopyrimidines and analogs represented by Formula III:

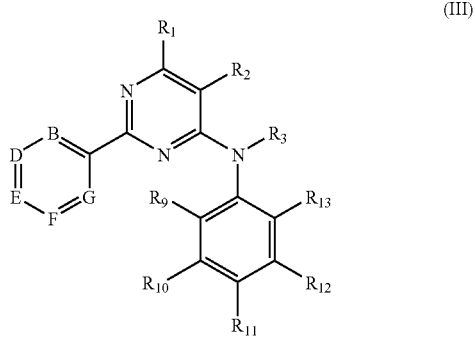

or pharmaceutically acceptable salts or prodrugs thereof, wherein $R_1$–$R_3$, and B, D, E, F and G are as defined in Formula I and II;

$R_9$–$R_{13}$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, aryloxy, arylalkoxy, haloalkoxy, carboxy, carbonylamido or alkylthiol.

Preferred compounds falling within the scope of Formula III include compounds wherein $R_1$ is an optionally substituted alkyl, haloalkyl. Preferred compounds of Formula III also include compounds wherein $R_2$ is hydrogen. Preferred compounds of Formula III also include compounds wherein one of the B, D, E, F and G is nitrogen. Preferred compounds of Formula III also include compounds wherein two of the B, D, E, F and G is nitrogen. Preferred compounds of Formula III also include compounds wherein $R_{10}$ or $R_{12}$ are not hydrogen. Preferred compounds of Formula III also include compounds wherein $R_9$ and $R_{12}$ are not hydrogen. Preferred compounds of Formula III also include compounds wherein $R_{10}$ and $R_{12}$ are not hydrogen. Preferred compounds of Formula III also include compounds wherein $R_9$, $R_{11}$ and $R_{12}$ are not hydrogen.

Exemplary preferred compounds that may be employed in the method of the invention include, without limitation:

4-(3-Methoxyanilino)-2-(2-pyridinyl)-6-(trifluoromethyl)pyrimidine;
4-(2-Fluoroanilino)-2-(4-pyridinyl)-6-(trifluoromethyl)pyrimidine;
4-(4-Methoxyanilino)-2-(4-pyridinyl)-6-(trifluoromethyl)pyrimidine;
4-(4-Methoxyanilino)-2-(2-pyridinyl)-6-(trifluoromethyl)pyrimidine;
4-(3,5-Dichloroanilino)-2-(4-pyridinyl)-6-(trifluoromethyl)pyrimidine;
4-(2,4-Difluoroanilino)-2-(4-pyridinyl)-6-(trifluoromethyl)pyrimidine;
4-(2-Methylanilino)-2-phenyl-6-methylpyrimidine;
4-(4-Methoxyanilino)-2-(2-hydroxyphenyl)-6-methylpyrimidine;
4-(4-(Trifluoromethoxy)anilino)-2-(pyridinyl)-6-(trifluoromethyl)pyrimidine;
4-(3-Fluoroanilino)-2-(2-pyridinyl)-6-(trifluoromethyl)pyrimidine;
4-(3,5-Dichloroanilino)-2-(2-pyridinyl)-6-(trifluoromethyl)pyrimidine;
4-(2-Fluoroanilino)-2-(2-pyridinyl)-6-(trifluoromethyl)pyrimidine;
4-(3-(Trifluoromethyl)anilino)-2-(2-pyridinyl)-6-(trifluoromethyl)pyrimidine;
4-(4-(Trifluoromethyl)anilino)-2-(2-pyridinyl)-6-(trifluoromethyl)pyrimidine;
4-(4-Fluoroanilino)-2-(2-pyridinyl)-6-(trifluoromethyl)pyrimidine;
4-(2,4-Dichloroanilino)-2-(2-pyridinyl)-6-(trifluoromethyl)pyrimidine;
4-(3-Chloroanilino)-2-(2-pyridinyl)-6-(trifluoromethyl)pyrimidine;
4-(3,4-Dichloroanilino)-2-(2-pyridinyl)-6-(trifluoromethyl)pyrimidine;
4-(4-Chloroanilino)-2-(2-pyridinyl)-6-(trifluoromethyl)pyrimidine;
4-(4-Fluoroanilino)-2-(3-pyridinyl)-6-(trifluoromethyl)pyrimidine;
4-(4-Methoxyanilino)-2-(3-pyridinyl)-6-(trifluoromethyl)pyrimidine;
4-(2-Fluoroanilino)-2-(3-pyridinyl)-6-(trifluoromethyl)pyrimidine;
4-(3-(Trifluoromethyl)anilino)-2-(3-pyridinyl)-6-(trifluoromethyl)pyrimidine;
4-(3-Chloroanilino)-2-(3-pyridinyl)-6-(trifluoromethyl)pyrimidine;
4-(4-Chloroanilino)-2-(2-pyridinyl)-6-(methoxymethyl)pyrimidine;
4-(4-Methoxyanilino)-2-(2-pyridinyl)-6-(methoxymethyl)pyrimidine;
4-(3-Chloroanilino)-2-(2-pyridinyl)-6-(methoxymethyl)pyrimidine;
4-(4-(Trifluoromethoxy)anilino)-2-(2-pyridinyl)-6-t-butylpyrimidine;
4-(4-Methoxyanilino)-2-(2-pyridinyl)-6-t-butylpyrimidine;
4-(3-Methoxyanilino)-2-phenyl-6-chloropyrimidine;
4-(4-Methoxyanilino)-2-phenyl-6-chloropyrimidine;
4-(3-Methoxyanilino)-6-methyl-2-(2-pyridinyl)pyrimidine;
4-(4-Methoxyanilino)-6-methyl-2-(2-pyridinyl)pyrimidine;
4-(3-Fluoroanilino)-6-methyl-2-(2-pyridinyl)pyrimidine;
4-(3-Methylanilino)-6-methyl-2-(2-pyridinyl)pyrimidine;
4-(3,4,5-Trimethoxyanilino)-2-(N-pyrrolyl)-1,3,5-triazine;
4-(3,5-Dichloroanilino)-2-(N-pyrrolyl)-1,3,5-triazine;
4-[2-(Trifluoromethyl)benzylamino]-2-(2-pyridinyl)-6-(trifluoromethyl)pyrimidine;
4-(4-Methoxyanilino)-2-(3-methylphenyl)-6-(methoxymethyl)pyrimidine;
4-(2-Chloroanilino)-2-(N-pyrrolyl)-1,3,5-triazine;
4-(2,5-Dimethoxyanilino)-6-methyl-2-(2-pyridinyl)pyrimidine;
4-(3-Dimethylaminoanilino)-6-methyl-2-(2-pyridinyl)pyrimidine;
4-(3-Isopropylanilino)-6-methyl-2-(2-pyridinyl)pyrimidine;
4-(2,5-Dimethoxyanilino)-2-(3-pyridinyl)-6-(trifluoromethyl)pyrimidine;
4-(2,5-Dimethoxyanilino)-6-(methoxymethyl)-2-(3-methylphenyl)pyrimidine;
4-(3-Methoxyanilino)-2-(4-pyridinyl)-6-(trifluoromethyl)pyrimidine;
4-(2,5-Dimethoxyanilino)-2-(4-pyridinyl)-6-(trifluoromethyl)pyrimidine;
4-(3-Methoxyanilino)-6-(methoxymethyl)-2-(2-methyl-1-3-thiazol-4-yl)pyrimidine;
4-(2,5-Dimethoxyanilino)-6-(methoxymethyl)-2-(2-methyl-1-3-thiazol-4-yl)pyrimidine;
4-(2-Chloro-5-methoxyanilino)-6-(methoxymethyl)-2-(2-methyl-1,3-thiazol-4-yl)pyrimidine;
4-(5-Methoxy-2-methylanilino)-6-(methoxymethyl)-2-(2-methyl-1,3-thiazol-4-yl)pyrimidine;
4-(2-Chloro-5-methoxyanilino)-2-(3-pyridinyl)-6-(trifluoromethyl)pyrimidine;
4-(5-Methoxy-2-methylanilino)-2-(3-pyridinyl)-6-(trifluoromethyl)pyrimidine;
4-(2-Chloro-5-methoxyanilino)-6-methyl-2-(2-pyridinyl)pyrimidine;
4-(5-Methoxy-2-methylanilino)-6-methyl-2-(2-pyridinyl)pyrimidine;
4-(2-Chloro-5-methoxyanilino)-2-(4-pyridinyl)-6-(trifluoromethyl)pyrimidine;

4-(5-Methoxy-2-methylanilino)-2-(4-pyridinyl)-6-(trifluoromethyl)pyrimidine;
4-(2-Chloro-5-methoxyanilino)-6-(methoxymethyl)-2-(3-methylphenyl)pyrimidine;
4-(5-Methoxy-2-methylanilino)-6-(methoxymethyl)-2-(3-methylphenyl)pyrimidine;
4-(2,5-Dimethoxyanilino)-2-(2-pyridinyl)-6-(trifluoromethyl)pyrimidine;
4-(2,5-Dimethylanilino)-2-(3-pyridinyl)-6-(trifluoromethyl)pyrimidine;
4-(3-Hydroxyanilino)-2-(2-pyridinyl)-6-(trifluoromethyl)pyrimidine hydrochloride;
4-(3,4-Methylenedioxyanilino)-2-(2-pyridinyl)-6-(trifluoromethyl)pyrimidine;
4-(3,4-Methylenedioxyanilino)-2-(4-pyridinyl)-6-(trifluoromethyl)pyrimidine;
4-(3,4-Methylenedioxyanilino)-2-(3-pyridinyl)-6-(trifluoromethyl)pyrimidine;
4-(3-Methoxyanilino)-2-phenyl-6-(trifluoromethyl)pyrimidine;
4-(3-Methoxyanilino)-2-(2-pyrazinyl)-6-(trifluoromethyl)pyrimidine;
4-(2,5-Dimethoxyanilino)-2-phenyl-6-(trifluoromethyl)pyrimidine;
4-(2,5-Dimethoxyanilino)-2-(2-pyrazinyl)-6-(trifluoromethyl)pyrimidine;
4-(3,4-Dimethoxyanilino)-2-phenyl-6-(trifluoromethyl)pyrimidine;
4-(3,4-Dimethoxyanilino)-2-(2-pyrazinyl)-6-(trifluoromethyl)pyrimidine;
4-(5-Methoxy-2-methylanilino)-2-phenyl-6-(trifluoromethyl)pyrimidine;
4-(5-Methoxy-2-methylanilino)-2-(2-pyrazinyl)-6-(trifluoromethyl)pyrimidine;
4-(2-Chloro-5-methoxyanilino)-2-phenyl-6-(trifluoromethyl)pyrimidine;
4-(2-Chloro-5-methoxyanilino)-2-(2-pyrazinyl)-6-(trifluoromethyl)pyrimidine;
4-(3,4-Methylenedioxyanilino)-2-(2-pyrazinyl)-6-(trifluoromethyl)pyrimidine;
4-(2-Methoxy-5-phenoxyanilino)-2-(3-pyridinyl)-6-(trifluoromethyl)pyrimidine
4-[2-Methyl-5-(carboxymethylester)anilino]-2-(3-pyridinyl)-6-(trifluoromethyl)pyrimidine;
4-(2-Methoxy-5-methylanilino)-2-(3-pyridinyl)-6-(trifluoromethyl)pyrimidine;
4-(5-Fluoro-2-methylanilino)-2-(3-pyridinyl)-6-(trifluoromethyl)pyrimidine;
4-(2-Methoxy-5-trifluoromethylanilino)-2-(3-pyridinyl)-6-(trifluoromethyl)pyrimidine;
4-(2-Methyl-5-nitroanilino)-2-(3-pyridinyl)-6-(trifluoromethyl)pyrimidine;
4-(5-Amino-2-methylanilino)-2-(3-pyridinyl)-6-(trifluoromethyl)pyrimidine hydrochloride;
4-(3-Ethoxyanilino)-2-(2-pyridinyl)-6-(trifluoromethyl)pyrimidine;
4-(3-Ethylanilino)-2-(2-pyridinyl)-6-(trifluoromethyl)pyrimidine;
4-(5-Methoxy-2-methylanilino)-2-(2-pyridinyl)-6-(trifluoromethyl)pyrimidine;
4-(2-Chloro-5-methoxyanilino)-2-(2-pyridinyl)-6-(trifluoromethyl)pyrimidine;
4-(3-Methylmercaptoanilino)-2-(2-pyridinyl)-6-(trifluoromethyl)pyrimidine;
4-(3-Hydroxyanilino)-2-(3-pyridinyl)-6-(trifluoromethyl)pyrimidine hydrochloride;
4-(3-Hydroxyanilino)-2-(2-pyrazinyl)-6-(trifluoromethyl)pyrimidine hydrochloride;
4-(3-Hydroxyanilino)-2-(4-pyridinyl)-6-(trifluoromethyl)pyrimidine hydrochloride;
4-(2,4-Dimethoxyanilino)-6-methyl-2-(2-pyridinyl)-pyrimidine hydrochloride;
4-(3,5-Dimethoxyanilino)-6-methyl-2-(2-pyridinyl)-pyrimidine hydrochloride;
4-(2,5-Diethoxyanilino)-2-(3-pyridinyl)-6-(trifluoromethyl)pyrimidine;
4-(5-Carboxyl-2-methoxyanilino)-2-(3-pyridinyl)-6-(trifluoromethyl)pyrimidine hydrochloride;
4-(2-Chloro-5-hydroxyanilino)-2-(3-pyridinyl)-6-(trifluoromethyl)pyrimidine;
4-(2-Chloro-5-hydroxyanilino)-2-(4-pyridinyl)-6-(trifluoromethyl)pyrimidine;
4-(2,6-Dimethylanilino)-6-methyl-2-(2-pyridinyl)pyrimidine;
4-(3-Methoxyanilino)-2,6-di(2-pyridinyl)pyrimidine;
4-(2,5-Dimethoxyanilino)-2,6-di(2-pyridinyl)pyrimidine;
4-(5-Methoxy-2-methylanilino)-2,6-di(2-pyridinyl)pyrimidine;
4-(2-Methoxy-5-methylanilino)-2,6-di(2-pyridinyl)pyrimidine;
4-(2-Chloro-5-methoxyanilino)-2,6-di(2-pyridinyl)pyrimidine;
4-(2,5-Dimethylanilino)-2,6-di(2-pyridinyl)pyrimidine;
4-(2,5-Dimethylanilino)-2-(4-pyridinyl)-6-(trifluoromethyl)pyrimidine hydrochloride;
4-(2-Methoxy-5-methylanilino)-2-(4-pyridinyl)-6-(trifluoromethyl)pyrimidine;
4-(5-Hydroxy-2-methylanilino)-2-(3-pyridinyl)-6-(trifluoromethyl)pyrimidine;
4-(5-Hydroxy-2-methylanilino)-2-(4-pyridinyl)-6-(trifluoromethyl)pyrimidine;
4-(2-Cyano-5-methylanilino)-2-(3-pyridinyl)-6-(trifluoromethyl)pyrimidine;
4-(3,5-Dimethylanilino)-2-(3-pyridinyl)-6-(trifluoromethyl)pyrimidine;
4-(3,5-Dimethoxyanilino)-2-(3-pyridinyl)-6-(trifluoromethyl)pyrimidine hydrochloride;
4-(2-Chloro-5-methylanilino)-2-(3-pyridinyl)-6-(trifluoromethyl)pyrimidine;
4-(3-Methoxy-5-trifluoromethylanilino)-2-(3-pyridinyl)-6-(trifluoromethyl)pyrimidine;
4-(2-Chloro-5-methoxyanilino)-2-[6-(trifluoromethyl)-3-pyridinyl]-6-(trifluoromethyl)pyrimidine;
4-(5-Bromo-2-methoxyanilino)-2-(3-pyridinyl)-6-(trifluoromethyl)pyrimidine;
4-(2-Bromo-5-methoxyanilino)-2-(3-pyridinyl)-6-(trifluoromethyl)pyrimidine;
4-[3-Methyl-5-(trifluoromethyl)anilino]-2-(3-pyridinyl)-6-(trifluoromethyl)pyrimidine;
4-(5-Chloro-2-hydroxyanilino)-2-(3-pyridinyl)-6-(trifluoromethyl)pyrimidine;
4-(4-Chloro-2,5-dimethoxyanilino)-2-(3-pyridinyl)-6-(trifluoromethyl)pyrimidine hydrochloride;
4-(2,4-Dichloro-5-methoxyanilino)-2-(3-pyridinyl)-6-(trifluoromethyl)pyrimidine;
4-(Indol-4-ylamino)-2-(3-pyridinyl)-6-(trifluoromethyl)pyrimidine;
4-(2-Acetyl-4,5-dimethoxyanilino)-2-(3-pyridinyl)-6-(trifluoromethyl)pyrimidine;
4-(2-Methyl-5-nitroanilino)-2-(4-pyridinyl)-6-(trifluoromethyl)pyrimidine;
4-(5-Amino-2-methylanilino)-2-(4-pyridinyl)-6-(trifluoromethyl)pyrimidine;

N-[4-Methyl-3-(2-pyridin-3-yl-6-(trifluoromethyl)pyrimidin-4-ylamino)-phenyl]benzamide;

4-Methyl-N-[4-methyl-3-(2-pyridin-4-yl-6-(trifluoromethyl)pyrimidin-4-ylamino)-phenyl]benzamide;

N-[4-Methyl-3-(2-pyridin-4-yl-6-(trifluoromethyl)pyrimidin-4-ylamino)-phenyl]nicotinamide;

6-Chloro-N-[4-methyl-3-(2-pyridin-4-yl-6-(trifluoromethyl)pyrimidin-4-ylamino)-phenyl]nicotinamide;

N-[4-Methyl-3-(2-pyridin-4-yl-6-(trifluoromethyl)pyrimidin-4-ylamino)-phenyl]-4-morpholino-benzamide;

4-Chloro-N-[4-methyl-3-(2-pyridin-4-yl-6-(trifluoromethyl)pyrimidin-4-ylamino)-phenyl]benzamide;

4-Methoxy-N-[4-methyl-3-(2-pyridin-4-yl-6-(trifluoromethyl)pyrimidin-4-ylamino)-phenyl]benzamide;

4-Chloromethyl-N-[4-methyl-3-(2-pyridin-4-yl-6-(trifluoromethyl)pyrimidin-4-ylamino)-phenyl]benzamide;

4-(4-Methyl-piperazin-1-ylmethyl)-N-[4-methyl-3-(2-pyridin-4-yl-6-(trifluoromethyl)pyrimidin-4-ylamino)-phenyl]benzamide;

4-(2,5-Dimethyl-4-hydroxyanilino)-2-(2-pyridinyl)-6-(trifluoromethyl)pyrimidine hydrochloride;

4-(2,5-Dimethyl-4-hydroxyanilino)-(2-pyrazinyl)-6-(trifluoromethyl)pyrimidine hydrochloride;

4-(2,5-Dimethyl-4-hydroxyanilino)-2-(4-pyridinyl)-6-(trifluoromethyl)pyrimidine;

4-(4-Chloro-2,5-dimethoxyanilino)-2-(2-pyridinyl)-6-(trifluoromethyl)pyrimidine hydrochloride;

4-(4-Chloro-2,5-dimethoxyanilino)-(2-pyrazinyl)-6-(trifluoromethyl)pyrimidine hydrochloride;

4-(4,5-Dimethoxy-2-methylanilino)-2-(2-pyridinyl)-6-(trifluoromethyl)pyrimidine hydrochloride;

4-(4,5-Dimethoxy-2-methylanilino)-2-(2-pyrazinyl)-6-(trifluoromethyl)pyrimidine hydrochloride;

4-(4,5-Dimethoxy-2-methylanilino)-2-(4-pyridinyl)-6-(trifluoromethyl)pyrimidine hydrochloride;

4-(3-Trifluoromethoxyanilino)-2-(2-pyridinyl)-6-(trifluoromethyl)pyrimidine hydrochloride;

4-(4,5-Dimethoxy-2-methylanilino)-2-(3-pyridinyl)-6-(trifluoromethyl)pyrimidine 4-(4-Chloro-2,5-dimethoxyanilino)-2-(4-pyridinyl)-6-(trifluoromethyl)pyrimidine hydrochloride;

4-(2-Hydroxy-5-methylanilino)-2-(3-pyridinyl)-6-(trifluoromethyl)pyrimidine;

4-(3,5-Dimethoxyanilino)-2-(4-pyridinyl)-6-trifluoromethylpyrimidine;

4-(5-Chloro-2-methoxyanilino)-2-(4-pyridinyl)-6-trifluoromethylpyrimidine;

4-(Indol-5-ylamino)-2-(3-pyridinyl)-6-trifluoromethylpyrimidine;

6-Methyl-4-(3-phenoxyanilino)-2-(2-pyridinyl)pyrimidine;

4-(3-Chloroanilino)-6-methyl-2-(2-pyridinyl)pyrimidine;

4-(3,4-Dimethoxyanilino)-6-methyl-2-(2-pyridinyl)pyrimidine;

4-(4-Fluoro-3-methoxyanilino)-6-methyl-2-(2-pyridinyl)pyrimidine;

4-(3-Isopropoxyanilino)-6-methyl-2-(2-pyridinyl)pyrimidine;

4-(3,4-Dimethoxyanilino)-6-trifluoromethyl-2-(2-pyridinyl)pyrimidine;

4-(5-Chloro-2-methoxyanilino)-2-(3-pyridinyl)-6-trifluoromethylpyrimidine;

4-(2-Methoxy-5-nitroanilino)-2-(2-pyrazinyl)-6-trifluoromethylpyrimidine;

4-(5-Methoxy-2-nitroanilino)-2-(2-pyrazinyl)-6-trifluoromethylpyrimidine;

4-(3,5-Dimethoxyanilino)-2-(2-pyrazinyl)-6-trifluoromethylpyrimidine;

4-(5-Carboxy-2-methoxyanilino)-2-(2-pyrazinyl)-6-trifluoromethylpyrimidine;

4-(2-Methoxy-5-methylanilino)-2-(2-pyrazinyl)-6-trifluoromethylpyrimidine;

4-(5-Hydroxy-2-methylanilino)-2-(2-pyridinyl)-6-trifluoromethylpyrimidine;

4-(2-Chloro-5-hydroxyanilino)-2-(2-pyridinyl)-6-trifluormethylpyrimidine;

4-(2-Methoxy-5-methylanilino)-2-(2-pyridinyl)-6-trifluoromethylpyrimidine;

4-(2-Hydroxy-5-isopropylanilino)-2-(2-pyridinyl)-6-trifluoromethylpyrimidine;

4-(5-Hydroxy-2-methylanilino)-2-(2-pyrazinyl)-6-trifluoromethylpyrimidine;

4-(2-Chloro-5-hydroxyanilino)-2-(2-pyrazinyl)-6-trifluoromethylpyrimidine;

4-(3,5-Dimethoxyanilino)-2-(2-pyridinyl)-6-trifluoromethylpyrimidine;

4-(2,5-Dimethylanilino)-2-(2-pyrazinyl)-6-trifluoromethylpyrimidine;

4-(5-Chloro-2-methoxyanilino)-2-(2-pyrazinyl)-6-trifluoromethylpyrimidine;

4-(5-Chloro-2-hydroxyanilino)-2-(2-pyrazinyl)-6-trifluoromethylpyrimidine;

4-(5-Hydroxy-2-isopropylanilino)-2-(2-pyrazinyl)-6-trifluoromethypyrimidine;

4-(2,5-Dimethyl-4-hydroxyanilino)-2-(3-pyridinyl)-6-trifluoromethylpyrimidine;

4-(2-Cyano-4,5-dimethoxyanilino)-2-(3-pyridinyl)-6-trifluoromethylpyrimidine;

4-(2,6-Dimethoxypyridin-3-ylamino)-2-(3-pyridinyl)-6-trifluoromethylpyrimidine;

4-(2-Methoxy-pyridin-5-ylamino)-2-(3-pyridinyl)-6-trifluoromethylpyrimidine;

4-(4,6-Dimethoxy-pyrimidin-2-ylamino)-2-(3-pyridinyl)-6-trifluoromethylpyrimidine;

4-(5-Chloro-2-methyl-pyrimidin-4-ylamino)-2-(3-pyridinyl)-6-trifluoromethylpyrimidine;

4-(2-Hydroxy-5-methyl-pyrimidin-4-ylamino)-2-(3-pyridinyl)-6-trifluoromethylpyrimidine;

4-(Indol-4-ylamino)-2-(2-pyridinyl)-6-trifluoromethylpyrimidine;

4-(2-Methyl-indol-5-ylamino)-2-(3-pyridinyl)-6-trifluoromethylpyrimidine;

4-(2-Chloro-5-methoxy-anilino)-2-(2-pyrimidinyl)-6-trifluoromethylpyrimidine hydrochloride;

4-(2-Chloro-5-methoxyanilino)-2-(3-pyridinyl)-6-(t-butyl)pyrimidine;

4-(3-Methoxyanilino)-2-(2-piperidinyl)-6-(trifluoromethyl)pyrimidine;

4-(2-Chloro-5-methoxyanilino)-2-(4-pyridinyl-N-oxide)-6-(trifluoromethyl)pyrimidine;

4-(4-Chloro-2-methoxy-5-methylanilino)-2-(3-pyridinyl)-6-(trifluoromethyl)pyrimidine;

4-(2,4,5-Trimethylanilino)-2-(3-pyridinyl)-6-(trifluoromethyl)pyrimidine; and 4-(2,4-Dichloro-5-hydroxyanilino)-2-(3-pyridinyl)-6-(trifluoromethyl)pyrimidine.

The present invention is also directed to novel compounds within the scope of Formulae I–III. Exemplary preferred compounds that may be employed in this invention include, without limitation:

4-(3-Methoxyanilino)-6-methyl-2-(2-pyridinyl)pyrimidine;

4-(4-Methoxyanilino)-6-methyl-2-(2-pyridinyl)pyrimidine;

4-(3-Fluoroanilino)-6-methyl-2-(2-pyridinyl)pyrimidine;

4-(3-Methylanilino)-6-methyl-2-(2-pyridinyl)pyrimidine;

4-(4-Methoxyanilino)-2-(3-methylphenyl)-6-(methoxymethyl)pyrimidine;

4-(3-Benzyloxyanilino)-6-methyl-2-(2-pyridinyl)pyrimidine;

4-(3-Ethoxyanilino)-6-methyl-2-(2-pyridinyl)pyrimidine;

4-(3-Cyanoanilino)-6-methyl-2-(2-pyridinyl)pyrimidine;

4-(3-Acetophenonanilino)-6-methyl-2-(2-pyridinyl)pyrimidine;

4-(3-Methoxyanilino)-2-(3-methylphenyl)-6-(methoxymethyl)pyrimidine;

4-(2,5-Dimethoxyanilino)-6-methyl-2-(2-pyridinyl)pyrimidine;

4-[3-(Trifluoromethyl)anilino]-6-methyl-2-(2-pyridinyl)pyrimidine;

4-(3-Acetoanilino)-6-methyl-2-(2-pyridinyl)pyrimidine;

4-(3-Nitroanilino)-6-methyl-2-(2-pyridinyl)pyrimidine;

4-[3-(Trifluoromethoxy)anilino]-6-methyl-2-(2-pyridinyl)pyrimidine;

4-[3-(Methylthio)anilino]-6-methyl-2-(2-pyridinyl)pyrimidine;

4-(3-Dimethylaminoanilino)-6-methyl-2-(2-pyridinyl)pyrimidine;

4-(3-Isopropylanilino)-6-methyl-2-(2-pyridinyl)pyrimidine;

4-(2,5-Dimethoxyanilino)-2-(3-pyridinyl)-6-(trifluoromethyl)pyrimidine;

4-(2,5-Dimethoxyanilino)-6-(methoxymethyl)-2-(3-methylphenyl)pyrimidine;

4-(3-Methoxy-phenoxy)-6-methyl-2-(2-pyridinyl)pyrimidine;

4-(3-Methoxyanilino)-2-(4-pyridinyl)-6-(trifluoromethyl)pyrimidine;

4-(2,5-Dimethoxyanilino)-2-(4-pyridinyl)-6-(trifluoromethyl)pyrimidine;

4-(2,5-Dimethoxyanilino)-5-methoxy-2-(2-pyridinyl)pyrimidine;

4-(3-Methoxyanilino)-6-(methoxymethyl)-2-(2-methyl-1-3-thiazol-4-yl)pyrimidine;

4-(2,5-Dimethoxyanilino)-6-(methoxymethyl)-2-(2-methyl-1-3-thiazol-4-yl)pyrimidine;

6-Morpholino-4-(3-methoxyanilino)-2-phenyl-pyrimidine;

6-Morpholino-4-(2,5-dimethoxyanilino)-2-phenyl-4-pyrimidine;

4-(2-Chloro-5-methoxyanilino)-6-(methoxymethyl)-2-(2-methyl-1,3-thiazol-4-yl)pyrimidine;

4-(5-Methoxy-2-methylanilino)-6-(methoxymethyl)-2-(2-methyl-1,3-thiazol-4-yl)pyrimidine;

4-(2-Chloro-5-methoxyanilino)-2-(3-pyridinyl)-6-(trifluoromethyl)pyrimidine;

4-(5-Methoxy-2-methylanilino)-2-(3-pyridinyl)-6-(trifluoromethyl)pyrimidine;

4-(2-Chloro-5-methoxyanilino)-6-methyl-2-(2-pyridinyl)pyrimidine;

4-(5-Methoxy-2-methylanilino)-6-methyl-2-(2-pyridinyl)pyrimidine;

4-(2-Chloro-5-methoxyanilino)-2-(4-pyridinyl)-6-(trifluoromethyl)pyrimidine;

4-(5-Methoxy-2-methylanilino)-2-(4-pyridinyl)-6-(trifluoromethyl)pyrimidine;

4-(2-Chloro-5-methoxyanilino)-6-(methoxymethyl)-2-(3-methylphenyl)pyrimidine;

4-(5-Methoxy-2-methylanilino)-6-(methoxymethyl)-2-(3-methylphenyl)pyrimidine;

4-[3-(4-Bromo-1-methyl-1H-pyrazol-3-yl)anilino]-2-(3-pyridinyl)-6-(trifluoromethyl)pyrimidine;

4-[3-(2-Methyl-pyrimidin-4-yl)anilino]-2-(3-pyridinyl)-6-(trifluoromethyl)pyrimidine;

4-(3-Phenylanilino)-2-(3-pyridinyl)-6-(trifluoromethyl)pyrimidine;

4-[3-(3-Nitrophenyl)anilino]-2-(3-pyridinyl)-6-(trifluoromethyl)pyrimidine;

4-[3-(2,3,4,5,6-Pentafluorophenoxy)anilino]-2-(3-pyridinyl)-6-(trifluoromethyl)pyrimidine;

4-(2,5-Dimethoxyanilino)-2-(2-pyridinyl)-6-(trifluoromethyl)pyrimidine;

4-[3-(2-Ethyl-1-phenyl-pyrazolin-5-one-3-yl)anilino]-2-(3-pyridinyl)-6-(trifluoromethyl)pyrimidine;

4-[3-(Phenylsulfone)anilino]-2-(3-pyridinyl)-6-(trifluoromethyl)pyrimidine;

4-[3-(N-phenylamide)anilino]-2-(3-pyridinyl)-6-(trifluoromethyl)pyrimidine;

4-(3-Phenoxyanilino)-2-(3-pyridinyl)-6-(trifluoromethyl)pyrimidine;

4-(2,5-Dimethylanilino)-2-(3-pyridinyl)-6-(trifluoromethyl)pyrimidine;

4-(3-Hydroxyanilino)-2-(2-pyridinyl)-6-(trifluoromethyl)pyrimidine hydrochloride;

4-(3,4-Methylenedioxyanilino)-2-(2-pyridinyl)-6-(trifluoromethyl)pyrimidine;

4-(3,4-Methylenedioxyanilino)-2-(4-pyridinyl)-6-(trifluoromethyl)pyrimidine;

4-(3,4-Methylenedioxyanilino)-2-(3-pyridinyl)-6-(trifluoromethyl)pyrimidine;

4-(3-Methoxyanilino)-2-phenyl-6-(trifluoromethyl)pyrimidine;

4-(3-Methoxyanilino)-2-(2-pyrazinyl)-6-(trifluoromethyl)pyrimidine;

4-(2,5-Dimethoxyanilino)-2-phenyl-6-(trifluoromethyl)pyrimidine;

4-(2,5-Dimethoxyanilino)-2-(2-pyrazinyl)-6-(trifluoromethyl)pyrimidine;

4-(3,4-Dimethoxyanilino)-2-phenyl-6-(trifluoromethyl)pyrimidine;

4-(3,4-Dimethoxyanilino)-2-(2-pyrazinyl)-6-(trifluoromethyl)pyrimidine;

4-(5-Methoxy-2-methylanilino)-2-phenyl-6-(trifluoromethyl)pyrimidine;

4-(5-Methoxy-2-methylanilino)-2-(2-pyrazinyl)-6-(trifluoromethyl)pyrimidine;

4-(2-Chloro-5-methoxyanilino)-2-phenyl-6-(trifluoromethyl)pyrimidine;

4-(2-Chloro-5-methoxyanilino)-2-(2-pyrazinyl)-6-(trifluoromethyl)pyrimidine;

4-(3,4-Methylenedioxyanilino)-2-phenyl-6-(trifluoromethyl)pyrimidine;

4-(3,4-Methylenedioxyanilino)-2-(2-pyrazinyl)-6-(trifluoromethyl)pyrimidine;

4-(2-Methoxy-5-phenoxyanilino)-2-(3-pyridinyl)-6-(trifluoromethyl)pyrimidine

4-[2-Methyl-5-(carboxymethylester)anilino]-2-(3-pyridinyl)-6-(trifluoromethyl)pyrimidine;

4-(2-Methoxy-5-methylanilino)-2-(3-pyridinyl)-6-(trifluoromethyl)pyrimidine;

4-(5-Fluoro-2-methylanilino)-2-(3-pyridinyl)-6-(trifluoromethyl)pyrimidine;

4-(2-Methoxy-5-trifluoromethylanilino)-2-(3-pyridinyl)-6-(trifluoromethyl)pyrimidine;

4-(2-Methyl-5-nitroanilino)-2-(3-pyridinyl)-6-(trifluoromethyl)pyrimidine;
4-(5-Amino-2-methylanilino)-2-(3-pyridinyl)-6-(trifluoromethyl)pyrimidine hydrochloride;
4-(3-Ethoxyanilino)-2-(2-pyridinyl)-6-(trifluoromethyl)pyrimidine;
4-(3-Ethylanilino)-2-(2-pyridinyl)-6-(trifluoromethyl)pyrimidine;
4-(5-Methoxy-2-methylanilino)-2-(2-pyridinyl)-6-(trifluoromethyl)pyrimidine;
4-(2-Chloro-5-methoxyanilino)-2-(2-pyridinyl)-6-(trifluoromethyl)pyrimidine;
4-(3-Methylmercaptoanilino)-2-(2-pyridinyl)-6-(trifluoromethyl)pyrimidine;
4-(3-Hydroxyanilino)-2-(3-pyridinyl)-6-(trifluoromethyl)pyrimidine hydrochloride;
4-(3-Hydroxyanilino)-2-(2-pyrazinyl)-6-(trifluoromethyl)pyrimidine hydrochloride;
4-(3-Hydroxyanilino)-2-(4-pyridinyl)-6-(trifluoromethyl)pyrimidine hydrochloride;
4-(2,4-Dimethoxyanilino)-6-methyl-2-(2-pyridinyl)-pyrimidine hydrochloride;
4-(3,5-Dimethoxyanilino)-6-methyl-2-(2-pyridinyl)-pyrimidine hydrochloride;
4-(2,5-Diethoxyanilino)-2-(3-pyridinyl)-6-(trifluoromethyl)pyrimidine;
4-(5-Carboxyl-2-methoxyanilino)-2-(3-pyridinyl)-6-(trifluoromethyl)pyrimidine hydrochloride;
4-(3-Methoxybenzylamino)-2-(3-pyridinyl)-6-(trifluoromethyl)pyrimidine;
4-(5-Carboxyl-2-hydroxyanilino)-2-(3-pyridinyl)-6-(trifluoromethyl)pyrimidine;
4-(2-Chloro-5-hydroxyanilino)-2-(3-pyridinyl)-6-(trifluoromethyl)pyrimidine;
4-(2-Chloro-5-hydroxyanilino)-2-(4-pyridinyl)-6-(trifluoromethyl)pyrimidine;
4-(2,6-Dimethylanilino)-6-methyl-2-(2-pyridinyl)pyrimidine;
4-(3-Methoxyanilino)-2,6-di(2-pyridinyl)pyrimidine;
4-(2,5-Dimethoxyanilino)-2,6-di(2-pyridinyl)pyrimidine;
4-(5-Methoxy-2-methylanilino)-2,6-di(2-pyridinyl)pyrimidine;
4-(2-Methoxy-5-methylanilino)-2,6-di(2-pyridinyl)pyrimidine;
4-(2-Chloro-5-methoxyanilino)-2,6-di(2-pyridinyl)pyrimidine;
4-(2,5-Dimethylanilino)-2,6-di(2-pyridinyl)pyrimidine;
4-(2,5-Dimethylanilino)-2-(4-pyridinyl)-6-(trifluoromethyl)pyrimidine hydrochloride;
4-(2-Methoxy-5-methylanilino)-2-(4-pyridinyl)-6-(trifluoromethyl)pyrimidine;
4-(5-Hydroxy-2-methylanilino)-2-(3-pyridinyl)-6-(trifluoromethyl)pyrimidine;
4-(5-Hydroxy-2-methylanilino)-2-(4-pyridinyl)-6-(trifluoromethyl)pyrimidine;
4-(5-Methoxy-2-piperidino-anilino)-2-(3-pyridinyl)-6-(trifluoromethyl)pyrimidine;
4-(2-Cyano-5-methylanilino)-2-(3-pyridinyl)-6-(trifluoromethyl)pyrimidine;
4-(3,5-Dimethylanilino)-2-(3-pyridinyl)-6-(trifluoromethyl)pyrimidine;
4-(3,5-Dimethoxyanilino)-2-(3-pyridinyl)-6-(trifluoromethyl)pyrimidine hydrochloride;
4-(2-Chloro-5-methoxyanilino)-2-(3-pyridinyl)-6-(trifluoromethyl)pyrimidine;
4-(3-Methoxy-5-trifluoromethylanilino)-2-(3-pyridinyl)-6-(trifluoromethyl)pyrimidine;
4-(2-Chloro-5-methoxyanilino)-2-[6-(trifluoromethyl)-3-pyridinyl]-6-(trifluoromethyl)pyrimidine;
4-(5-Bromo-2-methoxyanilino)-2-(3-pyridinyl)-6-(trifluoromethyl)pyrimidine;
4-(2-Bromo-5-methoxyanilino)-2-(3-pyridinyl)-6-(trifluoromethyl)pyrimidine;
4-[3-Methyl-5-(trifluoromethyl)anilino]-2-(3-pyridinyl)-6-(trifluoromethyl)pyrimidine;
4-(5-Chloro-2-hydroxyanilino)-2-(3-pyridinyl)-6-(trifluoromethyl)pyrimidine;
4-(4-Chloro-2,5-dimethoxyanilino)-2-(3-pyridinyl)-6-(trifluoromethyl)pyrimidine hydrochloride;
4-(2-Chloro-5-methoxyanilino)-2-morpholino-6-(methyl)pyrimidine;
4-(2,4-Dichloro-5-methoxyanilino)-2-(3-pyridinyl)-6-(trifluoromethyl)pyrimidine;
4-(Indol-4-ylamino)-2-(3-pyridinyl)-6-(trifluoromethyl)pyrimidine;
4-(2-Acetyl-4,5-dimethoxyanilino)-2-(3-pyridinyl)-6-(trifluoromethyl)pyrimidine;
4-(2-Methyl-5-nitroanilino)-2-(4-pyridinyl)-6-(trifluoromethyl)pyrimidine;
4-(5-Amino-2-methylanilino)-2-(4-pyridinyl)-6-(trifluoromethyl)pyrimidine;
N-[4-Methyl-3-(2-pyridin-3-yl-6-(trifluoromethyl)pyrimidin-4-ylamino)-phenyl]benzamide;
4-(2,5-Diethoxy-4-morpholinoanilino)-2-(3-pyridinyl)-6-(trifluoromethyl)pyrimidine;
4-Methyl-N-[4-methyl-3-(2-pyridin-4-yl-6-(trifluoromethyl)pyrimidin-4-ylamino)-phenyl]benzamide;
N-[4-Methyl-3-(2-pyridin-4-yl-6-(trifluoromethyl)pyrimidin-4-ylamino)-phenyl]nicotinamide;
6-Chloro-N-[4-methyl-3-(2-pyridin-4-yl-6-(trifluoromethyl)pyrimidin-4-ylamino)-phenyl]nicotinamide;
N-[4-Methyl-3-(2-pyridin-4-yl-6-(trifluoromethyl)pyrimidin-4-ylamino)-phenyl]-4-morpholino-benzamide;
4-Chloro-N-[4-methyl-3-(2-pyridin-4-yl-6-(trifluoromethyl)pyrimidin-4-ylamino)-phenyl]benzamide;
4-Methoxy-N-[4-methyl-3-(2-pyridin-4-yl-6-(trifluoromethyl)pyrimidin-4-ylamino)-phenyl]benzamide;
4-Chloromethyl-N-[4-methyl-3-(2-pyridin-4-yl-6-(trifluoromethyl)pyrimidin-4-ylamino)-phenyl]benzamide;
4-(4-Methyl-piperazin-1-ylmethyl)-N-[4-methyl-3-(2-pyridin-4-yl-6-(trifluoromethyl)pyrimidin-4-ylamino)-phenyl]benzamide;
4-(2,5-Dimethyl-4-hydroxyanilino)-2-(2-pyridinyl)-6-(trifluoromethyl)pyrimidine hydrochloride;
4-(2,5-Dimethyl-4-hydroxyanilino)-(2-pyrazinyl)-6-(trifluoromethyl)pyrimidine hydrochloride;
4-(2,5-Dimethyl-4-hydroxyanilino)-2-(4-pyridinyl)-6-(trifluoromethyl)pyrimidine;
4-(4-Chloro-2,5-dimethoxyanilino)-2-(2-pyridinyl)-6-(trifluoromethyl)pyrimidine hydrochloride;
4-(4-Chloro-2,5-dimethoxyanilino)-(2-pyrazinyl)-6-(trifluoromethyl)pyrimidine hydrochloride;
4-(4,5-Dimethoxy-2-methylanilino)-2-(2-pyridinyl)-6-(trifluoromethyl)pyrimidine hydrochloride;
4-(4,5-Dimethoxy-2-methylanilino)-2-(2-pyrazinyl)-6-(trifluoromethyl)pyrimidine hydrochloride;
4-(4,5-Dimethoxy-2-methylanilino)-2-(4-pyridinyl)-6-(trifluoromethyl)pyrimidine hydrochloride;
4-(2-Chloro-5-methoxyanilino)-6-methyl-2-aminopyrimidine;
4-(3-Trifluoromethoxyanilino)-2-(2-pyridinyl)-6-(trifluoromethyl)pyrimidine hydrochloride;
4-(4,5-Dimethoxy-2-methylanilino)-2-(3-pyridinyl)-6-(trifluoromethyl)pyrimidine 4-(4-Chloro-2,5-dimethoxyanilino)-2-(4-pyridinyl)-6-(trifluoromethyl)pyrimidine hydrochloride;

4-(2-Hydroxy-5-methylanilino)-2-(3-pyridinyl)-6-(trifluoromethyl)pyrimidine;

4-(N-Methyl-3-methoxyanilino)-2-(2-pyridinyl)-6-trifluoromethylpyrimidine;

4-(3,5-Dimethoxyanilino)-2-(4-pyridinyl)-6-trifluoromethylpyrimidine;

4-(5-Chloro-2-methoxyanilino)-2-(4-pyridinyl)-6-trifluoromethylpyrimidine;

4-(3,5-Dimethoxyanilino)-2-(2,6-dichloro-4-pyridinyl)-6-trifluoromethyl-pyrimidine;

4-(2-Chloro-5-methoxyanilino)-2-(2,6-dichloro-4-pyridinyl)-6-trifluoromethyl-pyrimidine;

4-(2-Methoxy-5-methyl-4-nitroanilino)-2-(3-pyridinyl)-6-trifluoromethyl-pyrimidine;

4-(Indol-5-ylamino)-2-(3-pyridinyl)-6-trifluoromethylpyrimidine;

4-(5-Methoxy-2-methyl-4-nitroanilino)-2-(3-pyridinyl)-6-trifluoromethyl-pyrimidine;

4-(3-Trifluoromethyl-1-pyrazolyl)-2-(3-pyridinyl)-6-trifluoromethylpyrimidine;

4-(4,5-Dihydro-2-thiazolyl-amino)-2-(3-pyridinyl)-6-trifluoromethylpyrimidine;

4-(1-Pyrazolyl)-2-(3-pyridinyl)-6-trifluoromethyl-pyrimidine;

4-(4,5,6,7-Tetrahydro-indazol-1-yl)-2-(3-pyridinyl)-6-trifluoromethylpyrimidine;

4-(1H-3-Pyrazolyl-amino)-2-(3-pyridinyl)-6-trifluoromethylpyrimidine;

6-Methyl-2-(2-pyridinyl)-4-(3-trifloromethylbenzylamino)-pyrimidine;

6-Methyl-4-(3-phenoxyanilino)-2-(2-pyridinyl)pyrimidine;

4-(3-Chloroanilino)-6-methyl-2-(2-pyridinyl)pyrimidine;

4-(3,4-Dimethoxyanilino)-6-methyl-2-(2-pyridinyl)pyrimidine;

4-(4-Fluoro-3-methoxyanilino)-6-methyl-2-(2-pyridinyl)pyrimidine;

4-(3-Isopropoxyanilino)-6-methyl-2-(2-pyridinyl)pyrimidine;

4-(3,4-Dimethoxyanilino)-6-trifluoromethyl-2-(2-pyridinyl)pyrimidine;

4-(5-Chloro-2-methoxyanilino)-2-(3-pyridinyl)-6-trifluoromethylpyrimidine;

4-(2-Methoxy-5-nitroanilino)-2-(2-pyrazinyl)-6-trifluoromethylpyrimidine;

4-(5-Methoxy-2-nitroanilino)-2-(2-pyrazinyl)-6-trifluoromethylpyrimidine;

4-(3,5-Dimethoxyanilino)-2-(2-pyrazinyl)-6-trifluoromethylpyrimidine;

4-(5-Carboxy-2-methoxyanilino)-2-(2-pyrazinyl)-6-trifluoromethylpyrimidine;

4-(5-Hydroxy-2-nitroanilino)-2-(3-pyridinyl)-6-trifluoromethylpyrimidine;

4-(2-Ethanesulfonyl-5-hydroxyanilino)-2-(2-pyrazinyl)-6-trifluoromethylpyrimidine;

4-(2-Methoxy-5-methylanilino)-2-(2-pyrazinyl)-6-trifluoromethylpyrimidine;

4-(5-Hydroxy-2-methylanilino)-2-(2-pyridinyl)-6-trifluoromethylpyrimidine;

4-(2-Chloro-5-hydroxyanilino)-2-(2-pyridinyl)-6-trifluormethylpyrimidine;

4-(2-Methoxy-5-methylanilino)-2-(2-pyridinyl)-6-trifluoromethylpyrimidine;

4-(2-Ethanesulfonyl-5-hydroxyanilino)-2-(2-pyridinyl)-6-trifluoromethylpyrimidine;

4-(2-Hydroxy-5-isopropylanilino)-2-(2-pyridinyl)-6-trifluoromethylpyrimidine;

4-(5-Hydroxy-2-methylanilino)-2-(2-pyrazinyl)-6-trifluoromethylpyrimidine;

4-(2-Chloro-5-hydroxyanilino)-2-(2-pyrazinyl)-6-trifluoromethylpyrimidine;

4-(3,5-Dimethoxyanilino)-2-(2-pyridinyl)-6-trifluoromethylpyrimidine;

4-(2,5-Dimethylanilino)-2-(2-pyrazinyl)-6-trifluoromethylpyrimidine;

4-(5-Chloro-2-methoxyanilino)-2-(2-pyrazinyl)-6-trifluoromethylpyrimidine;

4-(5-Chloro-2-hydroxyanilino)-2-(2-pyrazinyl)-6-trifluoromethylpyrimidine;

4-(5-Hydroxy-2-isopropylanilino)-2-(2-pyrazinyl)-6-trifluoromethypyrimidine;

4-(2,5-Dimethoxyphenylethylamino)-2-(3-pyridinyl)-6-trifluoromethylpyrimidine;

4-(2,5-Dimethyl-4-hydroxyanilino)-2-(3-pyridinyl)-6-trifluoromethylpyrimidine;

4-(3,4,5-Trichloroanilino)-2-(3-pyridinyl)-6-trifluoromethylpyrimidine;

4-(2-Cyano-4,5-dimethoxyanilino)-2-(3-pyridinyl)-6-trifluoromethylpyrimidine;

4-(3-Methoxy-dibenzofuran-4-ylamino)-2-(3-pyridinyl)-6-trifluoromethylpyrimidine;

4-(1,5,6-Trimethyl-benzimidazol-4-ylamino)-2-(3-pyridinyl)-6-trifluoromethylpyrimidine;

4-(2,6-Dimethoxypyridin-3-ylamino)-2-(3-pyridinyl)-6-trifluoromethylpyrimidine;

4-(2-Methoxy-pyridin-5-ylamino)-2-(3-pyridinyl)-6-trifluoromethylpyrimidine;

4-(4,6-Dimethoxy-pyrimidin-2-ylamino)-2-(3-pyridinyl)-6-trifluoromethylpyrimidine;

4-(5-Chloro-2-methyl-pyrimidin-4-ylamino)-2-(3-pyridinyl)-6-trifluoromethylpyrimidine;

4-(2-Hydroxy-5-methyl-pyrimidin-4-ylamino)-2-(3-pyridinyl)-6-trifluoromethylpyrimidine;

4-(1,3,4-Triazol-1-ylamino)-2-(3-pyridinyl)-6-trifluoromethylpyrimidine;

4-(Indol-4-ylamino)-2-(2-pyridinyl)-6-trifluoromethylpyrimidine;

4-(2-Methyl-indol-5-ylamino)-2-(3-pyridinyl)-6-trifluoromethylpyrimidine;

4-(2-Chloro-5-methoxy-anilino)-2-(2-pyrimidinyl)-6-trifluoromethylpyrimidine hydrochloride;

4-(2-Chloro-5-methoxyanilino)-2-(3-pyridinyl)-6-(t-butyl)pyrimidine;

4-(3-Methoxyanilino)-2-(2-piperidinyl)-6-(trifluoromethyl)pyrimidine;

4-(2-Chloro-5-methoxyanilino)-2-(4-pyridinyl-N-oxide)-6-(trifluoromethyl)pyrimidine;

4-(4-Chloro-2-methoxy-5-methylanilino)-2-(3-pyridinyl)-6-(trifluoromethyl)pyrimidine;

4-(2,4,5-Trimethylanilino)-2-(3-pyridinyl)-6-(trifluoromethyl)pyrimidine; and 4-(2,4-Dichloro-5-hydroxyanilino)-2-(3-pyridinyl)-6-(trifluoromethyl)pyrimidine.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which may be optionally substituted.

Useful alkoxy groups include oxygen substituted by one of the $C_{1-10}$ alkyl groups mentioned above, which may be optionally substituted.

Useful alkylthio groups include sulphur substituted by one of the $C_{1-10}$ alkyl groups mentioned above, which may be optionally substituted. Also included are the sulfoxides and sulfones of such alkylthio groups.

Useful amino groups include —$NH_2$, —$NHR_{15}$ and —$NR_{15}R_{16}$, wherein $R_{15}$ and $R_{16}$ are $C_{1-10}$ alkyl or cycloalkyl groups, or $R_{15}$ and $R_{16}$ are combined with the N to form a ring structure, such as a piperidine, or $R_{15}$ and $R_{16}$ are combined with the N and other group to form a ring, such as a piperazine. The alkyl group may be optionally substituted.

Optional substituents on the alkyl and cycloalkyl groups include one or more halo, hydroxy, carboxyl, amino, nitro, cyano, $C_1$–$C_6$ acylamino, $C_1$–$C_6$ acyloxy, $C_1$–$C_6$ alkoxy, aryloxy, alkylthio, $C_6$–$C_{10}$ aryl, $C_4$–$C_7$ cycloalkyl, $C_2$–$C_6$ alkenyl, $C_2$–$C_6$ alkynyl, $C_6$–$C_{10}$ aryl($C_2$–$C_6$)alkenyl, $C_6$–$C_{10}$ aryl($C_2$–$C_6$)alkynyl, saturated and unsaturated heterocyclic or heteroaryl.

Optional substituents on the aryl, arylalkyl and heteroaryl groups include one or more halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, ureido, cyano, $C_1$–$C_6$ acylamino, hydroxy, thiol, $C_1$–$C_6$ acyloxy, azido, $C_1$–$C_6$ alkoxy or carboxy.

The term "aryl" as employed herein by itself or as part of another group refers to monocyclic, bicyclic or tricyclic aromatic groups containing from 6 to 14 carbons in the ring portion.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

Useful arylalkyl groups include any of the above-mentioned $C_{1-10}$ alkyl groups substituted by any of the above-mentioned $C_{6-14}$ aryl groups. Preferably the arylalkyl group is benzyl, phenylethyl or naphthylmethyl.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino(acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido.

Useful acyloxy groups are any $C_{1-6}$ acyl(alkanoyl) attached to an oxy (—O—) group, e.g., formyloxy, acetoxy, propionoyloxy, butanoyloxy, pentanoyloxy and hexanoyloxy.

The term heterocycle is used herein to mean a saturated or partially saturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms.

Useful heteroaryl groups include thienyl, benzo[b]thienyl, naphtho[2,3-b]thienyl, thianthrenyl, furyl, pyranyl, isobenzofuranyl, chromenyl, xanthenyl, phenoxanthinyl, 2H-pyrrolyl, pyrrolyl, imidazolyl, pyrazolyl, pyridinyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridinyl N-oxide, pyrazinyl N-oxide and pyrimidinyl N-oxide.

Some of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate and oxalate; and inorganic and organic base addition salts with bases such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof such as succinic and fumaric anhydrides according to methods known in the art); phosphate of hydroxy containing compounds (e.g. combretastatin A-1 phosphate prodrug, see Pettit G. R. and Lippert III, J. W., *Anticancer Drug Design* 15:203–216 (2000)); imines of amino containing compounds (e.g., those obtained by condensation with a $C_{1-4}$ aldehyde or ketone according to methods known in the art); carbamate of amino containing compounds such as those described by Leu, et. al., (*J. Med. Chem.* 42:3623–3628 (1999)) and Greenwald, et. al., (*J. Med. Chem.* 42:3657–3667 (1999)); and acetals and ketals of alcohol containing compounds (e.g., those obtained by condensation with chloromethyl methyl ether or chloromethyl ethyl ether according to methods known in the art).

The compounds of this invention may be prepared using methods known to those skilled in the art, or the novel methods of this invention. Specifically, the compounds of this invention with Formulae I–III may be prepared as illustrated by the exemplary reaction in Scheme 1. Reaction of 4-chloro-6-methyl-2-(2-pyridinyl)pyrimidine with aniline gave the product 4-anilino-6-methyl-2-(2-pyridinyl)pyrimidine.

The 2-aryl-4-chloro-pyrimidine may be prepared as illustrated by the exemplary reaction in Scheme 2. Reaction of pyridine-2-carboxamidine with 4,4,4-trifluoro-but-2-ynoic acid ethyl ester in ethanol in the presence of base such as KOH produced the substituted 4-hydroxy-pyrimidine. Treatment of the hydroxy-pyrimidine with POCl$_3$ gave the product 4-chloro-2-(2-pyridinyl)-6-trifluoromethylpyrimidine.

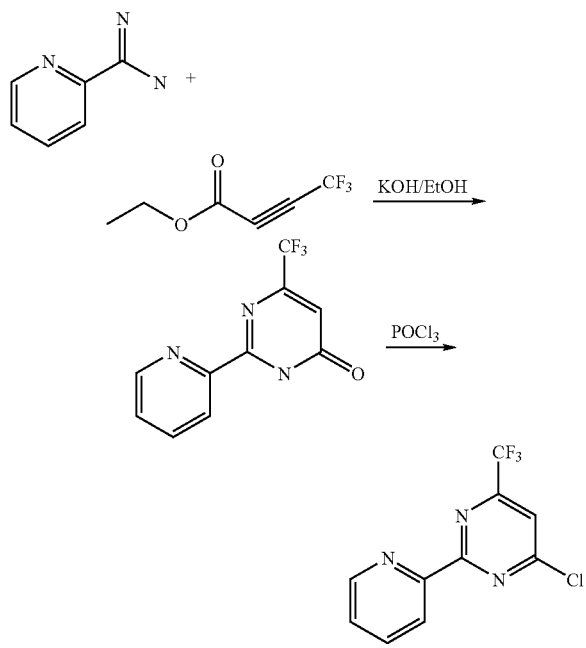

Alternatively, the 2-aryl-4-chloro-pyrimidine may be prepared as illustrated by the exemplary reaction in Scheme 3. Reaction of pyrimidine-2-carboxamidine with ethyl 4,4,4-trifluoro-acetoacetate in ethanol in the presence of base such as EtONa produced the substituted 4-hydroxy-pyrimidine. Treatment of the hydroxy-pyrimidine with POCl$_3$ gave the product 4-chloro-2-(2-pyrimidinyl)-6-trifluoromethylpyrimidine.

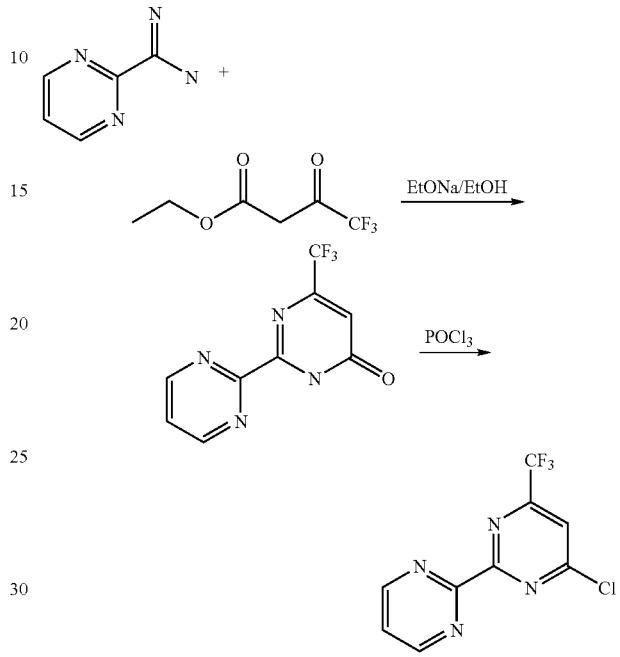

An important aspect of the present invention is the discovery that compounds having Formula I–III are activators of caspases and inducers of apoptosis. Therefore, these compounds are useful in a variety of clinical conditions in which there is uncontrolled cell growth and spread of abnormal cells, such as in the case of cancer.

Another important aspect of the present invention is the discovery that compounds having Formula I–III are potent and highly efficacious activators of caspases and inducers of apoptosis in drug resistant cancer cells, such as breast cancer cells (Examples 11–14), which enables these compounds to kill these drug resistant cancer cells. In comparison, most standard anti-cancer drugs are not effective in killing drug resistant cancer cells under the same conditions. Therefore, compounds of this invention are useful for the treatment of drug resistant cancer such as breast cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of the compound of Formulae I–III, which functions as a caspase cascade activator and inducer of apoptosis.

The present invention also includes a therapeutic method comprising administering to an animal an effective amount of a compound, or a pharmaceutically acceptable salt or prodrug of said compound of Formulae I–III, wherein said therapeutic method is useful to treat cancer, which is a group of diseases characterized by the uncontrolled growth and spread of abnormal cells. Such diseases include, but are not limited to, Hodgkin's disease, non-Hodgkin's lymphomas, acute lymphatic leukemia, chronic lymphocytic leukemia, multiple myeloma, neuroblastoma, breast carcinomas, ovarian carcinomas, lung carcinomas, Wilms' tumor, cervical carcinomas, testicular carcinomas, soft-tissue sarcomas, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head or neck carcinomas, osteogenic sarcoma, pancreatic carcinomas, acute granulocytic leukemia, hairy cell leukemia, neuroblastoma, rhabdomyosarcoma, Kaposi's sarcoma, genitourinary carcinomas, thyroid carcinomas, esophageal carcinomas, malignant hypercalcemia, cervical hyperplasia, renal cell carcinomas, endometrial carcinomas, polycythemia vera, essential thrombocytosis, adrenal cortex carcinomas, skin cancer, and prostatic carcinomas.

In practicing the therapeutic methods, effective amounts of compositions containing therapeutically effective concentrations of the compounds formulated for oral, intravenous, local and topical application, for the treatment of neoplastic diseases and other diseases in which caspase cascade mediated physiological responses are implicated, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms In another embodiment, a pharmaceutical composition comprising a compound, or a pharmaceutically acceptable salt of said compound of Formulae I–III, which functions as a caspase cascade activator and inducer of apoptosis in combination with a pharmaceutically acceptable vehicle is provided.

Another embodiment of the present invention is directed to a composition effective to inhibit neoplasia comprising a compound, or a pharmaceutically acceptable salt or prodrug of said compound of Formulae I–III, which functions as a caspase cascade activator and inducer of apoptosis, in combination with at least one known cancer chemotherapeutic agent, or a pharmaceutically acceptable salt of said agent. Examples of known cancer chemotherapeutic agents which may be used for combination therapy include, but not are limited to alkylating agents such as busulfan, cis-platin, mitomycin C, and carboplatin; antimitotic agents such as coichicine, vinblastine, paclitaxel, and docetaxel; topo I inhibitors such as camptothecin and topotecan; topo II inhibitors such as doxorubicin and etoposide; RNA/DNA antimetabolites such as 5-azacytidine, 5-fluorouracil and methotrexate; DNA antimetabolites such as 5-fluoro-2'-deoxy-uridine, ara-C, hydroxyurea and thioguanine; antibodies such as Herceptin® and Rituxan®. Other known cancer chemotherapeutic agents which may be used for combination therapy include melphalan, chlorambucil, cyclophosphamide, ifosfamide, vincristine, mitoguazone, epirubicin, aclarubicin, bleomycin, mitoxantrone, elliptinium, fludarabine, octreotide, retinoic acid, tamoxifen and alanosine.

In practicing the methods of the present invention, the compound of the invention may be administered together with at least one known chemotherapeutic agent as part of a unitary pharmaceutical composition. Alternatively, the compound of the invention may be administered apart from at least one known cancer chemotherapeutic agent. In one embodiment, the compound of the invention and at least one known cancer chemotherapeutic agent are administered substantially simultaneously, i.e. the compounds are administered at the same time or one after the other, so long as the compounds reach therapeutic levels in vivo at the same time. On another embodiment, the compound of the invention and at least one known cancer chemotherapeutic agent are administered according to their individual dose schedule, so long as the compounds reach therapeutic levels in vivo.

Another embodiment of the present invention is directed to a composition effective to inhibit neoplasia comprising a bioconjugates of said compound of Formulae I–III, which functions as a caspase cascade activator and inducer of apoptosis, in bioconjugation with at least one known therapeutically useful antibody, such as Herceptin® or Rituxan®, growth factors such as EGF, NGF, cytokines such as IL-2, IL-4, or any molecule that binds to the cell surface. The antibodies and other molecules will deliver the compound of Formulae I–III to its targets and make it an effective anticancer agent. The bioconjugates could also enhance the anticancer effect of therapeutically useful antibodies, such as Herceptin® or Rituxan®.

Similarly, another embodiment of the present invention is directed to a composition effective in inhibiting neoplasia comprising a compound, or a pharmaceutically acceptable salt or prodrug of said compound of Formulae I–III, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of said compound of Formulae I–III, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms for maintaining immune homeostasis. The elimination of the effector cells has been shown to be regulated by apoptosis. Autoimmune diseases have lately been determined to occur as a consequence of deregulated cell death. In certain autoimmune diseases, the immune system directs its powerful cytotoxic effector mechanisms against specialized cells such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13–21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly, generalized lymphadenopathy, hypergammaglobulinemia, and autoantibody formation. (Infante, A. J., et al, *J. Pediatr.* 133: 629–633 (1998) and Vaishnaw, A. K., et al., *J. Clin. Invest.*

103:355–363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1:475–483 (1998)). It is therefore evident that many types of autoimmune disease are caused by defects of the apoptotic process. One treatment strategy for such diseases is to turn on apoptosis in the lymphocytes that are causing the autoimmune disease (O'Reilly, L. A. & Strasser, A., *Inflamm. Res.* 48:5–21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 162:603–608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells; both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou T., et al., (*Nat. Med.* 5:42–48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer such as bisindolylmaleimide VIII may be therapeutically useful for the more effective elimination of detrimental cells and inhibition of T cell-mediated autoimmune diseases. Therefore an effective amount of a compound, or a pharmaceutically acceptable salt or prodrug of the compound of Formulae I–III, which functions as a caspase cascade activator and inducer of apoptosis, should be an effective treatment for autoimmune diseases.

Psoriasis is a chronic skin disease that is characterized by scaly red patches. Psoralen plus ultraviolet A (PVA) is a widely used and effective treatment for psoriasis vulgaris and Coven, et al., *Photodermatol. Photoimmunol. Photomed.* 15:22–27 (1999), reported that lymphocytes treated with psoralen 8-MOP or TMP and UVA, displayed DNA degradation patterns typical of apoptotic cell death. Ozawa, et al., *J. Exp. Med.* 189:711–718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290:240–245 (1998), reported that low doses of methotrexate may induce apoptosis and that this mode of action could explain the reduction in epidermal hyperplasia during treatment of psoriasis with methotrexate. Therefore, an effective amount of a compound, or a pharmaceutically acceptable salt or prodrug of the compound of Formulae I–III, which functions as a caspase cascade activator and inducer of apoptosis, should be an effective treatment for psoriasis.

Synovial cell hyperplasia is a characteristic of patients with rheumatoid arthritis (RA). It is believed that excessive proliferation of RA synovial cells, as well as defects in synovial cell death, may be responsible for synovial cell hyperplasia. Wakisaka, et al., *Clin. Exp. Immunol.* 114: 119–128 (1998), found that although RA synovial cells could die via apoptosis through a Fas/FasL pathway, apoptosis of synovial cells was inhibited by proinflammatory cytokines present within the synovium. Wakisaka, et al., also suggested that inhibition of apoptosis by the proinflammatory cytokines may contribute to the outgrowth of synovial cells, and lead to pannus formation and the destruction of joints in patients with RA. Therefore, an effective amount of a compound, or a pharmaceutically acceptable salt or prodrug of the compound of Formulae I–III, which functions as a caspase cascade activator and inducer of apoptosis, should be an effective treatment for rheumatoid arthritis.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61:375–380 (1997)). Boirivant, et al., *Gastroenterology* 116: 557–565 (1999), reported that lamina propria T cells, isolated from areas of inflammation in Crohn's disease, ulcerative colitis, and other inflammatory states, manifest decreased CD2 pathway-induced apoptosis. In addition, studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I–III, which functions as a caspase cascade activator and inducer of apoptosis, should be an effective treatment for inflammation.

Pharmaceutical compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to animals, e.g., mammals, orally at a dose of 0.0025 to 50 mg/kg of body weight, per day, or an equivalent amount of the pharmaceutically acceptable salt thereof, to a mammal being treated for apoptosis-mediated disorders. Preferably, about 0.01 to about 10 mg/kg of body weight is orally administered to treat or prevent such disorders. For intramuscular injection, the dose is generally about one-half of the oral dose. For example, a suitable intramuscular dose would be about 0.0025 to about 25 mg/kg of body weight, and most preferably, from about 0.01 to about 5 mg/kg of body weight. If a known cancer chemotherapeutic agent is also administered, it is administered in an amount that is effective to achieve its intended purpose. The amounts of such known cancer chemotherapeutic agents effective for cancer are well known to those of skill in the art.

The unit oral dose may comprise from about 0.01 to about 50 mg, preferably about 0.1 to about 10 mg of the compound of the invention. The unit dose may be administered one or more times daily as one or more tablets each containing from about 0.1 to about 10, conveniently about 0.25 to 50 mg of the compound or its solvates.

In a topical formulation, the compound may be present at a concentration of about 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which may be used pharmaceutically. Preferably, the preparations, particularly those preparations which may be administered orally and which may be used for the preferred type of administration, such as tablets, dragees, and capsules, and also preparations which may be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular apoptosis inducers of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular apoptosis inducers of the present invention with a solution of a pharmaceutically acceptable non-toxic base such as sodium hydroxide, potassium hydroxide, choline hydroxide, sodium carbonate, Tris, N-methyl-glucamine and the like.

The pharmaceutical compositions of the invention may be administered to any animal which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, crosslinked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which may be used orally include push-fit capsules made of gelatin, as well as soft, sealed capsules made of gelatin and a plasticizer such as glycerol or sorbitol. The push-fit capsules may contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which may be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400) or cremophor, or cyclodextrins. Aqueous injection suspensions may contain substances which increase the viscosity of the suspension include, for example, sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warn soft paraffin and allowing the mixture to cool. A typical example of such an ointment is one which includes about 30% almond oil and about 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

4-(4-Methoxyanilino)-6-methyl-2-(2-pyridinyl)pyrimidine

To a mixture of 6-chloro-4-methyl-2-(2-pyridinyl)pyrimidine (15 mg, 0.56 mmol), p-anisidine (68 mg, 0.55 mmol) in water (10 mL) was added 2 N HCl (0.3 mL). The mixture was refluxed for 6 h, cooled to room temperature, and neutralized with 2N NaOH to pH 10. The resulting mixture was then extracted with 1:1 Hexane/EtOAc (50 mL). The organic phase was washed with water and brine, dried over $Na_2SO_4$ and concentrated in vacuo. The residue was purified by chromatography (1:1 Hexane/EtOAc) to yield the product as a tan solid (72 mg, 45%). $^1$H NMR ($CDCl_3$): 8.80 (d, J=4.5 Hz, 1H), 8.45 (d, J=8.1 Hz, 1H), 7.81 (m, 1H), 7.35 (m, 1H), 7.23 (d, J=8.4 Hz, 2H), 7.12 (s, 1H), 6.93 (d, J=8.4 Hz, 2H), 6.41 (s, 1H), 3.83 (s, 3H), 2.45 (s, 3H).

EXAMPLE 2

4-(3-Fluoroanilino)-6-methyl-2-(2-pyridinyl)pyrimidine

The title compound was prepared using a similar method as described in Example 1. $^1$H NMR ($CDCl_3$): 8.80 (d, J=4.5 Hz, 1H), 8.46 (d, J=7.5 Hz, 1H), 7.84 (m, 1H), 7.56 (s, 1H), 7.39–7.25 (m, 3H), 7.10 (d, J=7.5 Hz, 1H), 6.83 (m, 1H), 6.64 (s, 1H), 2.45 (s, 3H).

EXAMPLE 3

4-(3-Methylanilino)-6-methyl-2-(2-pyridinyl)pyrimidine

The title compound was prepared using a similar method as described in Example 1. $^1$H NMR ($CDCl_3$): 8.79 (d, J=4.5 Hz, 1H), 8.44 (d, J=7.8 Hz, 1H), 7.79 (m, 1H), 7.36–7.09 (m, 5H), 6.98 (d, J=7.5 Hz, 1H), 6.59 (s, 1H), 2.46 (s, 3H), 2.35 (s, 3H).

EXAMPLE 4

4-Anilino-6-methyl-2-(2-pyridinyl)pyrimidine

The title compound was prepared using a similar method as described in Example 1. $^1$H NMR (DMSO-$d_6$): 9.64 (s, 1H), 8.70 (d, J=4.5 Hz, 1H), 8.28 (d, J=7.5 Hz, 1H), 7.94 (m, 1H), 7.78 (s, 1H), 7.75 (s, 1H), 7.47 (m, 1H), 7.31 (m, 1H), 7.02 (m, 1H), 6.66 (s, 1H), 2.38 (s, 3H).

EXAMPLE 5

4-(4-Methoxyanilino)-6-methyl-2-phenylpyrimidine

The title compound was prepared using a similar method as described in Example 1. $^1$H NMR ($CDCl_3$): 8.39–8.36 (m, 2H), 7.48–7.44 (m, 3H), 7.30–7.26 (m, 2H), 6.95–6.93 (m, 2H), 6.68 (s, 1H), 6.32 (s, 1H), 3.84 (s, 3H), 2.38 (s, 3H).

EXAMPLE 6

5-Chloro-4-(4-methoxyanilino)-6-methyl-2-[(5-trifluoromethyl)-2-pyridinyl]pyrimidine The title compound was prepared using a similar method as described in Example 1. $^1$H NMR ($CDCl_3$): 9.06 (m, 1H), 8.43 (m, 1H), 8.04 (m, 1H), 7.59–7.56 (m, 2H), 7.23 (s, 1H), 7.00–6.97 (m, 2H), 3.87 (s, 3H), 2.71 (s, 3H).

EXAMPLE 7

6-(4-Chlorophenyl)-5-cyano-4-(4-methoxyanilino)-2-pyridinylpyrimidine

The title compound was prepared using a similar method as described in Example 1. $^1$H NMR (DMSO-$d_6$): 8.58 (d, J=4.5 Hz, 1H), 8.11 (d, J=7.8 Hz, 1H), 7.88–7.77 (m, 3H), 7.54 (d, J=8.7 Hz, 2H), 7.47–7.39 (m, 3H), 6.85 (d, J=8.7 Hz, 2H), 3.64 (s, 3H).

EXAMPLE 8

4-(4-Methoxyanilino)-2-phenylquinazoline

To a solution of 4-chloro-2-phenylquinazoline (590 mg, 2.45 mmol) in THF (10 mL) was added m-anisidine (301 mg, 2.45 mmol) and NaH (60%, 120 mg, 3.0 mmol). The mixture was refluxed for 24 h. After cooled to room temperature, the mixture was diluted with 1:1 hexane/EtOAc (100 mL), washed with water and brine, dried over $Na_2SO_4$ and concentrated in vacuo. The residue was purified by chromatography (3:1 hexane/EtOAc) to yield the title compound as a white solid (173 mg, 0.53 mmol, 22%). $^1$H NMR ($CDCl_3$): 8.54–8.51 (m, 2H), 8.00–7.74 (m, 5H), 7.52–7.47 (m, 4H), 7.38 (s, 1H), 7.02–7.00 (m, 2H), 3.88 (s, 3H).

EXAMPLE 9

6-Chloro-4-(4-methoxyanilino)-2-phenylpyrimidine

The title compound was prepared using a similar method as described in Example 8. $^1$H NMR ($CDCl_3$): 8.39–8.36 (m, 1H), 8.48–7.46 (m, 3H), 7.28–7.25 (m, 3H), 6.98–6.95 (m, 2H), 6.85 (s, 1H), 6.42 (s, 1H), 3.85 (s, 3H).

EXAMPLE 10

4-(4-Chlorophenyl)-2-(4-methoxyanilino)-6-methylthio-1,3,5-triazine

The title compound was prepared using a similar method as described in Example 1. $^1$H NMR ($CDCl_3$): 8.35 (d, J=8.4 Hz, 1H), 7.52 (d, J=8.7 Hz, 2H), 7.42 (d, J=8.7 Hz, 2H), 7.16 (s, 1H), 6.92 (d, J=8.4 Hz, 2H).

EXAMPLE 11

4-(4-Methoxyanilino)-6-(methoxymethyl)-2-(3-methylphenyl)pyrimidine

A mixture of 4-chloro-6-(methoxymethyl)-2-(3-methylphenyl)pyrimidine (100 mg, 0.402 mmol), p-anisidine (50 mg, 0.402 mmol), water (5 ml) and 2N HCl (300 µl) was refluxed overnight. The resulting yellow solid was collected by filtration, washed with water and then dried under vacuum to give the title compound (55 mg, 41%). $^1$H NMR (CDCl$_3$): 8.28 (d, J=8.7 Hz, 2H), 7.43–7.35 (m, 4H), 6.96 (d, J=9.0 Hz, 2H), 6.83 (s, 1H), 4.64 (s, 2H), 3.85 (s, 3H), 3.45 (s, 3H), 2.44 (s, 3H).

EXAMPLE 12

4-(4-Methoxyanilino)-6-methyl-2-(3-methylphenyl)pyrimidine

The title compound was prepared from 4-chloro-6-methyl-2-(3-methylphenyl)pyrimidine (100 mg, 0.457 mmol) and p-anisidine (56 mg, 0.457 mmol), similar to Example 11 as a pale green solid (39 mg, 28%). $^1$H NMR (DMSO-d$_6$): 8.04 (s, 1H), 8.01–7.99 (m, 1H), 7.56–7.51 (m, 4H), 7.04 (d, J=9.0 Hz, 2H), 6.73 (s, 1H), 3.79 (s, 3H), 2.44 (s, 6H).

EXAMPLE 13

4-(4-Dimethylaminoanilino)-6-(methoxymethyl)-2-(3-methylphenyl)pyrimidine

A mixture of 4-chloro-6-(methoxymethyl)-2-(3-methylphenyl)pyrimidine (100 mg, 0.402 mmol), N,N-dimethyl-1,3-phenylene-diamine dihydrochloride (84 mg, 0.402 mmol), water (5 ml) and 2N HCl (300 µl) was refluxed for 6 h. The mixture was diluted with ethyl acetate (50 ml), washed with water and saturated NaCl. The ethyl acetate solution was dried over anhydrous sodium sulfate, concentrated in vacuo and purified by column chromatography (hexane:ethyl acetate, 3:1) to yield a tan oily product (32 mg, 23%). $^1$H NMR (CDCl$_3$): 8.22–8.20 (m, 1H), 8.18 (s, 1H), 7.34 (t, J=7.5 Hz, 1H), 7.25–7.20 (m, 2H), 6.96 (bs, 1H), 6.89 (s, 1H), 6.82 (s, 1H), 6.67 (dd, J=2.0, 8.0 Hz, 1H), 6.53 (dd, J=2.6, 8.6 Hz, 1H), 4.50 (m, 2H), 3.47 (m, 3H), 2.97 (s, 6H), 2.42 (s, 3H).

EXAMPLE 14

4-(4-Dimethylaminoanilino)-6-methyl-2-(3-methylphenyl)pyrimidine

The title compound was prepared from 4-chloro-6-methyl-2-(3-methylphenyl)pyrimidine (100 mg, 0.457 mmol) and N,N-dimethyl-1,3-phenylene-diamine dihydrochloride (96 mg, 0.457 mmol) similar to Example 13 as a yellow oil (9 mg, 6%). $^1$H NMR (CDCl$_3$): 8.20 (s, 1H), 8.17 (s, 1H), 7.34 (t, J=7.5 Hz, 1H), 7.25–7.21 (m, 2H), 6.82 (t, J=2.1 Hz, 1H), 6.79 (bs, 1H), 6.66 (dd, J=2.0, 7.7 Hz, 1H), 6.54 (dd, J=2.9, 8.9 Hz, 2H), 2.97 (s, 6H), 2.42 (s, 6H).

EXAMPLE 15

4-(3-Methoxyanilino)-5-chloro-6-methyl-2-[5-(trifluoromethyl)-2-pyridinyl]pyrimidine The title compound was prepared from 4,5-dichloro-6-methyl-2-[5-(trifluoromethyl)-2-pyridinyl]pyrimidine (100 mg, 0.325 mmol) and m-anisidine (37 µl, 0.325 mmol) similar to Example 11 as a pale white solid (26 mg, 20%). $^1$H NMR (CDCl$_3$): 9.05 (dd, J=0.8, 1.4 Hz, 1H), 8.53 (d, J=8.4 Hz, 1H), 8.06 (dd, J=2.3, 8.3 Hz, 1H), 7.57 (t, J=2.3 Hz, 1H), 7.36 (s, 1H), 7.31 (t, J=8.1 Hz, 1H), 7.18–7.14 (m, 1H), 6.75–6.72 (m, 1H), 3.88 (s, 3H), 2.71 (s, 3H).

EXAMPLE 16

4-(3-Methoxyanilino)-6-methyl-2-(2-pyridinyl)pyrimidine

The title compound was prepared from 4-chloro-6-methyl-2-(2-pyridinyl)pyrimidine (100 mg, 0.486 mmol) and m-anisidine (55 µl, 0.486 mmol) similar to Example 13 as an tan oil (139 mg, 98%). $^1$HNMR (CDCl$_3$): 8.78–8.75 (m, 1H), 8.45 (dt, J=1.2, 8.1 Hz, 1H), 7.78 (td, J=1.9, 7.8 Hz, 1H), 7.73 (s, 1H), 7.34–7.30 (m, 1H), 7.23 (t, J=8.1 Hz, 1H), 7.03 (t, J=2.1 Hz, 1H), 6.92 (dd, J=2.0, 7.7 Hz, 1H), 6.67 (dd, J=2.4, 8.1 Hz, 1H), 6.61 (s, 1H), 3.77 (s, 3H), 2.44 (s, 3H).

EXAMPLE 17

4-(3-Methoxyanilino)-6-methyl-2-(3-methylphenyl)pyrimidine

The title compound was prepared from 4-chloro-6-methyl-2-(3-methylphenyl)pyrimidine (100 mg, 0.457 mmol) and m-anisidine (51 µl, 0.457 mmol) similar to Example 11 as a pale yellow solid (11 mg, 8%). $^1$H NMR (DMSO-d$_6$): 8.09 (s, 1H), 8.05 (d, J=7.5 Hz, 1H), 7.54–7.49 (m, 4H), 7.35 (t, J=8.1 Hz, 1H), 7.21 (s, 1H), 6.78 (s, 2H), 3.81 (s, 3H), 2.43 (s, 6H).

EXAMPLE 18

4-(3-Methoxyanilino)-5-methoxy-2-(2-pyridinyl)pyrimidine

The title compound was prepared from 4-chloro-5-methoxy-2-(2-pyridinyl)pyrimidine (100 mg, 0.451 mmol) and m-anisidine (51 µl, 0.451 mmol) similar to Example 13 and isolated as a tan oily liquid (63 mg, 45%). $^1$H NMR (CDCl$_3$): 8.76–8.74 (m, 1H), 8.37 (dd, J=1.1, 8.0 Hz, 1H), 8.05 (s, 1H), 7.79–7.73 (m, 2H), 6.65–6.62 (m, 1H), 3.92 (s, 3H), 3.84 (s, 3H).

EXAMPLE 19

4-(3-Methoxyanilino)-2-(3-pyridinyl)-6-(trifluoromethyl)pyrimidine

The title compound was prepared from 4-chloro-2-(3-pyridinyl)-6-(trifluoromethyl)pyrimidine (100 mg, 0.385 mmol) and m-anisidine (43 µl, 0.385 mmol) similar to Example 13 and isolated as a pale yellow solid (38 mg, 29%). $^1$H NMR (Acetone-d$_6$): 9.61 (d, J=2.4 Hz, 1H), 9.42 (s, 1H), 8.76–8.70 (m, 2H), 7.57–7.53 (m, 2H), 7.39 (s, 1H), 7.36 (s, 1H), 7.15 (s, 1H), 6.79–6.75 (m, 1H), 3.87 (s, 3H).

EXAMPLE 20

4-(3-Methoxyanilino)-6-(methoxymethyl)-2-(3-methylphenyl)pyrimidine

The title compound was prepared from 4-chloro-6-(methoxymethyl)-2-(3-methylphenyl)pyrimidine (100 mg, 0.402 mmol) and m-anisidine (45 µl, 0.402 mmol) similar to Example 13 and isolated as a tan solid (154 mg). $^1$H NMR (CDCl$_3$): 8.23 (d, J=9.0 Hz, 2H), 7.34 (s, 1H), 7.25–7.16 (m, 4H), 6.92–6.89 (m, 1H), 6.75 (s, 1H), 6.69–6.65 (m, 1H), 4.51 (s, 2H), 3.78 (s, 3H), 3.47 (s, 3H), 2.40 (s, 3H).

EXAMPLE 21

4-(2,5-Dimethoxyanilino)-6-methyl-2-(2-pyridinyl)pyrimidine

The title compound was prepared from 4-chloro-6-methyl-2-(2-pyridinyl)pyrimidine (100 mg, 0.486 mmol) and 2,5-dimethoxyaniline similar to Example 13 and isolated as a tan oil (116 mg, 74%). $^1$H NMR (CDCl$_3$): 8.78–8.76 (m, 1H), 8.44 (d, J=7.8 Hz, 1H), 7.81 (d, J=2.7 Hz, 1H), 7.79–7.74 (m, 1H). 7.32–7.28 (m, 2H), 6.78 (d, J=9.3 Hz, 1H), 6.60 (s, 1H), 6.53 (dd, J=3.0, 8.7 Hz, 1H), 3.77 (d, J=3.3 Hz, 6H), 2.48 (s, 3H).

EXAMPLE 22

4-(2,3-Dimethoxyanilino)-6-methyl-2-(2-pyridinyl)pyrimidine

The title compound was prepared from 4-chloro-6-methyl-2-(2-pyridinyl)pyrimidine (100 mg, 0.486 mmol) and 2,3-dimethoxyaniline (69 µl, 0.486 mmol) similar to Example 11 and isolated as a white solid (169 mg). $^1$H NMR (CDCl$_3$): 8.85–8.82 (m, 1H), 8.48 (d, J=7.8 Hz, 1H), 7.87–7.82 (m, 1H), 7.54 (d, J=7.5 Hz, 1H), 7.40–7.35 (m, 2H), 7.10 (t, J=8.4 Hz, 1H), 6.73 (d, J=1.5 Hz, 1H), 7.00 (s, 1H), 3.90 (s, 3H), 3.86 (s, 3H), 2.53 (s, 3H).

EXAMPLE 23

4-(3-Benzyloxyanilino)-6-methyl-2-(2-pyridinyl)pyrimidine

The title compound was prepared from 4-chloro-6-methyl-2-(2-pyridinyl)pyrimidine (100 mg, 0.486 mmol) and 3-benzyloxyaniline (97 mg, 0.486 mmol) similar to Example 13 and isolated as a yellow oil (161 mg, 90%). $^1$H NMR (CDCl$_3$): 8.78–8.76 (m, 1H), 8.48–8.45 (m, 1H), 7.79–7.74 (m, 1H), 7.68 (s, 1H), 7.42–7.29 (m, 6H), 7.24 (t, J=8.1 Hz, 1H), 7.10 (s, 1H), 6.92 (dd, J=0.8, 8.0 Hz, 1H), 6.77–6.74 (m, 1H), 6.58 (s, 1H), 5.04 (s, 2H), 2.42 (s, 3H).

EXAMPLE 24

4-(3-Methylanilino)-6-methyl-2-(2-pyridinyl)pyrimidine

The title compound was prepared from 4-chloro-6-methyl-2-(2-pyridinyl)pyrimidine (100 mg, 0.486 mmol) and m-toluidine (52 µl, 0.486 mmol) similar to Example 13 and isolated as a pale yellow oil (132 mg, 99%). $^1$H NMR (CDCl$_3$): 8.76–8.74 (m, 1H), 8.43–8.40 (m, 1H), 7.78–7.72 (m, 1H), 7.55 (s, 1H), 7.31–7.08 (m, 4H), 6.92 (d, J=7.2 Hz, 1H), 6.55 (s, 1H), 2.41 (s, 3H), 2.30 (s, 3H).

EXAMPLE 25

4-(3-Ethoxyanilino)-6-methyl-2-(2-pyridinyl)pyrimidine

The title compound was prepared from 4-chloro-6-methyl-2-(2-pyridinyl)pyrimidine (100 mg, 0.486 mmol) and m-phenetidine (65 µl, 0.486 mmol) similar to Example 11 and isolated as a light tan solid (1116 mg, 78%). $^1$H NMR (CDCl$_3$): 8.86–8.83 (m, 1H), 8.50 (d, J=8.1 Hz, 1H), 7.89–7.83 (m, 1H), 7.42–7.38 (m, 1H), 7.35–7.30 (m, 1H), 7.09 (s, 1H), 6.96–6.84 (m, 2H), 6.76 (d, J=3.3 Hz, 1H), 6.71 (s, 1H), 4.09 (q, J=7.2 Hz, 2H), 2.53 (s, 3H), 1.47 (t, J=7.1 Hz, 3H).

EXAMPLE 26

4-(3-Cyanoanilino)-6-methyl-2-(2-pyridinyl)pyrimidine

The title compound was prepared from 4-chloro-6-methyl-2-(2-pyridinyl)pyrimidine (100 mg, 0.486 mmol) and 3-aminobenzonitrile (57 mg, 0.486 mmol) similar to Example 11 and isolated as a pale white solid (107 mg, 76%). $^1$H NMR (DMSO-d$_6$): 10.14 (s, 1H), 8.78–8.75 (m, 1H), 8.56 (s, 1H), 8.32 (d, J=7.8 Hz, 1H), 8.04–7.96 (m, 2H), 7.60–7.47 (m, 3H), 6.75 (s, 1H), 2.47 (s, 3H).

EXAMPLE 27

4-(3-Acetophenoneanilino)-6-methyl-2-(2-pyridinyl)pyrimidine

The title compound was prepared from 4-chloro-6-methyl-2-(2-pyridinyl)pyrimidine (100 mg, 0.486 mmol) and 3-aminobenzophenone (96 mg, 0.486 mmol) similar to Example 11 and isolated as a light yellow solid (137 mg, 77%). $^1$H NMR (DMSO-d$_6$): 10.76 (s, 1H), 8.78 (d, J=3.9 Hz, 1H), 8.31 (s, 1H), 8.22 (d, J=8.7 Hz, 1H), 8.08 (d, J=9.3 Hz, 1H), 8.02–7.97 (m, 1H), 7.81 (d, J=7.5 Hz, 2H), 7.68–7.51 (m, 6H), 6.85 (s, 1H), 2.5 (s, 3H).

EXAMPLE 28

4-(3-Fluoroanilino)-6-methyl-2-(2-pyridinyl)pyrimidine

The title compound was prepared from 4-chloro-6-methyl-2-(2-pyridinyl)pyrimidine (100 mg, 0.486 mmol) and 3-fluoroaniline (47 µl, 0.486 mmol) similar to Example 11 and isolated as a light brown solid (74 mg, 54%). $^1$H NMR (CDCl$_3$): 8.83 (d, J=4.8 Hz, 1H), 8.47 (d, J=9 Hz, 1H), 7.88 (m, 1H), 7.44–7.30 (m, 4H), 7.18–7.14 (m, 1H), 6.92–6.86 (m, 1H), 6.80 (s, 1H), 2.55 (s, 3H).

EXAMPLE 29

4-(2-Methoxyanilino)-6-methyl-2-(2-pyridinyl)pyrimidine

The title compound was prepared from 4-chloro-6-methyl-2-(2-pyridinyl)pyrimidine (50 mg, 0.243 mmol) and o-anisidine (27 µl, 0.243 mmol) similar to Example 13 and isolated as a pale white solid (40 mg, 56%). $^1$H NMR (CDCl$_3$): 8.82–8.80 (m, 1H), 8.46 (d, J=8.1 Hz, 1H), 7.90 (dd, J=1.4, 7.7 Hz, 1H), 7.84–7.78 (m, 1H), 7.36–7.32 (m, 1H), 7.28 (s, 1H), 7.18–6.98 (m, 2H), 6.92 (dd, J=1.8, 8.0 Hz, 1H), 6.63 (s, 1H), 3.85 (s, 3H), 2.50 (s, 3H).

EXAMPLE 30

4-(3-Trifluoromethylanilino)-6-methyl-2-(2-pyridinyl)pyrimidine

The title compound was prepared from 4-chloro-6-methyl-2-(2-pyridinyl)pyrimidine (50 mg, 0.243 mmol) and 3-aminobenzotrifluoride (30 µl, 0.243 mmol) similar to Example 11 and isolated as a pale white solid (74 mg, 93%). $^1$H NMR (CDCl$_3$): 8.84–8.82 (m, 1H), 8.49–8.45 (m, 1H), 7.95 (s, 1H), 7.90–7.85 (m, 1H), 7.62 (d, J=7.8 Hz, 1H), 7.52 (t, J=7.8 Hz, 1H), 7.45–7.40 (m, 2H), 6.78 (s, 1H), 2.55 (s, 3H).

EXAMPLE 31

4-(3-Acetoanilino)-6-methyl-2-(2-pyridinyl)pyrimidine

The title compound was prepared from 4-chloro-6-methyl-2-(2-pyridinyl)pyrimidine (50 mg, 0.243 mmol) and 3-aminoacetophenone (33 mg, 0.243 mmol) similar to Example 11 and isolated as a white solid (60 mg, 81%). $^1$H NMR (CDCl$_3$): 8.83 (d, J=4.5 Hz, 1H), 8.50 (d, J=8.1 Hz, 1H), 8.13 (s, 1H), 7.89–7.83 (m, 1H), 7.75 (d, J=7.8 Hz, 1H), 7.61–7.48 (m, 2H), 7.41–7.37 (m, 1H), 7.12 (s, 1H), 6.61 (s, 1H), 2.65 (s, 3H), 2.53 (s, 3H).

EXAMPLE 32

4-(3-Trifluoromethoxyanilino)-6-methyl-2-(2-pyridinyl)pyrimidine

The title compound was prepared from 4-chloro-6-methyl-2-(2-pyridinyl)pyrimidine (50 mg, 0.243 mmol) and 3-(trifluoromethoxy)aniline (65 µl, 0.243 mmol) similar to Example 11 and isolated as a pale white solid (78 mg, 93%). $^1$H NMR (DMSO-d$_6$): 9.95 (s, 1H), 8.74 (s, 1H), 8.31 (d, J=9.3 Hz, 2H), 7.95 (t, J=7.7 Hz, 1H), 7.65 (d, J=8.4 Hz, 1H), 7.53–7.43 (m, 2H), 6.98 (d, J=8.4 Hz, 1H), 6.71 (s, 1H), 2.44 (s, 3H).

EXAMPLE 33

4-(3-Ethylanilino)-6-methyl-2-(2-pyridinyl)pyrimidine

The title compound was prepared from 4-chloro-6-methyl-2-(2-pyridinyl)pyrimidine (50 mg, 0.243 mmol) and 3-ethylaniline (60 µl, 0.243 mmol) similar to Example 13 and isolated as an tan oil (69 mg, 98%). $^1$H NMR (CDCl$_3$): 8.81–8.79 (m, 1H), 8.48–8.45 (m, 1H), 7.84–7.78 (m, 1H), 7.42 (s, 1H), 7.37–7.29 (m, 2H), 7.18 (s, 1H), 7.16 (d, J=1.5 Hz, 1H), 7.02 (d, J=7.8 Hz, 1H), 6.61 (s, 1H), 2.66 (q, J=7.5 Hz, 2H), 2.47 (s, 3H), 1.25 (t, J=7.5 Hz, 3H).

EXAMPLE 34

4-(3-Nitroanilino)-6-methyl-2-(2-pyridinyl)pyrimidine

The title compound was prepared from 4-chloro-6-methyl-2-(2-pyridinyl)pyrimidine (50 mg, 0.243 mmol) and 3-nitroaniline (34 mg, 0.243 mmol) similar to Example 11 as a yellow solid (65 mg, 87%). $^1$H NMR (DMSO-d$_6$): 10.17 (s, 1H), 9.18 (s, 1H), 8.77 (d, J=4.8 Hz, 1H), 8.39 (d, J=8.1 Hz, 1H), 8.13 (d, J=7.2 Hz, 1H), 7.98 (t, J=6.9 Hz, 1H), 7.86 (d, J=8.4 Hz, 1H), 7.63 (t, J=8.3 Hz, 1H), 7.55–7.51 (m, 1H), 6.74 (s, 1H), 2.47 (s, 3H).

EXAMPLE 35

4-(3-Methylthioanilino)-6-methyl-2-(2-pyridinyl)pyrimidine

The title compound was prepared from 4-chloro-6-methyl-2-(2-pyridinyl)pyrimidine (50 mg, 0.243 mmol) and 3-(methylthio)aniline (30 µl, 0.243 mmol) similar to Example 13 and isolated as a pink oil (67 mg, 89%). $^1$H NMR (CDCl$_3$): 8.77–8.74 (m, 1H), 8.44–8.41 (m, 1H), 7.81–7.75 (m, 1H), 7.46 (s, 1H), 7.34–7.28 (m, 2H), 7.23 (t, J=8.1 Hz, 1H), 7.09–7.06 (m, 1H), 7.00–6.97 (m, 1H), 6.55 (d, J=0.6 Hz, 1H), 2.44 (s, 3H), 2.43 (d, J=0.6, 3H).

EXAMPLE 36

4-(3-Dimethylaminoanilino)-6-methyl-2-(2-pyridinyl)pyrimidine

The title compound was prepared from a mixture of 4-chloro-6-methyl-2-(2-pyridinyl)pyrimidine (50 mg, 0.243 mmol) and N,N-dimethyl-m-phenylenediamine (51 mg, 0.243 mmol) similar to Example 13 and isolated as a dark green oil (49 mg, 66%). $^1$H NMR (CDCl$_3$): 8.82–8.79 (m, 1H), 8.47 (d, J=7.8 Hz, 1H), 7.84–7.78 (m, 1H), 7.37–7.21 (m, 3H), 6.68–6.66 (m, 3H), 6.58–6.54 (m, 1H), 2.96 (s, 6H), 2.46 (s, 3H).

EXAMPLE 37

4-(3-Isopropylanilino)-6-methyl-2-(2-pyridinyl)pyrimidine

The title compound was prepared from a mixture of 4-chloro-6-methyl-2-(2-pyridinyl)pyrimidine (50 mg, 0.243 mmol) and 3-isopropylaniline (33 µl, 0.243 mmol) similar to Example 13 and isolated as a gray oil (70 mg, 95%). $^1$H NMR (CDCl$_3$): 8.79–8.77 (m, 1H), 8.47–8.43 (m, 1H), 7.81–7.75 (m, 1H), 7.35–7.25 (m, 3H), 7.17–7.12 (m, 2H), 7.02 (d, J=7.5 Hz, 1H), 2.93–2.84 (m, 1H), 2.45 (s, 3H), 1.24 (d, J=6.9 Hz, 6H).

EXAMPLE 38

4-(2,5-Dimethoxyanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (100 mg, 0.385 mmol) and 2,5-dimethoxyaniline (59 mg, 0.385 mmol) similar to Example 13 and isolated as a greenish-yellow solid (24 mg, 17%). $^1$H NMR (CDCl$_3$): 9.67–9.66 (m, 1H), 8.74–8.70 (m, 2H), 8.02 (s, 1H), 7.44–7.39 (m, 1H), 6.91 (s, 1H), 7.67 (s, 1H), 6.87 (d, J=8.7 Hz, 1H), 6.65 (dd, J=3.0, 9.0 Hz, 1H), 3.86 (d, J=7.2 Hz, 6H).

EXAMPLE 39

4-(2,5-Dimethoxyanilino)-6-(methoxymethyl)-2-(3-methylphenyl)pyrimidine

The title compound was prepared from a mixture of 4-chloro-6-(methoxymethyl)-2-(3-methylphenyl)pyrimidine (100 mg, 0.402 mmol) and 2,5-dimethoxyaniline (62 mg, 0.402 mmol) similar to Example 13 and isolated as a pale white solid (65 mg, 45%). $^1$H NMR (CDCl$_3$): 8.30 (d, J=3.0 Hz, 1H), 8.26–8.23 (m, 2H), 7.37–7.25 (m, 3H), 6.81 (d, J=9.0 Hz, 1H), 6.73 (s, 1H), 6.55 (dd, J=3.0, 8.7 Hz, 1H), 4.52 (d, J=0.9 Hz, 2H), 3.87 (s, 3H), 3.83 (s, 3H), 3.51 (s, 3H), 2.42 (s, 3H).

EXAMPLE 40

4-(3-Methoxy-phenoxy)-6-methyl-2-(2-pyridinyl)pyrimidine

The title compound was prepared from a mixture of 4-chloro-6-methyl-2-(2-pyridinyl)pyrimidine (50 mg, 0.243 mmol) and 3-methoxyphenol (27 µl, 0.243 mmol) similar to Example 13 and isolated as a white oil (24 mg, 34%). $^1$H NMR (CDCl$_3$): 8.79–8.76 (m, 1H), 8.26–8.23 (m, 1H), 7.75–7.69 (m, 1H), 7.33–7.28 (m, 2H), 6.82–6.72 (m, 3H), 6.58 (s, 1H), 3.77 (s, 3H), 2.58 (s, 3H).

EXAMPLE 41

4-(3-Methoxyanilino)-2-(4-pyridinyl)-6-(trifluoromethyl)pyrimidine

The title compound was prepared from a mixture of 4-chloro-2-(4-pyridinyl)-6-(trifluoromethyl)pyrimidine (50 mg, 0.193 mmol) and m-anisidine (22 µl, 0.193 mmol) similar to Example 13 and isolated as a yellow solid (31 mg, 46%). $^1$H NMR (CDCl$_3$): 8.77–8.75 (m, 2H), 8.28–8.25 (m, 2H), 7.36 (t, J=8.3 Hz, 1H), 7.13 (s, 1H), 7.03 (s, 1H), 6.98–6.96 (m, 2H), 6.83–6.81 (m, 1H), 3.84 (s, 3H).

EXAMPLE 42

4-(2,5-Dimethoxyanilino)-2-(4-pyridinyl)-6-(trifluoromethyl)pyrimidine

The title compound was prepared from a mixture of 4-chloro-2-(4-pyridinyl)-6-(trifluoromethyl)pyrimidine (50 mg, 0.193 mmol) and 2,5-dimethoxyaniline (32 mg, 0.193 mmol) similar to Example 13 and isolated as a light tan solid (15 mg, 21%). $^1$H NMR (CDCl$_3$): 8.79 (dd, J=1.8, 4.8 Hz, 2H), 8.31 (dd, J=1.8, 4.8 Hz, 2H), 8.02 (bs, 1H), 7.59 (s, 1H), 6.98 (s, 1H), 6.90 (d, J=9.0 Hz, 1H), 6.69 (dd, J=2.9, 9.2 Hz, 1H), 3.90 (s, 3H), 3.87 (s, 3H).

EXAMPLE 43

4-(2,5-Dimethoxyanilino)-5-methoxy-2-(2-pyridinyl)pyrimidine

The title compound was prepared from a mixture of 4-chloro-5-methoxy-2-(2-pyridinyl)pyrimidine (50 mg, 0.226 mmol) and 2,5-dimethoxyaniline (35 mg, 0.226 mmol) similar to Example 11 and isolated as a gray solid (46 mg, 61%). $^1$H NMR (CDCl$_3$): 8.77–8.74 (m, 1H), 8.72 (d, J=3.0 Hz, 1H), 8.43 (d, J=8.1 Hz, 1H), 8.10 (s, 1H), 8.03 (s, 1H), 7.83–7.77 (m, 1H), 7.33–7.29 (m, 1H), 6.84 (d, J=8.7 Hz, 1H), 6.56 (dd, J=3.0, 8.7 Hz, 1H), 4.04 (s, 3H), 3.90 (s, 3H), 3.89 (s, 3H).

EXAMPLE 44

4-(3-Methoxyanilino)-6-(methoxymethyl)-2-(2-methyl-1-3-thiazol-4-yl)pyrimidine The title compound was prepared from a mixture of 4-chloro-6-(methoxymethyl)-2-(2-methyl-1-3-thiazol-4-yl)pyrimidine (50 mg, 0.196 mmol) and m-anisidine (22 µl, 0.196 mmol) similar to Example 11 and isolated as a white solid (29 mg, 43%). $^1$H NMR (CDCl$_3$): 8.10 (s, 1H), 7.28 (t, J=8.1 Hz, 1H), 6.97 (s, 2H), 6.90 (d, J=7.5 Hz, 1H), 6.85 (s, 1H), 6.73–6.70 (m, 1H), 4.52 (s, 2H), 3.82 (s, 3H), 3.45 (s, 3H), 2.81 (s, 3H).

EXAMPLE 45

4-(2,5-Dimethoxyanilino)-6-(methoxymethyl)-2-(2-methyl-1-3-thiazol-4-yl)pyrimidine The title compound was prepared from a mixture of 4-chloro-6-(methoxymethyl)-2-(2-methyl-1-3-thiazol-4-yl)pyrimidine (50 mg, 0.196 mmol) and 2,5-dimethoxyaniline (33 mg, 0.196 mmol) similar to Example 11 and isolated as a gray solid (33 mg, 45%). $^1$H NMR (CDCl$_3$): 8.11 (s, 1H), 7.96 (s, 1H), 7.36 (s, 1H), 6.84–6.81 (m, 2H), 6.56 (dd, J=3.0, 9.0 Hz, 1H), 4.56 (s, 2H), 3.83 (s, 3H), 3.82 (s, 3H), 3.48 (s, 3H), 2.80 (s, 3H).

EXAMPLE 46

6-Morpholino-4-(3-methoxyanilino)-2-phenyl-pyrimidine

A mixture of 4-(6-chloro-2-phenyl-4-pyrimidyl)morpholine (50 mg, 0.181 mmol), m-anisidine (20 µl, 0.181 mmol) and aqueous 2N HCl (150 µl) in water:ethanol (1:1, 10 ml) was refluxed for 5 days. The mixture was cooled to room temperature and basified with aqueous 2N NaOH to pH 10–12. The mixture was extracted with ethyl acetate (50 ml), which was washed with water (2×25 ml), aqueous saturated NaCl, and dried over anhydrous sodium sulfate. The ethyl acetate solution was concentrated in vacuo and isolated as a yellow solid (6 mg, 9%). $^1$H NMR (CDCl$_3$): 8.40–8.37 (m, 2H), 7.46–7.43 (m, 3H), 7.31–7.25 (m, 2H), 7.00 (t, J=2.3 Hz, 1H), 6.91 (dd, J=1.7, 8.0 Hz, 1H), 6.70–6.67 (m, 2H), 3.83 (s, 3H), 3.81–3.63 (m, 8H).

EXAMPLE 47

6-Morpholino-4-(2,5-dimethoxyanilino)-2-phenyl-4-pyrimidine

The title compound was prepared from a mixture of 4-(6-chloro-2-phenyl-4-pyrimidyl)morpholine (50 mg, 0.181 mmol) and 2,5-dimethoxyaniline (28 mg, 0.181 mmol) similar to Example 46 and isolated as a brown oil (6 mg, 8%). $^1$H NMR (DMSO-d$_6$): 8.49 (bs, 1H), 8.33–8.30 (m, 2H), 7.93 (bs, 1H), 6.22 (s, 1H), 7.52–7.50 (m, 3H), 6.99 (dd, J=8.7 Hz, 1H), 6.61 (dd, J=2.7, 8.7 Hz, 1H), 3.81 (s, 3H), 3.76 (s, 3H), 3.74–3.70 (m, 8H).

EXAMPLE 48

4-(2-Chloro-5-methoxyanilino)-6-(methoxymethyl)-2-(2-methyl-1,3-thiazol-4-yl)pyrimidine The title compound was prepared from a mixture of 4-chloro-6-(methoxymethyl)-2-(2-methyl-1,3-thiazol-4-yl)pyrimidine (50 mg, 0.196 mmol) and 2-chloro-5-methoxyaniline (38 mg, 0.196 mmol) similar to Example 13 and isolated as a white solid (33 mg, 45%). $^1$H NMR (CDCl$_3$): 8.14 (s, 1H), 7.93 (d, J=3.0 Hz, 1H), 7.32 (d, J=8.7 Hz, 1H), 7.22 (s, 1H), 6.86 (s, 1H), 6.64 (dd, J=3.0, 9.3 Hz, 1H), 4.60 (s, 2H), 3.88 (s, 3H), 3.52 (s, 3H), 2.84 (s, 3H).

EXAMPLE 49

4-(5-Methoxy-2-methylanilino)-6-(methoxymethyl)-2-(2-methyl-1,3-thiazol-4-yl)pyrimidine The title compound was prepared from a mixture of 4-chloro-6-(methoxymethyl)-2-(2-methyl-1,3-thiazol-4-yl)pyrimidine (50 mg, 0.196 mmol) and 5-methoxy-2-methylaniline (27 mg, 0.196 mmol) similar to Example 13 and isolated as a tan oil (42 mg, 60%). $^1$H NMR (CDCl$_3$): 8.12 (s, 1H), 7.19 (d, J=8.4 Hz, 1H), 6.99 (d, J=2.4 Hz, 1H), 6.89 (s, 1H), 6.75 (dd, J=3.0, 8.7 Hz, 1H), 6.56 (s, 1H), 4.50 (s, 2H), 3.80 (s, 3H), 3.44 (s, 3H), 2.83 (s, 3H), 2.21 (s, 3H).

EXAMPLE 50

4-(2-Chloro-5-methoxyanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 2-chloro-5-methoxyaniline (37 mg, 0.193 mmol) similar to Example 13 and isolated as a white solid (10 mg, 14%). $^1$H NMR (CDCl$_3$): 9.70 (d, J=1.8 Hz, 1H), 8.77–8.74 (m, 2H), 7.86 (s, 1H), 7.67 (s, 1H), 7.48–7.44 (m, 1H), 7.42 (s, 1H), 7.39 (s, 1H), 6.96 (s, 1H), 6.76 (dd, J=3.0, 9.3 Hz, 1H), 3.90 (s, 3H).

EXAMPLE 51

4-(5-Methoxy-2-methylanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 5-methoxy-2-methylaniline (26 mg, 0.193 mmol) similar to Example 13 and isolated as a tan solid (8 mg, 12%). $^1$H NMR (CDCl$_3$): 9.72 (d, J=0.6 Hz, 1H), 8.74–8.68 (m, 2H), 7.70 (s, 1H), 7.44–7.40 (m, 1H), 7.27 (s, 1H), 7.25 (s, 1H), 6.99 (s, 1H), 6.85 (dd, J=2.7, 8.7 Hz, 1H), 6.64 (s, 1H), 3.83 (s, 3H), 2.24 (s, 3H).

EXAMPLE 52

4-(2-Chloro-5-methoxyanilino)-6-methyl-2-(2-pyridinyl)pyrimidine

The title compound was prepared from a mixture of 4-chloro-6-methyl-2-(2-pyridinyl)pyrimidine (50 mg, 0.243 mmol) and 2-chloro-5-methoxyaniline (47 mg, 0.243 mmol) similar to Example 13 and isolated as a tan oil (35 mg, 44%). $^1$H NMR (CDCl$_3$): 8.82–8.80 (m, 1H), 8.47 (d, J=7.8 Hz, 1H), 7.86–7.81 (m, 1H), 7.77 (d, J=2.7 Hz, 1H), 7.41–7.36 (m, 1H), 7.36 (s, 1H), 7.30 (s, 1H), 6.68 (s, 1H), 6.65 (dd, J=2.7, 8.7 Hz, 1H), 3.85 (s, 3H), 2.55 (s, 3H).

EXAMPLE 53

4-(5-Methoxy-2-methylanilino)-6-methyl-2-(2-pyridinyl)pyrimidine

The title compound was prepared from a mixture of 4-chloro-6-methyl-2-(2-pyridinyl)pyrimidine (50 mg, 0.243 mmol) and 5-methoxy-2-methylaniline (33 mg, 0.243 mmol) similar to Example 13 and isolated as a tan oil (45 mg, 60%). $^1$H NMR (CDCl$_3$): 8.78–8.77 (m, 1H), 8.44 (d, J=8.1 Hz, 1H), 7.81–7.75 (m, 1H), 7.34–7.30 (m, 1H), 7.16 (d, J=8.4 Hz, 1H), 6.91 (d, J=2.7 Hz, 2H), 6.72 (dd, J=2.7, 8.7 Hz, 1H), 6.30 (s, 1H), 3.76 (s, 3H), 2.42 (s, 3H), 2.17 (s, 3H).

EXAMPLE 54

4-(2-Chloro-5-methoxyanilino)-2-(4-pyridinyl)-6-(trifluoromethyl)pyrimidine

The title compound was prepared from a mixture of 4-chloro-2-(4-pyridinyl)-6-(trifluoromethyl)pyrimidine (50 mg, 0.193 mmol) and 2-chloro-5-methoxyaniline (38 mg, 0.193 mmol) similar to Example 13 and isolated as a pink solid (18 mg, 25%). $^1$H NMR (CDCl$_3$): 8.82 (dd, J=1.4, 4.7 Hz, 2H), 8.32 (dd, J=1.7, 4.4 Hz, 2H), 7.84 (d, J=2.1 Hz, 1H), 7.50 (s, 1H), 7.41 (d, J=8.7 Hz, 1H), 7.02 (s, 1H), 6.77 (dd, J=3.3, 9.3 Hz, 1H), 3.90 (s, 3H).

EXAMPLE 55

4-(5-Methoxy-2-methylanilino)-2-(4-pyridinyl)-6-(trifluoromethyl)pyrimidine

The title compound was prepared from a mixture of 4-chloro-2-(4-pyridinyl)-6-(trifluoromethyl)pyrimidine (50 mg, 0.193 mmol) and 5-methoxy-2-methylaniline (27 mg, 0.193 mmol) similar to Example 13 and isolated as a pink solid (23 mg, 33%). $^1$H NMR (CDCl$_3$): 8.77 (d, J=5.7 Hz, 2H), 8.27 (d, J=5.7 Hz, 2H), 7.32 (s, 1H), 7.26 (d, J=9.0 Hz, 1H), 6.99 (s, 1H), 6.70 (s, 1H), 6.85 (dd, J=2.7, 8.4 Hz, 1H), 3.82 (s, 3H), 2.24 (s, 3H).

EXAMPLE 56

4-(2-Chloro-5-methoxyanilino)-6-(methoxymethyl)-2-(3-methylphenyl)pyrimidine

The title compound was prepared from a mixture of 4-chloro-6-(methoxymethyl)-2-(3-methylphenyl)pyrimidine (50 mg, 0.201 mmol) and 2-chloro-5-methoxyaniline (39 mg, 0.201 mmol) similar to Example 13 and isolated as a white solid (18 mg, 24%). $^1$H NMR (CDCl$_3$): 8.27–8.25 (m, 3H), 7.40 (t, J=7.7 Hz, 1H), 7.34 (d, J=8.7 Hz, 1H), 7.33 (s, 1H), 7.19 (s, 1H), 6.83 (s, 1H), 6.66 (dd, J=3.0, 9.0 Hz, 1H), 4.59 (s, 2H), 3.93 (s, 3H), 3.58 (s, 3H), 2.47 (s, 3H).

EXAMPLE 57

4-(5-Methoxy-2-methylanilino)-6-(methoxymethyl)-2-(3-methylphenyl)pyrimidine

The title compound was prepared from a mixture of 4-chloro-6-(methoxymethyl)-2-(3-methylphenyl)pyrimidine (50 mg, 0.201 mmol) and 5-methoxy-2-methylaniline (28 mg, 0.201 mmol) similar to Example 13. $^1$H NMR (CDCl$_3$): 8.20–8.16 (m, 2H), 7.35 (t, J=7.5 Hz, 1H), 7.28 (s, 1H), 7.18 (s, 1H), 7.17 (d, J=8.1 Hz, 1H), 6.73 (dd, J=2.7, 8.4 Hz, 1H), 6.61 (s, 1H), 6.57 (s, 1H), 4.49 (s, 2H), 3.82 (s, 3H), 3.47 (s, 3H), 2.44 (s, 3H), 2.23 (s, 3H).

EXAMPLE 58

4-[3-(4-Bromo-1-methyl-1H-pyrazol-3-yl)anilino]-2-(3-pyridinyl)-6-(trifluoromethyl)pyrimidine A mixture of 4-chloro-2-(3-pyridinyl)-6-(trifluoromethyl)pyrimidine (50 mg, 0.193 mmol), 3-(4-bromo-1-methyl-1H-pyrazol-3-yl)aniline (97 mg, 0.386 mmol) and aqueous 2N HCl (150 µl) in water:ethanol (1:1, 10 ml) was refluxed for 24 h. The mixture was cooled to room temperature, extracted with ethyl acetate (50 ml) and washed with water (1×25 ml). The ethyl acetate solution was acidified with aqueous 2N HCl (1×25 ml). The resulting precipitate was collected by filtration, washed with water and isolated as a pale white solid (59 mg, 64%). $^1$H NMR (DMSO-d$_6$): 10.54 (s, 1H), 9.44 (d, J=2.1 Hz, 1H), 8.75 (dd, J=1.8, 4.8 Hz, 1H), 8.62–8.58 (m, 1H), 7.94 (s, 1H), 7.92 (s, 1H), 7.71 (s, 1H), 7.65 (t, J=8.3 Hz, 1H), 7.59–7.54 (m, 1H), 7.28 (d, J=8.1 Hz, 1H), 7.19 (s, 1H), 3.81 (s, 3H).

EXAMPLE 59

4-[3-(2-Methyl-pyrimidin-4-yl)anilino]-2-(3-pyridinyl)-6-(trifluoromethyl)pyrimidine The title compound was prepared from a mixture of 4-chloro-2-(3-pyridinyl)-6-(trifluoromethyl)pyrimidine (50 mg, 0.193 mmol) and 4-(3-aminophenyl)-2-methylpyrimidine (71 mg, 0.386 mmol) similar to Example 58. The mixture was extracted with ethyl acetate (50 ml), washed with water (1×25 ml) and with aqueous 2N HCl (1×25 ml). The acidic aqueous solution was basified with aqueous 2N NaOH to pH 10–12. The resulting precipitate was filtered, washed with water and isolated as a light tan solid (18 mg, 23%). $^1$H NMR (CDCl$_3$): 9.71 (d, J=2.4 Hz, 1H), 8.77–8.72 (m, 3H), 8.38 (s, 1H), 7.89 (d, J=7.2 Hz, 1H), 7.69–7.54 (m, 4H), 7.45–7.41 (m, 1H), 6.95 (s, 1H), 2.83 (s, 3H).

EXAMPLE 60

4-(3-Phenylanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 3-aminobiphenyl (65 mg, 0.386 mmol) similar to Example 58. The mixture was basified with aqueous 2N NaOH to pH 10–12. The resulting precipitate was collected by filtration, washed with excess water:ethanol (1:1) and isolated as a light brown solid (64 mg, 85%). $^1$H NMR (CDCl$_3$): 9.67 (s, 1H), 8.75 (d, J=5.4 Hz, 2H), 7.68 (s, 1H), 7.63–7.37 (m, 10H), 6.98 (s, 1H).

EXAMPLE 61

4-[3-(3-Nitrophenyl)anilino]-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 3-amino-3'-nitrobiphenyl (83 mg, 0.386 mmol) similar to Example 58 and isolated as a light tan solid (65 mg, 77%). $^1$H NMR (DMSO-d$_6$): 13.00 (s, 1H), 11.94 (s, 1H), 11.23 (d, J=4.5 Hz, 1H), 11.11 (d, J=8.1 Hz, 1H), 10.97 (s, 1H), 10.78 (s, 1H), 10.75 (s, 1H), 10.69 (d, J=8.1 Hz, 1H), 10.35–10.28 (m, 2H), 10.14–10.04 (m, 3H), 9.67 (s, 1H).

EXAMPLE 62

4-[3-(2,3,4,5,6-Pentafluorophenoxy)anilino]-2-(3-pyridinyl)-6-(trifluoromethyl)pyrimidine The title compound was prepared from a mixture of 4-chloro-2-(3-pyridinyl)-6-(trifluoromethyl)pyrimidine (50 mg, 0.193 mmol) and 3-(2,3,4,5,6-pentafluorophenoxy)aniline (106 mg, 0.386 mmol) similar to Example 58 and isolated as a yellow solid (65 mg, 68%). $^1$H NMR (DMSO-d$_6$): 10.46 (s, 1H), 9.24 (s, 1H), 8.75 (dd, J=1.8, 4.8 Hz, 1H), 8.56–8.52 (m, 1H), 7.77 (s, 1H), 7.59–7.55 (m, 1H), 7.50–7.41 (m, 2H), 7.14 (s, 1H), 6.94–6.92 (m, 1H).

EXAMPLE 63

4-(2,5-Dimethoxyanilino)-2-(2-pyridinyl)-6-(trifluoromethyl)pyrimidine

The title compound was prepared from a mixture of 4-chloro-2-(2-pyridinyl)-6-(trifluoromethyl)pyrimidine (50 mg, 0.193 mmol) and 2,5-dimethoxyaniline (59 mg, 0.386 mmol) similar to Example 58 and isolated as a light brown solid (36 mg, 50%). $^1$H NMR (DMSO-d$_6$): 9.65 (s, 1H), 8.76–8.73 (m, 1H), 8.32 (d, J=7.8 Hz, 2H), 8.03–7.97 (m, 1H), 7.58–7.54 (m, 2H), 7.05 (d, J=9.0 Hz, 1H), 6.70 (dd, J=3.0, 8.7 Hz, 1H), 3.84 (s, 3H), 3.82 (s, 3H).

EXAMPLE 64

4-[3-(2-Ethyl-1-phenyl-pyrazolin-5-one-3-yl)anilino]-2-(3-pyridinyl)-6-(trifluoromethyl)pyrimidine The title compound was prepared from a mixture of 4-chloro-2-(3-pyridinyl)-6-(trifluoromethyl)pyrimidine (50 mg, 0.193 mmol) and 3-(3-aminophenyl)-2-ethyl-1-phenyl-3-pyrazolin-5-one (54 mg, 0.193 mmol) similar to Example 58 and isolated as a dark yellow solid (52 mg, 54%). $^1$H NMR (DMSO-d$_6$): 10.61 (s, 1H), 9.52 (s, 1H), 8.83–8.81 (m, 1H), 8.65 (dd, J=1.2, 7.5 Hz, 1H), 8.38 (s, 1H), 7.80 (d, J=7.8 Hz, 1H), 7.68–7.48 (m, 7H), 7.37–7.33 (m, 1H), 7.22 (s, 1H), 5.97 (s, 1H), 3.63 (q, J=6.6 Hz, 2H), 0.634 (t, J=6.6 Hz, 3H).

EXAMPLE 65

4-[3-(Phenylsulfone)anilino]-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 3-aminodiphenylsulfone (90 mg, 0.386 mmol) similar to Example 58 and isolated as a yellow solid (44 mg, 50%). $^1$H NMR (CDCl$_3$): 9.68 (d, J=2.4 Hz, 1H), 9.16 (s, 1H), 8.78–8.74 (m, 1H), 8.71–8.69 (m, 1H), 8.61 (s, 1H), 7.97 (d, J=7.2 Hz, 2H), 7.85–7.82 (m, 1H), 7.65 (d, J=7.5 Hz, 1H), 7.56–7.42 (m, 5H), 6.94 (s, 1H).

EXAMPLE 66

4-[3-(N-phenylamide)anilino]-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 3-aminobenzanilide (41 mg, 0.193 μmmol) similar to Example 58 and isolated as a dark pink solid (41 mg, 49%). $^1$H NMR (DMSO-$d_6$): 10.43 (s, 1H), 10.24 (s, 1H), 9.39 (d, J=1.2 Hz, 1H), 8.62 (dd, J=1.5, 4.8 Hz, 1H), 8.57–8.54 (m, 1H), 8.40 (s, 1H), 7.85 (d, J=7.2 Hz, 1H), 7.69 (d, J=8.4 Hz, 2H), 7.63 (d, J=7.2 Hz, 1H), 7.50 (t, J=8.0 Hz, 1H), 7.43–7.39 (m, 1H), 7.25 (t, J=7.8 Hz, 2H), 7.06 (s, 1H), 7.02–6.97 (m, 1H).

EXAMPLE 67

4-(3-Phenoxyanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 3-phenoxyaniline (71 mg, 0.386 mmol) similar to Example 58 and isolated as a pale white solid (33 mg, 42%). $^1$H NMR (CDCl$_3$): 9.74 (d, J=2.1 Hz, 1H), 8.72–8.66 (m, 2H), 8.52 (bs, 1H), 7.45–7.37 (m, 4H), 7.21–7.10 (m, 5H), 6.97 (s, 1H), 6.93 (dd, J=2.1, 8.1 Hz, 1H).

EXAMPLE 68

4-(2,5-Dimethylanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 2,5-dimethylaniline (48 μl, 0.386 mmol) similar to Example 58 and isolated as a light tan solid (14 mg, 21%). $^1$H NMR (CDCl$_3$): 9.70 (dd, J=0.8, 2.0 Hz, 1H), 8.74–8.70 (m, 1H), 8.67 (dd, J=1.8, 4.8 Hz, 1H), 7.75 (s, 1H), 7.43–7.38 (m, 1H), 7.24 (d, J=7.5 Hz, 1H), 7.19 (s, 1H), 7.10 (d, J=7.8 Hz, 1H), 6.56 (s, 1H), 2.38 (s, 3H), 2.26 (s, 3H).

EXAMPLE 69

4-(3-Hydroxyanilino)-2-(2-pyridinyl)-6-(trifluoromethyl)pyrimidine hydrochloride The title compound was prepared from a mixture of 4-chloro-2-(2-pyridinyl)-6-(trifluoromethyl)pyrimidine (89 mg, 0.344 mmol) and 3-aminophenol (30 mg, 0.275 mmol) similar to Example 58 and isolated as a yellow solid (61 mg, 67%). $^1$H NMR (DMSO-$d_6$): 10.40 (s, 1H), 8.86 (dd, J=0.9, 5.1 Hz, 1H), 8.51 (d, J=7.8 Hz, 1H), 8.32–8.26 (m, 1H), 7.82–7.78 (m, 1H), 7.29 (s, 1H), 7.26 (s, 1H), 7.23 (s, 1H), 7.19 (d, J=7.5 Hz, 1H), 6.57 (dd, J=1.8, 9.0 Hz, 1H).

EXAMPLE 70

4-(3,4-Methylenedioxyanilino)-2-(2-pyridinyl)-6-(trifluoromethyl)pyrimidine

The title compound was prepared from a mixture of 4-chloro-2-(2-pyridinyl)-6-(trifluoromethyl)pyrimidine (50 mg, 0.193 mmol) and 3,4-methylenedioxyaniline (53 mg, 0.386 mmol) similar to Example 58 and isolated as a purple solid (24 mg, 35%). $^1$H NMR (CDCl$_3$): 8.85–8.83 (m, 1H), 8.57–8.54 (m, 1H), 7.90–7.84 (m, 1H), 7.45–7.41 (m, 1H), 7.39 (s, 1H), 6.87 (d, J=8.1 Hz, 1H), 6.84 (s, 1H), 6.80 (s, 1H), 6.77 (dd, J=2.1, 8.1 Hz, 1H), 6.05 (s, 2H).

EXAMPLE 71

4-(3,4-Methylenedioxyanilino)-2-(4-pyridinyl)-6-(trifluoromethyl)pyrimidine

The title compound was prepared from a mixture of 4-chloro-2-(4-pyridinyl)-6-(trifluoromethyl)pyrimidine (50 mg, 0.193 mmol) and 3,4-methylenedioxyaniline (53 mg, 0.386 mmol) similar to Example 58 and isolated as a dark brown solid (47 mg, 68%). $^1$H NMR (CDCl$_3$): 8.77 (dd, J=1.5, 4.5 Hz, 2H), 8.26 (dd, J=1.5, 4.5 Hz, 2H), 7.06 (s, 1H), 6.93 (s, 1H), 6.89 (d, J=8.1 Hz, 1H), 6.81 (dd, J=2.1, 8.1 Hz, 1H), 6.81 (s, 1H), 6.06 (s, 2H).

EXAMPLE 72

4-(3,4-Methylenedioxyanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 3,4-methylenedioxyaniline (53 mg, 0.386 mmol) similar to Example 58 and isolated as a light brown solid (37 mg, 53%). $^1$H NMR (CDCl$_3$): 9.63 (dd, J=0.9, 1.8 Hz, 1H), 8.73–8.68 (m, 2H), 7.43–7.39 (m, 1H), 6.93 (s, 1H), 6.88 (d, J=8.1 Hz, 2H), 6.83 (dd, J=1.8, 8.1 Hz, 1H), 6.77 (s, 1H), 6.06 (s, 2H).

EXAMPLE 73

4-(3-Methoxyanilino)-2-phenyl-6-(trifluoromethyl)pyrimidine a. 4-Chloro-2-phenyl-6-(trifluoromethyl)pyrimidine: A mixture of 4-hydroxy-2-phenyl-6-(trifluoromethyl)pyrimidine (1.5 g, 6.24 mmol) and phosphorus oxychloride (25 ml) was refluxed for 3 h. The mixture was cooled to room temperature and then rotary evaporated to dryness. The residual was extracted with ethyl acetate (100 ml), washed with water (2×50 ml), and then with aqueous saturated sodium chloride (1×50 ml). The ethyl acetate solution was dried over anhydrous sodium sulfate and then rotary evaporated to dryness to give a pale white solid (1.6 g, 99%). $^1$H NMR (DMSO-$d_6$): 8.39–8.36 (m, 2H), 8.26 (s, 1H), 7.66–7.57 (m, 3H).

b. 4-(3-Methoxyanilino)-2-phenyl-6-(trifluoromethyl)pyrimidine: A mixture of 4-chloro-2-phenyl-6-(trifluoromethyl)pyrimidine (50 mg, 0.193 mmol), m-anisidine (33 μl, 0.290 mmol) and aqueous 2N HCl (150 μl) in water:ethanol (1:1, 10 ml) was refluxed for 48 h. The mixture was cooled to room temperature and then basified with aqueous 2N NaOH to pH 10–12. The mixture was extracted with ethyl acetate (75 ml), washed with water (2×25 ml), and then with aqueous saturated sodium chloride (1×25 ml). The ethyl acetate solution was dried over anhydrous sodium sulfate and then rotary evaporated to dryness. The residual was purified by column chromatography and isolated as a light gray solid (15 mg, 23%). $^1$H NMR (CDCl$_3$): 8.47–8.44 (m, 2H), 7.51–7.46 (m, 3H), 7.34 (t, J=8.1 Hz, 1H), 7.16 (s, 1H), 7.10 (s, 1H), 6.98 (dd, J=1.5, 7.8 Hz, 1H), 6.89 (s, 1H), 6.81–6.77 (m, 1H), 3.85 (s, 3H).

EXAMPLE 74

4-(3-Methoxyanilino)-2-(2-pyrazinyl)-6-(trifluoromethyl)pyrimidine a. 4-Chloro-2-(2-pyrazinyl)-6-(trifluoromethyl)pyrimidine: A mixture of 4-hydroxy-2-(2-pyrazinyl)-6-(trifluoromethyl)pyrimidine (2.0 g, 8.26 mmol) and phosphorus oxychloride (30 ml) was refluxed for 3 h. The mixture was cooled to room temperature and then rotary evaporated to dryness. The residual was purified by column chromatography and isolated as a tan solid (1.8 g, 84%). $^1$H NMR (DMSO-$d_6$): 9.54 (d, J=1.5 Hz, 1H), 8.92 (dd, J=1.5, 2.4 Hz, 1H), 8.90 (d, J=2.4 Hz, 1H), 8.48 (s, 1H).

b. 4-(3-Methoxyanilino)-2-(2-pyrazinyl)-6-(trifluoromethyl)pyrimidine: A mixture of 4-chloro-2-(2-pyrazinyl)-6-(trifluoromethyl)pyrimidine (50 mg, 0.192 mmol), m-anisidine (32 μl, 0.288 mmol) and aqueous 2N HCl (150 μl) in water:ethanol (1:1, 10 ml) was refluxed for 48 h. The mixture was cooled to room temperature and then basified with aqueous 2N NaOH to pH 10–12. The mixture was extracted with ethyl acetate (75 ml), washed with water (2×25 ml), and then with aqueous saturated sodium chloride (1×25 ml). The ethyl acetate solution was dried over anhydrous sodium sulfate and then rotary evaporated to dryness. The residual was purified by column chromatography and isolated as a yellow solid (38 mg, 57%). $^1$H NMR (CDCl$_3$): 9.74 (d, J=1.2 Hz, 1H), 8.74 (dd, J=1.5, 2.4 Hz, 1H), 8.71 (d, J=2.4 Hz, 1H), 8.04 (s, 1H), 7.34 (t, J=8.1 Hz, 1H), 7.07 (s, 1H), 7.01 (s, 1H), 6.94 (d, J=8.1 Hz, 1H), 6.82 (dd, J=2.7, 8.4 Hz, 1H), 3.84 (s, 3H).

EXAMPLE 75

4-(2,5-Dimethoxyanilino)-2-phenyl-6-(trifluoromethyl)pyrimidine

A mixture of 4-chloro-2-phenyl-6-(trifluoromethyl)pyrimidine (50 mg, 0.193 mmol), 2,5-dimethoxyaniline (44 mg, 0.290 mmol) and aqueous 2N HCl (150 μl) in water:ethanol (1:1, 10 ml) was refluxed for 48 h. The mixture was cooled to room temperature and then basified with aqueous 2N NaOH to pH 10–12. The resulting precipitate was filtered, washed with water, water:ethanol (2:1) and dried under vacuo to give a gray solid (36 mg, 50%). $^1$H NMR (CDCl$_3$): 8.51–8.48 (m, 2H), 8.14 (s, 1H), 7.51–7.48 (m, 4H), 6.89 (s, 1H), 6.88 (d, J=9.3 Hz, 1H), 6.66 (dd, J=3.0, 8.7 Hz, 1H), 3.90 (s, 3H), 3.87 (s, 3H).

EXAMPLE 76

4-(2,5-Dimethoxyanilino)-2-(2-pyrazinyl)-6-(trifluoromethyl)pyrimidine

A mixture of 4-chloro-2-(2-pyrazinyl)-6-(trifluoromethyl) pyrimidine (50 mg, 0.192 mmol), 2,5-dimethoxyaniline and aqueous 2N HCl (150 μl) in water:ethanol (1:1, 10 ml) was refluxed for 48 h. The mixture was cooled to room temperature and then basified with aqueous 2N NaOH to pH 10–12. The resulting precipitate was filtered, washed with water, water:ethanol (2:1) and isolated as a green-yellow solid (46 mg, 64%). $^1$H NMR (CDCl$_3$): 9.74 (d, J=1.5 Hz, 1H), 8.79 (dd, J=1.8, 2.4 Hz, 1H), 8.72 (d, J=2.4 Hz, 1H), 7.80 (bs, 1H), 7.70 (s, 1H), 7.07 (s, 1H), 6.91 (d, J=9.3 Hz, 1H), 6.72 (dd, J=3.0, 9.0 Hz, 1H), 3.87 (s, 3H), 3.86 (s, 3H).

EXAMPLE 77

4-(3,4-Dimethoxyanilino)-2-phenyl-6-(trifluoromethyl)pyrimidine

The title compound was prepared from a mixture of 4-chloro-2-phenyl-6-(trifluoromethyl)pyrimidine (50 mg, 0.193 mmol) and 3,4-dimethoxyaniline (44 mg, 0.290 mmol) similar to Example 75. The mixture was extracted with ethyl acetate (75 ml), washed with water (2×25 ml), washed with aqueous saturated NaCl (1×25 ml), and dried over anhydrous sodium sulfate. The ethyl acetate solution was rotary evaporated to dryness. The residual was purified by column chromatography and isolated as a yellow oil (35 mg, 48%). $^1$H NMR (CDCl$_3$): 8.45–8.42 (m, 2H), 7.50–7.44 (m, 3H), 7.25 (s, 1H), 7.02 (s, 1H), 6.90 (s, 2H), 6.74 (s, 1H), 3.91 (s, 3H), 3.87 (s, 3H).

EXAMPLE 78

4-(3,4-Dimethoxyanilino)-2-(2-pyrazinyl)-6-(trifluoromethyl)pyrimidine

The title compound was prepared from a mixture of 4-chloro-2-(2-pyrazinyl)-6-(trifluoromethyl)pyrimidine (50 mg, 0.192 mmol), 3,4-dimethoxyaniline (44 mg, 0.288 mmol) similar to Example 76 and isolated as a yellow solid (52 mg, 72%). $^1$H NMR (CDCl$_3$): 9.74 (d, J=1.2 Hz, 1H), 8.78 (dd, J=1.2, 2.4 Hz, 1H), 8.72 (d, J=2.4 Hz, 1H), 7.36 (s, 1H), 6.96–6.90 (m, 3H), 6.88 (s, 1H), 3.94 (s, 3H), 3.91 (s, 3H).

EXAMPLE 79

4-(5-Methoxy-2-methylanilino)-2-phenyl-6-(trifluoromethyl)pyrimidine

The title compound was prepared from a mixture of 4-chloro-2-phenyl-6-(trifluoromethyl)pyrimidine (50 mg, 0.193 mmol) and 5-methoxy-2-methylaniline (40 mg, 0.290 mmol) similar to Example 77 and isolated as a tan oil (33 mg, 48%). $^1$H NMR (CDCl$_3$): 8.46–8.42 (m, 2H), 7.50–7.46 (m, 3H), 7.22 (d, J=8.4 Hz, 1H), 7.01 (d, J=2.4 Hz, 1H), 6.92 (s, 1H), 6.80 (dd, J=2.6, 8.6 Hz, 1H), 6.61 (s, 1H), 3.81 (s, 3H), 2.22 (s, 3H).

EXAMPLE 80

4-(5-Methoxy-2-methylanilino)-2-(2-pyrazinyl)-6-(trifluoromethyl)pyrimidine

The title compound was prepared from a mixture of 4-chloro-2-(2-pyrazinyl)-6-(trifluoromethyl)pyrimidine (50 mg, 0.192 mmol), 5-methoxy-2-methylaniline (40 mg, 0.288 mmol) similar to Example 76 and isolated as a yellow solid (40 mg, 58%). $^1$H NMR (CDCl$_3$): 9.75 (d, J=1.2 Hz, 1H), 8.79 (dd, J=1.5, 2.4 Hz, 1H), 8.73 (d, J=2.4 Hz, 1H), 7.28 (d, J=4.5 Hz, 1H), 7.24 (s, 1H), 6.89 (d, J=2.7 Hz, 1H), 6.86 (dd, J=2.7, 8.4 Hz, 1H), 6.73 (s, 1H), 3.82 (s, 3H), 2.22 (s, 3H).

EXAMPLE 81

4-(2-Chloro-5-methoxyanilino)-2-phenyl-6-(trifluoromethyl)pyrimidine

A mixture of 4-chloro-2-phenyl-6-(trifluoromethyl)pyrimidine (50 mg, 0.193 mmol) and 2-chloro-5-methoxyaniline hydrochloride (56 mg, 0.290 mmol) in water:ethanol (1:1, 10 ml) was refluxed for 48 h. The mixture was cooled to room temperature and then basified with aqueous 2N NaOH to pH 10–12. The resulting precipitate was filtered, washed with water, water:ethanol (2:1) and isolated as a brown solid (28 mg, 38%). $^1$H NMR (CDCl$_3$): 8.50–8.47 (m, 2H), 7.99 (d, J=3.0 Hz, 1H), 7.53–7.47 (m, 3H), 7.36 (d, J=9.0 Hz, 1H), 7.29 (s, 1H), 6.91 (s, 1H), 6.71 (dd, J=3.0, 9.0 Hz, 1H), 3.88 (s, 3H).

EXAMPLE 82

4-(2-Chloro-5-methoxyanilino)-2-(2-pyrazinyl)-6-(trifluoromethyl)pyrimidine

The title compound was prepared from a mixture of 4-chloro-2-(2-pyrazinyl)-6-(trifluoromethyl)pyrimidine (50 mg, 0.192 mmol) and 2-chloro-5-methoxyaniline hydrochloride (56 mg, 0.288 mmol) similar to Example 76 and isolated as a tan solid (41 mg, 56%). $^1$H NMR (CDCl$_3$): 9.75 (d, J=1.2 Hz, 1H), 8.79 (dd, J=1.7, 2.6 Hz, 1H), 8.73 (d, J=2.4 Hz, 1H), 7.70 (s, 1H), 7.52 (s, 1H), 7.40 (d, J=9.3 Hz, 1H), 7.04 (s, 1H), 6.78 (dd, J=2.9, 8.9 Hz, 1H), 3.89 (s, 3H).

EXAMPLE 83

4-(3,4-Methylenedioxyanilino)-2-phenyl-6-(trifluoromethyl)pyrimidine

The title compound was prepared from a mixture of 4-chloro-2-phenyl-6-(trifluoromethyl)pyrimidine (50 mg, 0.193 mmol) and 3,4-methylenedioxyaniline (40 mg, 0.290 mmol) similar to Example 77 and isolated as a tan solid (16 mg, 23%). $^1$H NMR (CDCl$_3$): 8.44–8.40 (m, 2H), 7.50–7.45 (m, 3H), 7.02 (s, 1H), 6.91 (s, 1H), 6.85 (d, J=8.1 Hz, 1H), 6.78 (dd, J=2.0, 8.3 Hz, 1H), 6.71 (s, 1H), 6.03 (s, 2H).

EXAMPLE 84

4-(3,4-Methylenedioxyanilino)-2-(2-pyrazinyl)-6-(trifluoromethyl)pyrimidine

The title compound was prepared from a mixture of 4-chloro-2-(2-pyrazinyl)-6-(trifluoromethyl)pyrimidine (50 mg, 0.192 mmol) and 3,4-methylenedioxyaniline (39 mg, 0.288 mmol) similar to Example 76 and isolated as a pink solid (21 mg, 30%). $^1$H NMR (CDCl$_3$): 9.72 (d, J=1.2 Hz, 1H), 8.76 (dd, J=1.5, 2.7 Hz, 1H), 8.71 (d, J=2.7 Hz, 1H), 7.60 (s, 1H), 6.88 (s, 1H), 6.87 (d, J=8.1 Hz, 1H), 6.83 (s, 1H), 6.78 (dd, J=1.8, 8.1 Hz, 1H), 6.05 (s, 2H).

EXAMPLE 85

4-(2-Methoxy-5-phenoxyanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 2-methoxy-5-phenoxyaniline (62 mg, 0.290 mmol) similar to Example 58 and isolated as a tan solid (46 mg, 54%). $^1$H NMR (CDCl$_3$): 9.57 (dd, J=1.1, 2.3 Hz, 1H), 8.67 (dd, J=1.8, 4.8 Hz, 1H), 8.42–8.38 (m, 1H), 8.12 (s, 1H), 7.75 (s, 1H), 7.38–7.31 (m, 2H), 7.25–7.21 (m, 1H), 7.11 (t, J=1.2 Hz, 1H), 7.09–7.03 (m, 2H), 6.91 (d, J=8.7 Hz, 2H), 6.82 (dd, J=2.7, 8.7 Hz, 1H), 3.91 (s, 3H).

EXAMPLE 86

4-[2-Methyl-5-(carboxymethylester)anilino]-2-(3-pyridinyl)-6-(trifluoromethyl)pyrimidine The title compound was prepared from a mixture of 4-chloro-2-(3-pyridinyl)-6-(trifluoromethyl)pyrimidine (50 mg, 0.193 mmol) and 3-amino-4-methylbenzoate (48 mg, 0.290 mmol) similar to Example 58 and isolated as a yellow solid (2 mg, 3%). $^1$H NMR (CDCl$_3$): 9.61 (s, 1H), 8.69–8.65 (m, 2H), 8.22 (s, 1H), 7.90 (dd, J=1.8, 7.8 Hz, 1H), 7.40–7.35 (m, 2H), 7.14 (s, 1H), 6.59 (s, 1H), 3.91 (s, 3H), 2.35 (s, 3H).

EXAMPLE 87

4-(2-Methoxy-5-methylanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 2-methoxy-5-methylaniline (40 mg, 0.290 mmol) similar to Example 58 and isolated as a yellow solid (41 mg, 59%). $^1$H NMR (CDCl$_3$): 9.66 (d, J=1.8 Hz, 1H), 8.74–8.70 (m, 2H), 7.98 (s, 1H), 7.55 (s, 1H), 7.44–7.40 (m, 1H), 6.99–6.95 (m, 1H), 6.88 (s, 1H), 6.85 (s, 1H), 3.89 (s, 3H), 2.40 (s, 3H).

EXAMPLE 88

4-(5-Fluoro-2-methylanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 5-fluoro-2-methylaniline (36 mg, 0.290 mmol) similar to Example 58 and isolated as a tan solid (4 mg, 6%). $^1$H NMR (CDCl$_3$): 9.71 (dd, J=0.80, 2.3 Hz, 1H), 8.74–8.71 (m, 1H), 8.68 (dd, J=1.7, 5.0 Hz, 1H), 7.72 (s, 1H), 7.44–7.39 (m, 1H), 7.33–7.28 (m, 2H), 7.02–6.95 (m, 1H), 6.67 (s, 1H), 2.29 (s, 3H).

EXAMPLE 89

4-(2-Methoxy-5-trifluoromethylanilino)-2-(3-pyridinyl)-6-(trifluoromethyl)pyrimidine The title compound was prepared from a mixture of 4-chloro-2-(3-pyridinyl)-6-(trifluoromethyl)pyrimidine (50 mg, 0.193 mmol) and 3-amino-4-methoxybenzotrifluoride (55 mg, 0.290 mmol) similar to Example 58 and isolated as a yellow solid (56 mg, 70%). $^1$H NMR (CDCl$_3$): 9.66 (dd, J=0.6, 2.1 Hz, 1H), 8.95 (s, 1H), 8.75 (dd, J=1.8, 4.8 Hz, 1H), 8.73–8.69 (m, 1H), 7.67 (s, 1H), 7.46–7.42 (m, 1H), 7.41–7.37 (m, 1H), 7.01 (d, J=8.4 Hz, 1H), 6.93 (s, 1H), 3.99 (s, 3H).

EXAMPLE 90

4-(2-Methyl-5-nitroanilino)-2-(3-pyridinyl)-6-(trifluoromethyl)pyrimidine

A mixture of 4-chloro-2-(3-pyridinyl)-6-(trifluoromethyl)pyrimidine (500 mg, 1.93 mmol), 2-methyl,5-nitroaniline (441 mg, 2.90 mmol), and 2N HCl (1.5 ml) in water:ethanol (1:1, 100 ml) was refluxed for 48 h. The mixture was cooled to room temperature and basified with aqueous 2N NaOH to pH 10–12. The resulting precipitate was filtered, washed with water and water:ethanol (2:1). The product was dried under vacuo and then washed with chloroform to give a yellow solid (136 mg, 19%). $^1$H NMR (DMSO-$d_6$): 9.84 (s, 1H), 9.41 (s, 1H), 8.99 (s, 1H), 8.73 (d, J=4.2 Hz, 1H), 8.57 (d, J=7.8 Hz, 1H), 8.02 (dd, J=1.8, 7.8, 1H), 7.61 (d, J=8.1 Hz, 1H), 7.58–7.54 (m, 1H), 7.39 (s, 1H), 2.45 (s, 3H).

EXAMPLE 91

4-(5-Amino-2-methylanilino)-2-(3-pyridinyl)-6-(trifluoromethyl)pyrimidine hydrochloride To a solution of 4-(2-methyl,5-nitroanilino)-2-(3-pyridinyl)-6-(trifluoromethyl)pyrimidine (75 mg, 0.200 mmol) in anhydrous ethanol (10 ml) was added slowly anhydrous tin chloride (152 mg, 0.800 mmol). The mixture was refluxed for 1 h and then rotary evaporated to leave a brown oil. The brown oil was basified with 2N NaOH to give a final pH of 8. The resulting precipitate was filtered and washed with ethyl acetate. The aqueous phase and organic phase was combined, washed with water (1×20 ml) and dried over anhydrous sodium sulfate. The ethyl acetate was rotary evaporated to dryness to give a dark yellow solid (33 mg, 44%). $^1$H NMR (CDCl$_3$): 9.69–9.68 (m, 1H), 8.73–8.67 (m, 2H), 7.53 (s, 1H), 7.43–7.39 (m, 1H), 7.11 (d, J=8.4 Hz, 1H), 6.72 (s, 1H), 6.64 (d, J=2.7 Hz, 1H), 6.61 (s, 1H), 3.01 (bs, 2H), 2.17 (s, 3H).

EXAMPLE 92

4-(3-Ethoxyanilino)-2-(2-pyridinyl)-6-(trifluoromethyl)pyrimidine

A mixture of 4-chloro-2-(2-pyridinyl)-6-(trifluoromethyl)pyrimidine (25 mg, 0.096 mmol), m-phenetidine (19 μl, 0.144 mmol), and 2N HCl (75 μl) in water:ethanol (2:1, 5 ml) was refluxed for 24 h. The mixture was cooled to room temperature and basified with aqueous 2N NaOH to pH 10–12. The resulting precipitate was filtered, washed with water, water:ethanol (2:1) and dried to give a yellow solid (22 mg, 63%). $^1$H NMR (CDCl$_3$): 8.88–8.85 (m, 1H), 8.58 (d, J=8.1 Hz, 1H), 7.93–7.88 (m, 1H), 7.61 (s, 1H), 7.48–7.44 (m, 1H), 7.35 (t, J=8.4 Hz, 1H), 7.05 (s, 1H), 6.89–6.81 (m, 3H), 4.07 (q, J=7.1 Hz, 2H), 1.45 (t, J=7.1 Hz, 3H).

EXAMPLE 93

4-(3-Ethylanilino)-2-(2-pyridinyl)-6-(trifluoromethyl)pyrimidine

The title compound was prepared from a mixture of 4-chloro-2-(2-pyridinyl)-6-(trifluoromethyl)pyrimidine (25 mg, 0.096 mmol) and 3-ethylaniline (18 μl, 0.144 mmol) similar to Example 92 and isolated as a yellow oil (12 mg, 36%). $^1$H NMR (CDCl$_3$): 8.84–8.82 (m, 1H), 8.57–8.54 (m, 1H), 7.89–7.84 (m, 1H), 7.72 (s, 1H), 7.44–7.40 (m, 1H), 7.34 (d, J=8.7 Hz, 1H), 7.14–7.11 (m, 3H), 7.01 (s, 1H), 2.69 (q, J=7.8 Hz, 2H), 1.27 (t, J=7.8 Hz, 3H).

EXAMPLE 94

4-(5-Methoxy-2-methylanilino)-2-(2-pyridinyl)-6-(trifluoromethyl)pyrimidine

The title compound was prepared from a mixture of 4-chloro-2-(2-pyridinyl)-6-(trifluoromethyl)pyrimidine (25 mg, 0.096 mmol) and 5-methoxy-2-methylaniline (20 mg, 0.144 mmol) similar to Example 92 and isolated as a yellow solid (18 mg, 52%). $^1$H NMR (CDCl$_3$): 8.85–8.82 (m, 1H), 8.59–8.56 (m, 1H), 7.90–7.84 (m, 1H), 7.45–7.40 (m, 2H), 7.24 (d, J=8.1 Hz, 1H), 6.87 (s, 1H), 6.83 (dd, J=2.6, 8.3 Hz, 1H), 6.69 (s, 1H), 3.81 (s, 3H), 2.20 (s, 3H).

EXAMPLE 95

4-(2-Chloro-5-methoxyanilino)-2-(2-pyridinyl)-6-(trifluoromethyl)pyrimidine

The title compound was prepared from a mixture of 4-chloro-2-(2-pyridinyl)-6-(trifluoromethyl)pyrimidine (25 mg, 0.096 mmol) and 2-chloro-5-methoxyaniline (23 mg, 0.144 mmol) similar to Example 92 and isolated as a white solid (11 mg, 48%). $^1$H NMR (CDCl$_3$): 8.84–8.82 (m, 1H), 8.58–8.54 (m, 1H), 7.90–7.85 (m, 1H), 7.66 (s, 1H), 7.60 (s, 1H), 7.46–7.41 (m, 1H), 7.37 (d, J=8.7 Hz, 1H), 7.01 (s, 1H), 6.75 (dd, J=3.0, 8.7 Hz, 1H), 3.88 (s, 3H).

EXAMPLE 96

4-(3-Methylmercaptoanilino)-2-(2-pyridinyl)-6-(trifluoromethyl)pyrimidine

The title compound was prepared from a mixture of 4-chloro-2-(2-pyridinyl)-6-(trifluoromethyl)pyrimidine (25 mg, 0.096 mmol) and 3-(methylmercapto)aniline (18 μl, 0.144 mmol) similar to Example 92 and isolated as a yellow solid (21 mg, 58%). $^1$H NMR (CDCl$_3$): 8.87–8.85 (m, 1H), 8.58 (d, J=7.8 Hz, 1H), 7.93–7.88 (m, 1H), 7.61 (s, 1H), 7.48–7.44 (m, 1H), 7.36 (t, J=7.8 Hz, 1H), 7.25 (s, 1H), 7.17–7.14 (m, 1H), 7.10–7.06 (m, 1H), 7.01 (s, 1H), 2.52 (s, 3H).

EXAMPLE 97

4-(3-Hydroxyanilino)-2-(3-pyridinyl)-6-(trifluoromethyl)pyrimidine hydrochloride The title compound was prepared from a mixture of 4-chloro-2-(3-pyridinyl)-6-(trifluoromethyl)pyrimidine (50 mg, 0.193 mmol), 3-aminophenol (32 mg, 0.290 mmol), and 2N HCl (150 μl) in water:ethanol (2:1, 10 ml) was refluxed for 24 h. The mixture was cooled to room temperature and the resulting crystals was filtered, washed with water, with water:ethanol (2:1) and dried to give a tan crystals (22 mg, 30%). $^1$H NMR (DMSO-$d_6$): 10.17 (s, 1H), 9.36 (d, J=1.5 Hz, 1H), 8.72–8.66 (m, 2H), 7.66–7.62 (m, 1H), 7.20 (s, 1H), 7.10 (d, J=7.8 Hz, 1H), 7.05 (d, J=7.8 Hz, 1H), 7.04 (s, 1H), 7.01 (s, 1H), 6.45–6.41 (m, 1H).

EXAMPLE 98

4-(3-Hydroxyanilino)-2-(2-pyrazinyl)-6-(trifluoromethyl)pyrimidine hydrochloride The title compound was prepared from a mixture of 4-chloro-2-(2-pyrazinyl)-6-(trifluoromethyl)pyrimidine (50 mg, 0.192 mmol) and 3-aminophenol (31 mg, 0.288 mmol) similar to Example 97 and isolated as a tan solid (28 mg,). $^1$H NMR (DMSO-d$_6$): 10.26 (s, 1H), 9.62 (s, 1H), 9.51–9.50 (m, 1H), 8.87–8.83 (m, 2H), 7.30 (s, 1H), 7.23–7.21 (m, 3H), 6.57–6.54 (m, 1H).

EXAMPLE 99

4-(3-Hydroxyanilino)-2-(4-pyridinyl)-6-(trifluoromethyl)pyrimidine hydrochloride The title compound was prepared from a mixture of 4-chloro-2-(4-pyridinyl)-6-(trifluoromethyl)pyrimidine (50 mg, 0.193 mmol), 3-aminophenol (32 mg, 0.290 mmol) similar to Example 97 and isolated as a yellow solid (37 mg, 52%). $^1$H NMR (DMSO-d$_6$): 10.51 (s, 1H), 8.98 (d, J=6.0 Hz, 2H), 8.54 (d, J=6.6 Hz, 2H), 7.32–7.21 (m, 5H), 6.61–6.57 (m, 1H).

EXAMPLE 100

4-(2,4-Dimethoxyanilino)-6-methyl-2-(2-pyridinyl)-pyrimidine hydrochloride

The title compound was prepared from a mixture of 4-chloro-6-methyl-2-(2-pyridinyl)pyrimidine (50 mg, 0.243 mmol) and 2,4-dimethoxyaniline (56 mg, 0.365 mmol) similar to Example 92 and isolated as a purple crystal (52 mg, 64%). $^1$H NMR (CDCl$_3$): 8.84–8.81 (m, 1H), 8.48–8.44 (m, 1H), 7.86–7.80 (m, 1H), 7.60 (d, J=8.4 Hz, 1H), 7.38–7.34 (m, 1H), 6.93 (s, 1H), 6.56–6.53 (m, 2H), 6.46 (s, 1H), 3.84 (d, J=0.6 Hz, 3H), 3.83 (d, J=0.9 Hz, 3H), 2.48 (s, 3H).

EXAMPLE 101

4-(3,5-Dimethoxyanilino)-6-methyl-2-(2-pyridinyl)-pyrimidine hydrochloride

The title compound was prepared from a mixture of 4-chloro-6-methyl-2-(2-pyridinyl)pyrimidine (50 mg, 0.243 mmol) and 3,5-dimethoxyaniline (56 mg, 0.365 mmol) similar to Example 92 and isolated as a tan solid (21 mg, 26%). $^1$H NMR (CDCl$_3$): 8.83–8.81 (m, 1H), 8.49–8.46 (m, 1H), 7.86–7.80 (m, 1H), 7.39–7.35 (m, 1H), 6.99 (s, 1H), 6.70 (s, 1H), 6.53 (d, J=2.4 Hz, 2H), 6.30 (t, J=2.3 Hz, 1H), 3.82 (s, 6H), 2.51 (s, 3H).

EXAMPLE 102

4-(2,5-Diethoxyanilino)-2-(3-pyridinyl)-6-(trifluoromethyl)pyrimidine

A mixture of 4-chloro-2-(3-pyridinyl)-6-(trifluoromethyl)pyrimidine (50 mg, 0.193 mmol), 2,5-diethoxyaniline (52 mg, 0.290 mmol) and 2N HCl (150 μl) in water:ethanol (3:1, 10 ml) was refluxed for 24 h. The mixture was cooled to room temperature and basified with aqueous 2N NaOH to pH 10–12. The resulting precipitate was filtered and isolated as a yellow solid (14 mg, 18%). $^1$H NMR (CDCl$_3$): 9.67 (s, 1H), 8.74–8.71 (m, 2H), 7.93 (s, 1H), 7.64 (s, 1H), 7.43–7.39 (m, 1H), 6.91 (s, 1H), 6.86 (d, J=9.3 Hz, 1H), 6.65 (dd, J=2.7, 8.7 Hz, 1H), 4.13–4.04 (m, 4H), 1.47–1.42 (m, 6H).

EXAMPLE 103

4-(5-Carboxyl-2-methoxyanilino)-2-(3-pyridinyl)-6-(trifluoromethyl)pyrimidine hydrochloride The title compound was prepared from a mixture of 4-chloro-2-(3-pyridinyl)-6-(trifluoromethyl)pyrimidine (50 mg, 0.193 mmol) and 3-amino-4-methoxybenzoic acid (48 mg, 0.290 mmol) similar to Example 92 and isolated as a white solid (50 mg, 64%). $^1$H NMR (DMSO-d$_6$): 9.78 (s, 1H), 9.49–9.48 (m, 1H), 9.08 (s, 1H), 8.74 (dd, J=1.5, 4.8 Hz, 1H), 8.70–8.67 (m, 1H), 7.79 (dd, J=1.5, 4.8 Hz, 1H), 7.56–7.52 (m, 2H), 7.23 (d, J=9.0 Hz, 1H), 3.97 (s, 3H).

EXAMPLE 104

4-(3-Methoxybenzylamino)-2-(3-pyridinyl)-6-(trifluoromethyl)pyrimidine

A mixture of 4-chloro-2-(3-pyridinyl)-6-(trifluoromethyl)pyrimidine (50 mg, 0.193 mmol) and 3-methoxybenzylamine (37 μl, 0.290 mmol) in 10 ml of ethanol was stirred at room temperature for 48 h. The mixture was rotary evaporated to dryness and purified by preparative TLC with hexane:ethyl acetate (3:1) to give a yellow solid (14 mg, 20%). $^1$H NMR (CDCl$_3$): 9.60–9.59 (m, 1H), 8.70–8.66 (m, 2H), 7.40–7.32 (m, 1H), 7.30 (d, J=7.8 Hz, 1H), 6.95 (d, J=7.8 Hz, 1H), 6.91 (s, 1H), 6.85 (dd, J=2.7, 8.4 Hz, 1H), 6.62 (s, 1H), 5.75 (bs, 1H), 4.73 (s, 2H), 3.79 (s, 3H).

EXAMPLE 105

4-(5-Carboxyl-2-hydroxyanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 3-amino-4-hydroxybenzoic acid (44 mg, 0.290 mmol) similar to Example 92 and isolated as a brown solid (25 mg, 34%). $^1$H NMR (DMSO-d$_6$): 9.73 (s, 1H), 9.49 (d, J=1.5 Hz, 1H), 9.07 (s, 1H), 8.74 (dd, J=1.5, 4.5 Hz, 1H), 8.70–8.66 (m, 1H), 7.65 (dd, J=2.4, 8.7 Hz, 1H), 7.56–7.52 (m, 2H), 7.03 (d, J=8.4 Hz, 1H).

EXAMPLE 106

4-(2-Chloro-5-hydroxyanilino)-2-(3-pyridinyl)-6-(trifluoromethyl)pyrimidine a. 2-Chloro-5-hydroxyaniline: To a solution of 4-chloro-3-nitrophenol (1 g, 5.76 mmol) in anhydrous ethanol (20 ml) was slowly added anhydrous tin chloride (4.4 g, 23.2 mmol) at room temperature. The mixture was refluxed for 1 h. The mixture was cooled to room temperature and then rotary evaporated to get an oily liquid. The liquid was basified with aqueous 2N NaOH (20 ml) to a final pH of 8. The resulting precipitate was filtered and washed with water. The aqueous solution was extracted with ethyl acetate (75 ml) and dried over anhydrous sodium sulfate. The ethyl acetate solution was rotary evaporated to dryness to give a pale white solid (584 mg, 71%). $^1$H NMR (CDCl$_3$): 7.07 (d, J=8.4 Hz, 1H), 6.27 (d, J=3.0 Hz, 1H), 6.18 (dd, J=3.0, 9.0 Hz, 1H), 4.64 (s, 1H), 4.02 (bs, 2H).

b. 4-(2-Chloro-5-hydroxyanilino)-2-(3-pyridinyl)-6-(trifluoromethyl)pyrimidine: A mixture of 4-chloro-2-(3-pyridinyl)-6-(trifluoromethyl)pyrimidine (50 mg, 0.193 mmol), 2-chloro-5-hydroxyaniline (42 mg, 0.290 mmol) and 2N HCl (150 μl) in water:ethanol (2:1, 10 ml) was refluxed for 48 h. The mixture was cooled to room temperature, neutralized with aqueous 2N NaOH to a pH of 6–7 and isolated as a yellow solid (6 mg, 8%). $^1$H NMR (DMSO-$d_6$): 9.95 (s, 1H), 9.85 (s, 1H), 9.38–9.37 (m, 1H), 8.74–8.72 (m, 1H), 8.55–8.52 (m, 1H), 7.59–7.54 (m, 1H), 7.37 (dd, J=0.6, 8.7 Hz, 1H), 7.38 (s, 1H), 7.24 (s, 1H), 6.71 (dd, J=2.1, 8.7 Hz, 1H).

EXAMPLE 107

4-(2-Chloro-5-hydroxyanilino)-2-(4-pyridinyl)-6-(trifluoromethyl)pyrimidine

The title compound was prepared from a mixture of 4-chloro-2-(4-pyridinyl)-6-(trifluoromethyl)pyrimidine (50 mg, 0.193 mmol) and 2-chloro-5-hydroxyaniline (42 mg, 0.290 mmol) similar to Example 108 and isolated as a brown solid (3 mg, 4%). $^1$H NMR (CDCl$_3$): 8.68 (dd, J=1.8, 4.5 Hz, 2H), 8.13 (dd, J=1.8, 4.2 Hz, 2H), 7.99 (d, J=2.7 Hz, 1H), 7.34 (s, 1H), 7.33 (d, J=8.7 Hz, 1H), 6.98 (s, 1H), 6.73 (dd, J=2.7, 8.7 Hz, 1H).

EXAMPLE 108

4-(2,6-Dimethylanilino)-6-methyl-2-(2-pyridinyl)pyrimidine

A mixture of 4-chloro-6-methyl-2-(2-pyridinyl)pyrimidine (50 mg, 0.243 mmol), 2,6-dimethylaniline (45 μl, 0.365 mmol) and 2N HCl (150 μl) in water:ethanol (2:1, 10 ml) was refluxed for 24 h. The mixture was cooled to room temperature and basified with aqueous 2N NaOH to pH 10–12. The mixture was extracted with ethyl acetate (75 ml), which was washed with water (2×20 ml), aqueous saturated NaCl (1×20 ml), and dried over anhydrous sodium sulfate. The ethyl acetate solution was rotary evaporated to dryness and the residue was purified by column chromatography to give a yellow oil (58 mg, 82%). $^1$H NMR (CDCl$_3$): 8.81–8.78 (m, 1H), 8.47 (d, J=8.1 Hz, 1H), 7.83–7.77 (m, 1H), 7.36–7.30 (m, 1H), 7.21–7.13 (m, 3H), 6.91 (s, 1H), 5.77 (s, 1H), 2.39 (s, 3H), 2.23 (s, 6H).

EXAMPLE 109

4-(3-Methoxyanilino)-2,6-di(2-pyridinyl)pyrimidine

A mixture 4-chloro-2,6-di(2-pyridinyl)pyrimidine (25 mg, 0.093 mmol), m-anisidine (16 μl, 0.140 mmol) and 2N HCl (75 μl) in water:ethanol (2:1, 10 ml) was refluxed for 24 h. The mixture was cooled to room temperature and basified with aqueous 2N NaOH to pH 10–12. The resulting precipitate was filtered, washed with water and aqueous ethanol to give a yellow solid (20 mg, 60%). $^1$H NMR (CDCl$_3$): 8.87–8.85 (m, 1H), 8.69–8.61 (m, 3H), 7.95 (s, 1H), 7.92–7.84 (m, 2H), 7.44–7.36 (m, 2H), 7.33 (d, J=8.1 Hz, 1H), 7.30 (s, 1H), 7.05 (t, J=2.1 Hz, 1H), 6.98 (dd, J=2.1, 8.1 Hz, 1H), 6.79–6.75 (m, 1H), 3.86 (s, 3H).

EXAMPLE 110

4-(2,5-Dimethoxyanilino)-2,6-di(2-pyridinyl)pyrimidine

The title compound was prepared from a mixture 4-chloro-2,6-di(2-pyridinyl)pyrimidine (25 mg, 0.093 mmol) and 2,5-dimethoxyaniline (21 mg, 0.140 mmol) similar to Example 111 and isolated as a yellow oil (2 mg, 6%). $^1$H NMR (CDCl$_3$): 8.86–8.84 (m, 1H), 8.70–8.64 (m, 3H), 8.11 (s, 1H), 7.92 (s, 1H), 7.91–7.85 (m, 2H), 7.65 (s, 1H), 7.43–7.36 (m, 2H), 6.87 (d, J=9.0 Hz, 1H), 6.61 (dd, J=3.0, 9.0 Hz, 1H), 3.89 (s, 3H), 3.86 (s, 3H).

EXAMPLE 111

4-(5-Methoxy-2-methylanilino)-2,6-di(2-pyridinyl)pyrimidine

The title compound was prepared from a mixture 4-chloro-2,6-di(2-pyridinyl)pyrimidine (25 mg, 0.093 mmol) and 5-methoxy-2-methylaniline (19 mg, 0.140 mmol) similar to Example 111 and isolated as a white solid (21 mg, 61%). $^1$H NMR (CDCl$_3$): 8.88–8.86 (m, 1H), 8.71–8.60 (m, 3H), 7.92–7.83 (m, 2H), 7.62 (s, 1H), 7.44–7.34 (m, 2H), 7.22 (d, J=8.4 Hz, 1H), 7.08 (d, J=2.7 Hz, 1H), 7.06 (s, 1H), 6.78 (dd, J=2.4, 8.4 Hz, 1H), 3.82 (s, 3H), 2.52 (s, 3H).

EXAMPLE 112

4-(2-Methoxy-5-methylanilino)-2,6-di(2-pyridinyl)pyrimidine

The title compound was prepared from a mixture 4-chloro-2,6-di(2-pyridinyl)pyrimidine (25 mg, 0.093 mmol) and 2-methoxy-5-methylaniline (19 mg, 0.140 mmol) similar to Example 111 and isolated as a yellow solid (12 mg, 35%). $^1$H NMR (CDCl$_3$): 8.89–8.87 (m, 1H), 8.69–8.64 (m, 3H), 7.92–7.84 (m, 3H), 7.89 (s, 1H), 7.55 (s, 1H), 7.44–7.36 (m, 2H), 6.92 (dd, J=1.8, 8.1 Hz, 1H), 6.85 (d, J=8.1 Hz, 1H), 3.86 (s, 3H), 2.39 (s, 3H).

EXAMPLE 113

4-(2-Chloro-5-methoxyanilino)-2,6-di(2-pyridinyl)pyrimidine

The title compound was prepared from a mixture of 4-chloro-2,6-di(2-pyridinyl)pyrimidine (25 mg, 0.093 mmol) and 2-chloro-5-methoxyaniline (27 mg, 0.140 mmol) similar to Example 111 and isolated as a white solid (20 mg, 55%). $^1$H NMR (CDCl$_3$): 8.87–8.82 (m, 1H), 8.72–8.64 (m, 3H), 8.08 (d, J=2.7 Hz, 1H), 7.92 (s, 1H), 7.90–7.86 (m, 2H), 7.45–7.38 (m, 3H), 7.33 (d, J=8.7 Hz, 1H), 6.67 (dd, J=3.0, 9.0 Hz, 1H), 3.91 (s, 3H).

EXAMPLE 114

4-(2,5-Dimethylanilino)-2,6-di(2-pyridinyl)pyrimidine

The title compound was prepared from a mixture 4-chloro-2,6-di(2-pyridinyl)pyrimidine (25 mg, 0.093 mmol) and 2,5-dimethylaniline (17 μl, 0.140 mmol) similar to Example 111 and isolated as a yellow oil (7 mg, 21%). $^1$H NMR (CDCl$_3$): 8.88–8.86 (m, 1H), 8.71–8.68 (m, 1H), 8.64–8.58 (m, 2H), 7.92–7.82 (m, 2H), 7.50 (s, 1H), 7.43–7.32 (m, 2H), 7.23 (s, 1H), 7.21 (d, J=7.5 Hz, 1H), 7.09 (s, 1H), 7.04 (dd, J=1.8, 7.8 Hz, 1H), 2.36 (s, 3H), 2.27 (s, 3H).

EXAMPLE 115

4-(2,5-Dimethylanilino)-2-(4-pyridinyl)-6-(trifluoromethyl)pyrimidine hydrochloride A mixture of 4-chloro-2-(4-pyridinyl)-6-(trifluoromethyl)pyrimidine (50 mg, 0.193 mmol), 2,5-dimethylaniline (36 μl, 0.290 mmol) and 2N HCl (150 μl) in water:ethanol (2:1, 10 ml) was refluxed for 24 h. The mixture was cooled to room temperature. The resulting precipitate was filtered, washed with water and aqueous ethanol to give a white solid (28 mg, 42%). $^1$H NMR (CDCl$_3$): 8.77 (dd, J=1.5, 4.5 Hz, 2H), 8.27 (dd, J=1.5, 4.5 Hz, 2H), 7.24 (d, J=7.8 Hz, 1H), 7.18 (s, 1H), 7.11 (dd, J=1.8, 7.8 Hz, 1H), 6.99 (s, 1H), 6.62 (s, 1H), 2.38 (s, 3H), 2.25 (s, 3H).

EXAMPLE 116

4-(2-Methoxy-5-methylamino)-2-(4-pyridinyl)-6-(trifluoromethyl)pyrimidine

The title compound was prepared from a mixture of 4-chloro-2-(4-pyridinyl)-6-(trifluoromethyl)pyrimidine (50 mg, 0.193 mmol) and 2-methoxy-5-methylaniline (40 mg, 0.290 mmol) similar to Example 115 and isolated as a white solid (48 mg, 69%). $^1$H NMR (CDCl$_3$): 8.79 (dd, J=1.8, 4.5 Hz, 2H), 8.30 (dd, J=1.8, 4.5 Hz, 2H), 7.97 (s, 1H), 7.46 (s, 1H), 6.99 (dd, J=1.5, 8.1 Hz, 1H), 6.94 (s, 1H), 6.89 (d, J=8.4 Hz, 1H), 3.90 (s, 3H), 2.41 (s, 3H).

EXAMPLE 117

4-(5-Hydroxy-2-methylanilino)-2-(3-pyridinyl)-6-(trifluoromethyl)pyrimidine

A mixture of 4-chloro-2-(3-pyridinyl)-6-(trifluoromethyl)pyrimidine (50 mg, 0.193 mmol), 5-hydroxy-2-methylaniline (36 mg, 0.290 mmol) and 2N HCl (150 μl) in water:ethanol (2:1, 10 ml) was refluxed for 24 h. The mixture was cooled to room temperature and neutralized with aqueous 2N NaOH to pH 6–7. The mixture was extracted with ethyl acetate (75 ml), washed with water (2×20 ml), aqueous saturated NaCl (1×20 ml) and dried over anhydrous sodium sulfate. The ethyl acetate solution was rotary evaporated to dryness and the residue was purified by column chromatography to give a yellow solid (18 mg, 27%). $^1$H NMR (Acetone-d$_6$): 9.53–9.51 (m, 1H), 8.85 (s, 1H), 8.71 (dd, J=1.8, 4.8 Hz, 1H), 8.67–8.63 (m, 1H), 8.49 (s, 1H), 7.53–7.48 (m, 1H), 7.24 (s, 1H), 7.17 (d, J=8.1 Hz, 1H), 6.98 (s, 1H), 6.75 (dd, J=2.4, 8.4 Hz, 1H), 2.23 (s, 3H).

EXAMPLE 118

4-(5-Hydroxy-2-methylanilino)-2-(4-pyridinyl)-6-(trifluoromethyl)pyrimidine

The title compound was prepared from a mixture of 4-chloro-2-(4-pyridinyl)-6-(trifluoromethyl)pyrimidine (50 mg, 0.193 mmol) and 5-hydroxy-2-methylaniline (36 mg, 0.290 mmol) similar to Example 117 and isolated as a tan solid (19 mg, 28%). $^1$H NMR (Acetone-d$_6$): 8.91 (s, 1H), 8.75 (dd, J=1.2, 4.8 Hz, 2H), 8.55 (s, 1H), 8.22 (dd, J=1.8, 4.8 Hz, 2H), 7.23 (s, 1H), 7.18 (d, J=8.1 Hz, 1H), 7.02 (s, 1H), 6.76 (dd, J=3.0, 8.7 Hz, 1H), 2.23 (s, 3H).

EXAMPLE 119

4-(5-Methoxy-2-piperidino-anilino)-2-(3-pyridinyl)-6-(trifluoromethyl)pyrimidine -(4-Methoxy-2-aminophenyl)piperidine: To a solution of 1-(4-methoxy-2-nitrophenyl)piperidine (238 mg, 1.01 mmol) in anhydrous ethanol (20 ml) was slowly added anhydrous tin chloride (772 mg, 4.07 mmol) at room temperature. The mixture was refluxed for 1 h. The mixture was cooled to room temperature and then rotary evaporated to get an oily liquid. The liquid was basified with aqueous 2N NaOH (20 ml) to a final pH of 10. The resulting precipitate was filtered and washed with water. The aqueous solution was extracted with ethyl acetate (75 ml), washed with water (2×20 ml) and dried over anhydrous sodium sulfate. The ethyl acetate solution was rotary evaporated to give a dark brown liquid (153 mg, 74%). $^1$H NMR (CDCl$_3$): 6.90 (d, J=8.7 Hz, 1H), 6.29 (d, J=2.7 Hz, 1H), 6.26 (dd, J=2.7, 8.1 Hz, 1H), 4.04 (bs, 2H), 3.69 (s, 3H), 2.75 (s, 4H), 1.70–1.63 (m, 4H), 1.54 (s, 2H).

b. 4-(5-Methoxy-2-piperidino-anilino)-2-(3-pyridinyl)-6-(trifluoromethyl)pyrimidine: The title compound was prepared from a mixture of 4-chloro-2-(3-pyridinyl)-6-(trifluoromethyl)pyrimidine (50 mg, 0.193 mmol) and 1-(4-methoxy-2-aminophenyl)piperidine (60 mg, 0.290 mmol) similar to Example 117 and isolated as a green solid (1 mg, 1%). $^1$H NMR (CDCl$_3$): 9.71–9.69 (m, 1H), 8.78–8.74 (m, 2H), 8.70 (s, 1H), 8.18 (s, 1H), 7.46–7.41 (m, 1H), 7.16 (d, J=8.7 Hz, 1H), 6.90 (s, 1H), 6.66 (dd, J=2.7, 8.4 Hz, 1H), 3.90 (s, 3H), 2.83–2.79 (m, 4H), 1.81–1.74 (m, 4H), 1.62 (s, 2H).

EXAMPLE 120

4-(2-Cyano-5-methylanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 2-cyano-5-methylaniline (38 mg, 0.290 mmol) similar to Example 117 and isolated as a yellow solid (8 mg, 12%). $^1$H NMR (CDCl$_3$): 9.62–9.61 (m, 1H), 8.75–8.69 (m, 2H), 8.08 (s, 1H), 7.62 (s, 1H), 7.60 (d, J=8.1 Hz, 1H), 7.46–7.41 (m, 1H), 7.12 (dd, J=0.9, 8.1 Hz, 1H), 7.00 (s, 1H), 2.52 (s, 3H).

EXAMPLE 121

4-(3,5-Dimethylanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 3,5-dimethylaniline (36 μl, 0.290 mmol) similar to Example 117 and isolated as a yellow solid (26 mg, 39%). $^1$H NMR (CDCl$_3$): 9.66–9.64 (m, 1H), 8.73 (s, 1H), 8.72–8.69 (m, 1H), 7.44–7.40 (m, 1H), 7.30 (s, 1H), 7.04 (s, 2H), 6.93 (s, 1H), 6.90 (s, 1H), 2.38 (s, 3H), 2.37 (s, 3H).

EXAMPLE 122

4-(3,5-Dimethoxyanilino)-2-(3-pyridinyl)-6-(trifluoromethyl)pyrimidine hydrochloride The title compound was prepared from a mixture of 4-chloro-2-(3-pyridinyl)-6-(trifluoromethyl)pyrimidine (50 mg, 0.193 mmol) and 3,5-dimethoxyaniline (44 mg, 0.290 mmol) similar to Example 117 and isolated as a yellow solid (29 mg, 38%). $^1$H NMR (DMSO-d$_6$): 10.32 (s, 1H), 9.48–9.46 (m, 1H), 8.76–8.74 (m, 1H), 8.62–8.58 (m, 1H), 7.63–7.58 (m, 1H), 7.14 (s, 1H), 7.06 (s, 2H), 6.32 (s, 1H), 3.80 (s, 6H).

EXAMPLE 123

4-(2-Chloro-5-methylanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 2-chloro-5-methylaniline (41 mg, 0.290 mmol) similar to Example 117 and isolated as a yellow solid (15 mg, 21%). $^1$H NMR (CDCl$_3$): 9.62–9.61 (m, 1H), 8.73–8.69 (m, 2H), 7.89 (s, 1H), 7.44–7.40 (m, 1H), 7.37 (d, J=8.1 Hz, 1H), 7.30 (s, 1H), 7.00 (dd, J=0.9, 8.4 Hz, 1H), 6.88 (s, 1H), 2.42 (s, 3H).

EXAMPLE 124

4-(3-Methoxy-5-trifluoromethylanilino)-2-(3-pyridinyl)-6-(trifluoromethyl)pyrimidine The title compound was prepared from a mixture of 4-chloro-2-(3-pyridinyl)-6-(trifluoromethyl)pyrimidine (50 mg, 0.193 mmol) and 3-methoxy-5-trifluoromethylaniline (55 mg, 0.290 mmol) similar to Example 117 and isolated as a yellow solid (27 mg, 34%). $^1$H NMR (CDCl$_3$): 9.65–9.64 (m, 1H), 8.75–8.70 (m, 2H), 7.46–7.41 (m, 2H), 7.36 (s, 1H), 7.31 (s, 1H), 7.00 (s, 1H), 6.93 (s, 1H), 3.91 (s, 3H).

EXAMPLE 125

4-(2-Chloro-5-methoxyanilino)-2-[6-(trifluoromethyl)-3-pyridinyl]-6-(trifluoromethyl)pyrimidine 4-Hydroxy-6-Trifluoromethyl-2-(6-trifluoromethyl-3-pyridinyl)pyrimidine: A mixture of 6-(trifluoromethyl)pyridine-3-amidine (1 g, 5.26 mmol) and ethyl 4,4,4-trifluoro-2-butynoate (1.1 ml, 7.89 mmol) in ethanol (100 ml) was stirred at 0° C. for 20 min. The temperature of the mixture was raised to 60° C. and was let to stir at this temperature for 30 min. Then aqueous KOH (0.86 g in 20 ml water) was added dropwise. The mixture was refluxed for 4 h. The mixture was cooled to room temperature, rotary evaporated and isolated as a white solid (1.5 g, 94%). $^1$H NMR (CDCl$_3$): 9.72 (d, J=2.4 Hz, 1H), 8.87 (dd, J=2.1, 8.7 Hz, 1H), 7.93 (d, J=8.1 Hz, 1H), 7.00 (s, 1H).

4-Chloro-2-[6-(trifluoromethyl)-3-pyridinyl]-6-(trifluoromethyl)pyrimidine: A mixture of 4-hydroxy-6-trifluoromethyl-2-(6-trifluoromethyl-3-pyridinyl)-pyrimidine (145 mg, 0.469 mmol) and phosphorus oxychloride (10 ml) was refluxed for 3 h. The mixture was cooled to room temperature and rotary evaporated to leave an oily residue. The residue was extracted with ethyl acetate (50 ml), washed with water (2×20 ml) and dried over anhydrous sodium sulfate. The ethyl acetate solution was concentrated in vacuo to give a crude solid (80 mg).

4-(2-Chloro-5-methoxyanilino)-2-[6-(trifluoromethyl)-3-pyridinyl]-6-(trifluoromethyl)pyrimidine: A mixture of crude 4-chloro-2-[6-(trifluoromethyl)-3-pyridinyl]-6-(trifluoromethyl)pyrimidine (50 mg, 0.152 mmol), 2-chloro-5-methoxyaniline (50 mg, 0.229 mmol) and 2N HCl (150 μl) in water:ethanol (2:1, 10 ml) was refluxed for 120 h. The mixture was cooled to room temperature and basified with aqueous 2N NaOH to pH 10–12. The mixture was extracted with ethyl acetate (75 ml), washed with water (2×20 ml), with aqueous saturated NaCl (1×20 ml) and dried over anhydrous sodium sulfate. The ethyl acetate solution was rotary evaporated to dryness and the residue was purified by preparative TLC to give a white solid (3 mg, 4%). $^1$H NMR (CDCl$_3$): 9.72 (s, 1H), 8.90 (dd, J=3.0, 7.8 Hz, 1H), 7.81 (d, J=8.1 Hz, 1H), 7.75 (s, 1H), 7.40 (d, J=9.3 Hz, 1H), 7.36 (s, 1H), 6.99 (s, 1H), 6.75 (dd, J=3.0, 8.7 Hz, 1H), 3.86 (s, 3H).

EXAMPLE 126

4-(5-Bromo-2-methoxyanilino)-2-(3-pyridinyl)-6-(trifluoromethyl)pyrimidine a. 5-Bromo-2-methoxyaniline: To a solution of 4-bromo-2-nitroanisole (500 mg, 2.15 mmol) in anhydrous ethanol (15 ml) was added slowly anhydrous tin chloride (1.6 g, 8.62 mmol). The mixture was refluxed for 1 h, then rotary evaporated to leave a brown oil which was neutralized with aqueous 2N NaOH (5 ml). The resulting solid was filtered and washed with ethyl acetate. The aqueous and ethyl acetate solutions were combined and washed with water. The ethyl acetate solution was rotary evaporated to dryness and the residue was purified column chromatography to give a white solid (46 mg, 11%). $^1$H NMR (CDCl$_3$): 6.79 (dd, J=2.1, 9.0 Hz, 1H), 6.80 (d, J=1.8 Hz, 1H), 6.61 (d, J=9.3 Hz, 1H), 3.84 (s, 2H), 3.80 (s, 3H).

b. 4-(5-Bromo-2-methoxyanilino)-2-(3-pyridinyl)-6-(trifluoromethyl)pyrimidine: The title compound was prepared from a mixture of 4-chloro-2-(3-pyridinyl)-6-(trifluoromethyl)pyrimidine (50 mg, 0.193 mmol) and 5-bromo-2-methoxyaniline (39 mg, 0.193 mmol) similar to Example 117 and isolated as a tan solid (26 mg, 32%). $^1$H NMR (CDCl$_3$): 9.67–9.66 (m, 1H), 8.77–8.71 (m, 3H), 7.55 (s, 1H), 7.48–7.43 (m, 1H), 7.24 (dd, J=2.4, 8.7 Hz, 1H), 6.92 (s, 1H), 6.83 (d, J=9.0 Hz, 1H), 3.93 (s, 3H).

EXAMPLE 127

4-(2-Bromo-5-methoxyanilino)-2-(3-pyridinyl)-6-(trifluoromethyl)pyrimidine a. 2-Bromo-5-methoxyaniline: The title compound was prepared from 4-bromo-3-nitroanisole (490 mg, 2.11 mmol), anhydrous ethanol (15 ml) and anhydrous tin chloride (1.6 g, 8.44 mmol) similar to Example 126a and isolated as a white solid (42 mg, 10%). $^1$H NMR (CDCl$_3$): 7.26 (d, J=8.7 Hz, 1H), 6.31 (d, J=3.0 Hz, 1H), 6.22 (dd, J=2.7, 9.0 Hz, 1H), 4.06 (s, 2H), 3.73 (s, 3H).

b. 4-(2-Bromo-5-methoxyanilino)-2-(3-pyridinyl)-6-(trifluoromethyl)pyrimidine: The title compound was prepared from a mixture of 4-chloro-2-(3-pyridinyl)-6-(trifluoromethyl)pyrimidine (50 mg, 0.193 mmol) and 2-bromo-5-methoxyaniline (39 mg, 0.193 mmol) similar to Example 117 and isolated as a yellow solid (2 mg, 2%). $^1$H NMR (CDCl$_3$): 9.66 (s, 1H), 8.74–8.71 (m, 2H), 7.80 (s, 1H), 7.53 (d, J=9.0 Hz, 1H), 7.48 (s, 1H), 7.45–7.41 (m, 1H), 6.93 (s, 1H), 6.69 (dd, J=3.0, 8.7 Hz, 1H), 3.87 (s, 3H).

EXAMPLE 128

4-[3-Methyl-5-(trifluoromethyl)anilino]-2-(3-pyridinyl)-6-(trifluoromethyl)pyrimidine The title compound was prepared from a mixture of 4-chloro-2-(3-pyridinyl)-6-(trifluoromethyl)pyrimidine (50 mg, 0.193 mmol) and 3-methyl-5-(trifluoromethyl)aniline (51 mg, 0.290 mmol) similar to Example 117 and isolated as a yellow solid (60 mg, 78%). $^1$H NMR (DMSO-$d_6$): 10.60 (s, 1H), 9.45–9.44 (m, 1H), 8.77–8.75 (m, 1H), 8.60–8.56 (m, 1H), 8.30 (s, 1H), 7.68 (s, 1H), 7.62–7.58 (m, 1H), 7.32 (s, 1H), 7.16 (s, 1H), 2.45 (s, 3H).

EXAMPLE 129

4-(5-Chloro-2-hydroxyanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 5-chloro-2-hydroxyaniline (42 mg, 0.290 mmol) similar to Example 117 and isolated as a tan solid (38 mg, 54%). $^1$H NMR (DMSO-$d_6$): 10.44 (s, 1H), 9.74 (s, 1H), 9.42 (s, 1H), 8.75–8.74 (m, 1H), 8.58–8.54 (m, 1H), 8.29 (s, 1H), 7.48 (s, 1H), 7.61–7.57 (m, 1H), 7.08 (dd, J=2.1, 8.7 Hz, 1H), 6.96 (d, J=9.0 Hz, 1H).

EXAMPLE 130

4-(4-Chloro-2,5-dimethoxyanilino)-2-(3-pyridinyl)-6-(trifluoromethyl)pyrimidine hydrochloride The title compound was prepared from a mixture of 4-chloro-2-(3-pyridinyl)-6-(trifluoromethyl)pyrimidine (50 mg, 0.193 mmol) and 4-chloro-2,5-dimethoxyaniline (54 mg, 0.290 mmol) similar to Example 117 and isolated as a brown solid (52 mg, 63%). $^1$H NMR (CDCl$_3$): 9.66–9.64 (m, 1H), 8.76–8.71 (m, 2H), 8.35 (s, 1H), 7.54 (s, 1H), 7.45–7.41 (m, 1H), 7.01 (s, 1H), 6.92 (s, 1H).

EXAMPLE 131

4-(6-Chloro-3-methoxyanilino)-2-morpholino-6-(methyl)pyrimidine

The title compound was prepared from a mixture of 4-(4-chloro-6-methyl-pyrimidin-2-yl)-morpholine (23 mg, 0.108 mmol) and 6-chloro-m-anisidine (31 mg, 0.161 mmol) similar to Example 117 and isolated as a white solid (11 mg, 31%). $^1$H NMR (CDCl$_3$): 8.27 (d, J=3.0 Hz, 1H), 7.91 (s, 1H), 7.27 (d, J=9.0 Hz, 1H), 6.97 (s, 1H), 6.54 (dd, J=3.0, 8.7 Hz, 1H), 3.80 (s, 3H), 3.77 (s, 8H), 2.14 (s, 3H).

EXAMPLE 132

4-(2,4-Dichloro-5-methoxyanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 2,4-dichloro-5-methoxyaniline (44 mg, 0.232 mmol) similar to Example 117 and isolated as a brown solid (9 mg, 11%). $^1$H NMR (CDCl$_3$): 9.64–9.63 (m, 1H), 8.76–8.70 (m, 2H), 8.12 (s, 1H), 7.49 (s, 1H), 7.46–7.41 (m, 2H), 6.95 (s, 1H), 4.00 (s, 3H).

EXAMPLE 133

4-(Indol-4-ylamino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 4-aminoindole (38 mg, 0.290 mmol) similar to Example 117 and isolated as a tan solid (6 mg, 9%). $^1$H NMR (CDCl$_3$): 9.75–9.74 (m, 1H), 8.77–8.73 (m, 1H), 8.69 (dd, J=1.8, 5.1 Hz, 1H), 8.57 (s, 1H), 8.08 (s, 1H), 7.44–7.38 (m, 2H), 7.31–7.23 (m, 3H), 6.85 (s, 1H), 6.50–6.48 (m, 1H).

EXAMPLE 134

4-(2-Acetyl-4,5-dimethoxyanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 2-amino-4,5-dimethoxyacetophenone (56 mg, 0.290 mmol) similar to Example 117 and isolated as a tan solid (24 mg, 30%). $^1$H NMR (CDCl$_3$): 12.49 (s, 1H), 9.65–9.64 (m, 1H), 8.86 (s, 1H), 8.74–8.70 (m, 2H), 7.45–7.41 (m, 1H), 7.35 (s, 1H), 6.99 (s, 1H), 4.12 (s, 3H), 3.95 (s, 3H), 2.68 (s, 3H).

EXAMPLE 135

4-(2-Methyl-5-nitroanilino)-2-(4-pyridinyl)-6-(trifluoromethyl)pyrimidine

A mixture of 4-chloro-2-(4-pyridinyl)-6-(trifluoromethyl)pyrimidine (1 g, 3.90 mmol), 2-methyl-5-nitroaniline (890 mg, 5.90 mmol), and 2N HCl (3 ml) in water:ethanol (1:1, 200 ml) was refluxed for 48 h. The mixture was cooled to room temperature and basified with aqueous 2N NaOH to pH 10–12. The mixture was extracted with ethyl acetate (200 ml), washed with water (2×100 ml), with aqueous saturated NaCl (1×100 ml) and dried over anhydrous sodium sulfate. The ethyl acetate solution was rotary evaporated to dryness to give a tan solid (377 mg, 30%). $^1$H NMR (CDCl$_3$): 8.90 (s, 1H), 8.80 (dd, J=1.8, 4.8 Hz, 2H), 8.30 (dd, J=1.5, 4.5 Hz, 2H), 8.09 (dd, J 2.4, 8.1 Hz, 1H), 7.51 (d, J=8.4 Hz, 1H), 6.99 (s, 1H), 6.87 (s, 1H), 2.47 (s, 3H).

EXAMPLE 136

4-(5-Amino-2-methylanilino)-2-(4-pyridinyl)-6-(trifluoromethyl)pyrimidine

To a solution of 4-(2-methyl,5-nitroanilino)-2-(4-pyridinyl)-6-(trifluoromethyl)pyrimidine (377 mg, 1.00 mmol) in anhydrous ethanol (20 ml) was added slowly anhydrous tin chloride (758 mg, 4.00 mmol). The mixture was refluxed for 1 h and then rotary evaporated to leave a brown oil. The brown oil was basified with aqueous 2N NaOH to give a final pH of 8. The resulting precipitate was filtered and washed with ethyl acetate. The aqueous phase and organic phase was combined and washed with water (1×20 ml) and dried over anhydrous sodium sulfate. The ethyl acetate solution was rotary evaporated to dryness to give a brown solid (212 mg, 57%). $^1$H NMR (CDCl$_3$): 8.76 (dd, J=1.8, 4.8 Hz, 2H), 8.26 (dd, J=1.8, 4.8 Hz, 2H), 7.11 (d, J=7.8 Hz, 1H), 7.12 (s, 1H), 6.69 (d, J=2.4 Hz, 1H), 6.66 (s, 1H), 6.63 (dd, J=2.4, 8.1 Hz, 1H), 3.72 (bs, 2H), 2.16 (s, 3H).

EXAMPLE 137

N-[4-Methyl-3-(2-pyridin-3-yl-6-(trifluoromethyl)pyrimidin-4-ylamino)-phenyl]benzamide A mixture of 4-(5-amino-2-methylanilino)-2-(3-pyridinyl)-6-(trifluoromethyl)pyrimidine hydrochloride (25 mg, 0.067 mmol), benzoic acid (10 mg, 0.080 mmol), and 1-ethyl-3-(3-dimethylaminopropyl)carbodiimide hydrochloride (15.4 mg, 0.080 mmol) in dichloromethane (5 ml) was stirred at room temperature for 24 h. The mixture was rotary evaporated to dryness and the residue was purified by column chromatography to give a white solid (14 mg, 47%). $^1$H NMR (CDCl$_3$): 9.66 (s, 1H), 8.75–8.71 (m, 1H), 8.67 (bs, 1H), 8.40 (s, 1H), 8.08 (dd, J=1.2, 8.4 Hz, 1H), 7.93 (d, J=1.8 Hz, 1H), 7.90–7.86 (m, 2H), 7.81 (s, 1H), 7.55–7.38 (m, 4H), 7.25 (d, J=8.4 Hz, 1H), 6.71 (s, 1H), 2.23 (s, 3H).

EXAMPLE 138

4-(2,5-Diethoxy-4-morpholinoanilino)-2-(3-pyridinyl)-6-(trifluoromethyl)pyrimidine The title compound was prepared from a mixture of 4-chloro-2-(3-pyridinyl)-6-(trifluoromethyl)pyrimidine (50 mg, 0.193 mmol) and 2,5-diethoxy-4-morpholinoaniline dihydrochloride (98 mg, 0.290 mmol) similar to Example 117 and isolated as a brown oil (3 mg, 3%). $^1$H NMR (CDCl$_3$): 9.64–9.63 (m, 1H), 8.74–8.69 (m, 2H), 7.42–7.38 (m, 1H), 7.33 (s, 1H), 6.83 (s, 1H), 6.60 (s, 1H), 4.13 (q, J=7.2 Hz, 4H), 3.92–3.89 (m, 4H), 3.14–3.11 (m, 4H), 1.26 (t, J=7.2 Hz, 6H).

EXAMPLE 139

4-Methyl-N-[4-methyl-3-(2-pyridin-4-yl-6-(trifluoromethyl)pyrimidin-4-ylamino)-phenyl]benzamide A mixture of 4-(5-amino-2-methylanilino)-2-(4-pyridinyl)-6-(trifluoromethyl)pyrimidine (20 mg, 0.058 mmol) and p-toluoyl chloride in pyridine (5 ml) was stirred at room temperature for 15 h. Then water was added to the mixture. The resulting precipitate was filtered, washed with excess water and dried to give a tan solid (26 mg, 94%). $^1$H NMR (CDCl$_3$): 8.77 (dd, J=1.8, 4.5 Hz, 2H), 8.29 (dd, J=1.8, 4.5 Hz, 2H), 8.00 (s, 1H), 7.83 (s, 1H), 7.78 (d, J=8.1 Hz, 2H), 7.38 (dd, J=2.1, 8.4 Hz, 1H), 7.34 (s, 1H), 7.31 (d, J=7.5 Hz, 2H), 7.01 (s, 1H), 6.73 (s, 1H), 2.44 (s, 3H), 2.29 (s, 3H).

EXAMPLE 140

N-[4-Methyl-3-(2-pyridin-4-yl-6-(trifluoromethyl)pyrimidin-4-ylamino)-phenyl]nicotinamide The title compound was prepared from a mixture of 4-(5-amino-2-methylanilino)-2-(4-pyridinyl)-6-(trifluoromethyl)pyrimidine (20 mg, 0.058 mmol) and nicotinoyl chloride hydrochloride (10 mg, 0.058 mmol) similar to Example 139 and isolated as a tan solid (13 mg, 47%). $^1$H NMR (DMSO-d$_6$): 10.50 (s, 1H), 9.85 (s, 1H), 9.12 (d, J=1.5 Hz, 1H), 8.77 (dd, J=1.5, 4.5 Hz, 1H), 8.72 (d, J=5.7 Hz, 2H), 8.34–8.28 (m, 1H), 8.21 (bs, 1H), 8.16 (d, J=6.0 Hz, 2H), 7.60–7.53 (m, 2H), 7.34 (d, J=8.1 Hz, 1H), 7.14 (s, 1H), 2.25 (s, 3H).

EXAMPLE 141

6-Chloro-N-[4-methyl-3-(2-pyridin-4-yl-6-(trifluoromethyl)pyrimidin-4-ylamino)-phenyl]nicotinamide The title compound was prepared from a mixture of 4-(5-amino-2-methylanilino)-2-(4-pyridinyl)-6-(trifluoromethyl)pyrimidine (20 mg, 0.058 mmol) and 6-chloronicotinyl chloride (10 mg, 0.058 mmol) similar to Example 139 and isolated as a white solid (14 mg, 50%). $^1$H NMR (CDCl$_3$): 8.88–8.87 (m, 1H), 8.77 (dd, J=1.8, 4.5 Hz, 2H), 8.29 (dd, J=1.8, 4.5 Hz, 2H), 8.19 (dd, J=2.4, 8.4 Hz, 1H), 8.00 (s, 1H), 7.87 (s, 1H), 7.49 (dd, J=0.9, 8.4 Hz, 1H), 7.36 (s, 1H), 7.35 (s, 1H), 7.01 (s, 1H), 6.76 (s, 1H), 2.32 (s, 3H).

EXAMPLE 142

N-[4-Methyl-3-(2-pyridin-4-yl-6-(trifluoromethyl)pyrimidin-4-ylamino)-phenyl]-4-morpholino-benzamide The title compound was prepared from a mixture of 4-(5-amino-2-methylanilino)-2-(4-pyridinyl)-6-(trifluoromethyl)pyrimidine (10 mg, 0.029 mmol) and 4-morpholinobenzoic acid (7 mg, 0.035 mmol) similar to Example 136 and isolated as a white solid (4 mg, 26%). $^1$H NMR (CDCl$_3$): 8.76 (dd, J=1.8, 4.2 Hz, 2H), 8.29 (dd, J=1.8, 4.2 Hz, 2H), 7.99 (s, 1H), 7.95 (s, 1H), 7.82 (d, J=9.0 Hz, 2H), 7.37 (dd, J=1.8, 8.1 Hz, 1H), 7.31 (d, J=8.7 Hz, 1H), 7.07 (s, 1H), 6.93 (d, J=9.0 Hz, 2H), 6.73 (s, 1H), 3.89–3.86 (m, 4H), 3.31–3.28 (m, 4H), 2.28 (s, 3H).

EXAMPLE 143

4-Chloro-N-[4-methyl-3-(2-pyridin-4-yl-6-(trifluoromethyl)pyrimidin-4-ylamino)-phenyl]benzamide The title compound was prepared from a mixture of 4-(5-amino-2-methylanilino)-2-(4-pyridinyl)-6-(trifluoromethyl)pyrimidine (10 mg, 0.029 mmol) and 4-chlorobenzoyl chloride (6 mg, 0.035 mmol) similar to Example 139 and isolated as a white solid (7 mg, 50%). $^1$H NMR (CDCl$_3$): 8.77 (d, J=6.0 Hz, 2H), 8.29 (d, J=6.0 Hz, 2H), 8.00 (s, 1H), 7.83 (d, J=8.7 Hz, 2H), 7.81 (s, 1H), 7.49 (d, J=8.4 Hz, 2H), 7.35 (s, 2H), 7.01 (s, 1H), 6.75 (s, 1H), 2.30 (2, 3H).

EXAMPLE 144

4-Methoxy-N-[4-methyl-3-(2-pyridin-4-yl-6-(trifluoromethyl)pyrimidin-4-ylamino)-phenyl]benzamide The title compound was prepared from a mixture of 4-(5-amino-2-methylanilino)-2-(4-pyridinyl)-6-(trifluoromethyl)pyrimidine (10 mg, 0.029 mmol) and p-anisoyl chloride (6 mg, 0.035 mmol) similar to Example 139 and isolated as a tan solid (10 mg, 71%). $^1$H NMR (CDCl$_3$): 8.77 (dd, J=1.5, 4.8 Hz, 2H), 8.29 (dd, J=1.5, 4.8 Hz, 2H), 7.99 (s, 1H), 7.86 (d, J=8.7 Hz, 2H), 7.79 (s, 1H), 7.36 (dd, J=1.8, 8.4 Hz, 1H), 7.32 (d, J=8.7 Hz, 2H), 7.02 (s, 1H), 6.99 (d, J=8.7 Hz, 2H), 3.88 (s, 3H), 2.29 (s, 3H).

EXAMPLE 145

4-Chloromethyl-N-[4-methyl-3-(2-pyridin-4-yl-6-(trifluoromethyl)pyrimidin-4-ylamino)-phenyl]benzamide The title compound was prepared from a mixture of 4-(5-amino-2-methylanilino)-2-(4-pyridinyl)-6-(trifluoromethyl)pyrimidine (80 mg, 0.232 mmol) and 4-chloromethylbenzoyl chloride (53 mg, 0.278 mmol) similar to Example 139 and isolated as a yellow solid (55 mg, 48%). $^1$H NMR (CDCl$_3$): 8.75 (dd, J=1.8, 4.8 Hz, 2H), 8.29 (dd, J=1.8, 4.8 Hz, 2H), 8.02 (s, 1H), 7.96 (s, 1H), 7.88 (d, J=8.4 Hz, 2H), 7.51 (d, J=8.4 Hz, 2H), 7.37 (dd, J=1.8, 7.5 Hz, 1H), 7.32 (d, J=7.5 Hz, 1H), 7.12 (s, 1H), 6.75 (s, 1H), 4.63 (s, 2H), 2.28 (s, 3H).

EXAMPLE 146

4-(4-Methyl-piperazin-1-ylmethyl)-N-[4-methyl-3-(2-pyridin-4-yl-6-(trifluoromethyl)pyrimidin-4-ylamino)-phenyl]benzamide To a stirring mixture of 4-chloromethyl-N-[4-methyl-3-(2-pyridin-4-yl-6-(trifluoromethyl)pyrimidin-4-ylamino)-phenyl]benzamide (48 mg, 0.096 mmol) and 1-methylpiperazine (16 pl, 0.0.144 mmol) in anhydrous tetrahydrofuran (5 ml) was added N,N-diisopropylethylamine (200 μl). The mixture was refluxed for 20 h. The mixture was cooled to room temperature and then rotary evaporated to dryness. The residue was purified by column chromatography and isolated as a tan solid (22 mg, 41%). $^1$H NMR (CDCl$_3$): 8.77 (dd, J=1.8, 4.5 Hz, 2H), 8.29 (dd, J=1.5, 4.5 Hz, 2H), 8.01 (s, 1H), 7.85 (s, 1H), 7.83 (d, J=8.1 Hz, 2H), 7.47 (d, J=1.8 Hz, 2H), 7.37 (dd, J=1.5, 8.4 Hz, 1H), 7.33 (d, J=8.4 Hz, 1H), 7.04 (s, 1H), 6.74 (s, 1H), 3.57 (s, 2H), 2.47 (s, 8H), 2.29 (s, 6H).

EXAMPLE 147

4-(2,5-Dimethyl-4-hydroxyanilino)-2-(2-pyridinyl)-6-(trifluoromethyl)pyrimidine hydrochloride The title compound was prepared from a mixture of 4-chloro-2-(2-pyridinyl)-6-(trifluoromethyl)pyrimidine (50 mg, 0.193 mmol) and 4-amino-2,5-dimethylphenol (40 mg, 0.290 mmol) similar to Example 117 and isolated as an orange solid (35 mg, 47%). $^1$H NMR (CDCl$_3$): 8.79–8.77 (m, 1H), 8.58 (d, J=7.8 Hz, 1H), 8.14 (bs, 1H), 7.91–7.86 (m, 1H), 7.46–7.42 (m, 1H), 7.09 (bs, 1H), 6.92 (s, 1H), 6.83 (s, 1H), 6.46 (s, 1H), 2.22 (s, 3H), 2.02 (s, 3H).

EXAMPLE 148

4-(2,5-Dimethyl-4-hydroxyanilino)-(2-pyrazinyl)-6-(trifluoromethyl)pyrimidine hydrochloride The title compound was prepared from a mixture of 4-chloro-(2-pyrazinyl)-6-(trifluoromethyl)pyrimidine (50 mg, 0.191 mmol) and 4-amino-2,5-dimethylphenol (39 mg, 0.287 mmol) similar to Example 117 and isolated as an orange solid (35 mg, 47%). $^1$H NMR (CDCl$_3$): 9.75 (d, J=1.2 Hz, 1H), 8.79–8.78 (m, 1H), 8.73 (d, J=2.4 Hz, 1H), 7.20 (s, 1H), 7.01 (s, 1H), 6.78 (s, 1H), 6.52 (s, 1H), 5.43 (s, 1H), 2.25 (s, 3H), 2.16 (s, 3H).

EXAMPLE 149

4-(2,5-Dimethyl-4-hydroxyanilino)-2-(4-pyridinyl)-6-(trifluoromethyl)pyrimidine

The title compound was prepared from a mixture of 4-chloro-2-(4-pyridinyl)-6-(trifluoromethyl)pyrimidine (50 mg, 0.193 mmol) and 4-amino-2,5-dimethylphenol (40 mg, 0.290 mmol) similar to Example 117 and isolated as a white solid (2 mg). $^1$H NMR (CDCl$_3$): 8.77 (d, J=6.0 Hz, 2H), 8.27 (d, J=6.3 Hz, 2H), 7.05 (s, 1H), 6.86 (s, 1H), 6.77 (s, 1H), 6.47 (s, 1H), 5.25 (bs, 1H), 2.26 (s, 3H), 2.19 (s, 3H).

EXAMPLE 150

4-(4-Chloro-2,5-dimethoxyanilino)-2-(2-pyridinyl)-6-(trifluoromethyl)pyrimidine hydrochloride The title compound was prepared from a mixture of 4-chloro-2-(2-pyridinyl)-6-(trifluoromethyl)pyrimidine (50 mg, 0.193 mmol) and 4-chloro-2,5-dimethoxyaniline (54 mg, 0.290 mmol) similar to Example 117 and isolated as a brown solid (58 mg, 73%). $^1$H NMR (CDCl$_3$): 8.84–8.82 (m, 1H), 8.61–8.57 (m, 1H), 7.93–7.87 (m, 1H), 8.50 (bs, 1H), 7.66 (s, 1H), 7.49–7.45 (m, 1H), 7.02 (s, 1H), 7.01 (s, 1H), 4.07 (s, 3H), 3.92 (s, 3H).

EXAMPLE 151

4-(4-Chloro-2,5-dimethoxyanilino)-(2-pyrazinyl)-6-(trifluoromethyl)pyrimidine hydrochloride The title compound was prepared from a mixture of 4-chloro-(2-pyrazinyl)-6-(trifluoromethyl)pyrimidine (50 mg, 0.191 mmol) and 4-chloro-2,5-dimethoxyaniline (54 mg, 0.287 mmol) similar to Example 117 and isolated as a yellow solid (67 mg, 85%). $^1$H NMR (CDCl$_3$): 9.77 (d, J=1.5 Hz, 1H), 8.79–8.78 (m, 1H), 8.76 (d, J=2.4 Hz, 1H), 8.50 (bs, 1H), 7.70 (s, 1H), 7.05 (s, 1H), 7.04 (s, 1H), 4.06 (s, 3H), 3.93 (s, 3H).

EXAMPLE 152

4-(4,5-Dimethoxy-2-methylanilino)-2-(2-pyridinyl)-6-(trifluoromethyl)pyrimidine hydrochloride The title compound was prepared from a mixture of 4-chloro-2-(2-pyridinyl)-6-(trifluoromethyl)pyrimidine (50 mg, 0.193 mmol) and 4,5-dimethoxy-2-methylaniline (48 mg, 0.290 mmol) similar to Example 117 and isolated as a yellow solid (64 mg, 79%). $^1$H NMR (CDCl$_3$): 8.82–8.80 (m, 1H), 8.55 (d, J=7.8 Hz, 1H), 7.88–7.82 (m, 1H), 7.51 (s, 1H), 7.43–7.38 (m, 1H), 6.80 (s, 1H), 6.76 (s, 1H), 6.50 (s, 1H), 3.92 (s, 3H), 3.84 (s, 3H), 2.19 (s, 3H).

EXAMPLE 153

4-(4,5-Dimethoxy-2-methylanilino)-2-(2-pyrazinyl)-6-(trifluoromethyl)pyrimidine hydrochloride The title compound was prepared from a mixture of 4-chloro-(2-pyrazinyl)-6-(trifluoromethyl)pyrimidine (50 mg, 0.191 mmol) and 4,5-dimethoxy-2-methylaniline (48 mg, 0.287 mmol) similar to Example 117 and isolated as a brown solid (47 mg, 56%). $^1$H NMR (CDCl$_3$): 9.74 (d, J=1.5 Hz, 1H), 8.76 (dd, J=1.5, 2.4 Hz, 1H), 8.71 (d, J=2.4 Hz, 1H), 7.51 (s, 1H), 6.82 (s, 1H), 6.78 (s, 1H), 6.55 (s, 1H), 3.93 (s, 3H), 3.86 (s, 3H), 2.21 (s, 3H).

EXAMPLE 154

4-(4,5-Dimethoxy-2-methylanilino)-2-(4-pyridinyl)-6-(trifluoromethyl)pyrimidine hydrochloride The title compound was prepared from a mixture of 4-chloro-2-(4-pyridinyl)-6-(trifluoromethyl)pyrimidine (50 mg, 0.193 mmol) and 4,5-dimethoxy-2-methylaniline (48 mg, 0.290 mmol) similar to Example 117 and isolated as a brown solid (23 mg, 30%). $^1$H NMR (CDCl$_3$): 9.54 (dd, J=1.5, 4.5 Hz, 2H), 9.05 (dd, J=1.5, 4.5 Hz, 2H), 7.98 (s, 1H), 7.60 (s, 2H), 7.29 (s, 1H), 4.71 (s, 3H), 4.63 (s, 3H), 3.00 (s, 3H).

EXAMPLE 155

4-(2-Chloro-5-methoxyanilino)-6-methyl-2-aminopyrimidine

The title compound was prepared from a mixture of 2-amino-4-chloro-6-methyl-pyrimidine (100 mg, 0.696 mmol) and 2-chloro-5-methoxyaniline hydrochloride (203 mg, 1.05 mmol) similar to Example 117 and isolated as a white solid (132 mg, 72%). $^1$H NMR (CDCl$_3$): 7.77 (d, J=2.7 Hz, 1H), 7.28 (d, J=9.0 Hz, 6.74 (s, 1H), 6.57 (dd, J=3.0, 8.7 Hz, 1H), 6.04 (s, 1H), 4.81 (s, 2H), 3.82 (s, 3H), 2.26 (s, 3H).

EXAMPLE 156

4-(3-Trifluoromethoxyanilino)-2-(2-pyridinyl)-6-(trifluoromethyl)pyrimidine hydrochloride A mixture of 4-chloro-2-(2-pyridinyl)-6-(trifluoromethyl)pyrimidine (25 mg, 0.096 mmol), 3-trifluoromethoxyaniline (19 µl, 0.144 mmol), and 2N HCl (75 µl) in water:ethanol (2:1, 5 ml) was refluxed for 24 h. The mixture was cooled to room temperature and the resulting precipitate was filtered, washed with water, water:ethanol (2:1) and dried to give a yellow solid (23 mg, 59%). $^1$H NMR (CDCl$_3$): 8.88–8.85 (m, 1H), 8.59–8.55 (m, 1H), 7.93–7.87 (m, 1H), 7.59 (s, 1H), 7.48 (t, J=8.3 Hz, 1H), 7.45 (dd, J=1.2, 7.5 Hz, 1H), 7.36 (s, 1H), 7.30–7.29 (m, 1H), 7.16–7.10 (m, 1H), 7.05 (s, 1H).

EXAMPLE 157

4-(4,5-Dimethoxy-2-methylanilino)-2-(3-pyridinyl)-6-(trifluoromethyl)pyrimidine The title compound was prepared from a mixture of 4-chloro-2-(3-pyridinyl)-6-(trifluoromethyl)pyrimidine (50 mg, 0.193 mmol) and 4,5-dimethoxy-2-methylaniline (48 mg, 0.290 mmol) similar to Example 117 and isolated as a red solid (8 mg, 11%). $^1$H NMR (CDCl$_3$): 9.69 (s, 1H), 8.74–8.68 (m, 2H), 7.56 (s, 1H), 7.43–7.39 (m, 1H), 6.84 (s, 1H), 6.83 (s, 1H), 6.46 (s, 1H), 3.94 (s, 3H), 3.86 (s, 3H), 2.23 (s, 3H).

EXAMPLE 158

4-(4-Chloro-2,5-dimethoxyanilino)-2-(4-pyridinyl)-6-(trifluoromethyl)pyrimidine hydrochloride The title compound was prepared from a mixture of 4-chloro-2-(4-pyridinyl)-6-(trifluoromethyl)pyrimidine (50 mg, 0.193 mmol) and 4-chloro-2,5-dimethoxyaniline (54 mg, 0.290 mmol) similar to Example 117 and isolated as a brown solid (55 mg, 68%). $^1$H NMR (CDCl$_3$): 8.78 (dd, J=1.8, 4.8 Hz, 2H), 8.31 (dd, J=1.8, 4.8 Hz, 2H), 8.24 (s, 1H), 7.52 (s, 1H), 7.01 (s, 1H), 6.96 (s, 1H), 3.98 (s, 3H), 3.91 (s, 3H).

EXAMPLE 159

4-(2-Hydroxy-5-methylanilino)-2-(3-pyridinyl)-6-(trifluoromethyl)pyrimidine The title compound was prepared from a mixture of 4-chloro-2-(3-pyridinyl)-6-(trifluoromethyl)pyrimidine (50 mg, 0.193 mmol) and 2-hydroxy-5-methylaniline (36 mg, 0.290 mmol) similar to Example 117 and isolated as a brown solid (10 mg, 15%). $^1$H NMR (Acetone-d$_6$): 9.58 (s, 1H), 8.87 (s, 1H), 8.74 (s, 1H), 8.72–8.68 (m, 2H), 7.89 (s, 1H), 7.58–7.53 (m, 1H), 7.24 (s, 1H), 6.92 (s, 2H), 2.33 (s, 3H).

EXAMPLE 160

4-(N-Methyl-3-methoxyanilino)-2-(2-pyridinyl)-6-trifluoromethyl-pyrimidine

A mixture of 4-chloro-2-(2-pyridinyl)-6-trifluoromethyl-pyrimidine (180 mg, 0.693 mmol) and N-methyl-3-methoxyaniline (112 mg, 0.816 mmol) in 3 mL of solvent (ethanol:water=2:1) was refluxed for 20 h. The solvent was removed under reduced pressure and the residue was dissolved in 25 mL of ethyl acetate. The ethyl acetate solution was washed with 25 mL of 1M NaOH, and the aqueous layer was reextracted with ethyl acetate (25 mL). The combined organic extracts were washed with saturated NaCl and dried over Na$_2$SO$_4$, filtered and concentrated. The crude product was purified by flash column chromatography (40–45% ethyl acetate/hexanes) to give the title compound as an oil (250 mg, 0.693 mmol, 100%). $^1$H NMR (CDCl$_3$): 8.86 (dd, J=0.6, 4.5 Hz, 1H), 8.50 (d, J=7.5 Hz, 1H), 7.85 (dt, J=1.8, 7.8 Hz, 1H), 7.42 (m, 2H), 6.95 (dd, J=1.8, 8.4 Hz, 1H), 6.86 (m, 1H), 6.82 (m. 1H), 3.85 (s, 3H), 3.68 (s, 3H).

EXAMPLE 161

4-(3,5-Dimethoxyanilino)-2-(4-pyridinyl)-6-trifluoromethyl-pyrimidine

The title compound was prepared from 4-chloro-2-(4-pyridinyl)-6-trifluoromethyl-pyrimidine (150 mg, 0.578 mmol) and 3,5-dimethoxyaniline (95 mg, 0.621 mmol) similar to Example 160 and was isolated as off-white solid (119 mg, 0.316 mmol, 55%). $^1$H NMR (DMSO-d$_6$): 10.31 (s, br, 1H), 8.80 (m, 2H), 8.17 (m, 2H), 7.17 (s, 1H), 7.04 (s, 2H), 6.32 (m, 1H), 3.80 (s, 6H), 3.53 (s, 1H).

EXAMPLE 162

4-(5-Chloro-2-methoxyanilino)-2-(4-pyridinyl)-6-trifluoromethyl-pyrimidine

The title compound was prepared from 4-chloro-2-(4-pyridinyl)-6-trifluoromethyl-pyrimidine (150 mg, 0.578 mmol) and 5-chloro-2-methoxyaniline (98 mg, 0.621 mmol) similar to Example 160 and was isolated as off-white solid (84 mg, 0.221 mmol, 38%). $^1$H NMR (CDCl$_3$/MeOH-d$_4$): 8.72 (d, J=4.2 Hz, 2H), 8.51 (s, 1H), 8.34 (d, J=4.5 Hz), 7.09 (m, 2H), 6.91 (d, J=8.4 Hz, 1H), 3.93 (s, 3H)

EXAMPLE 163

4-(3,5-Dimethoxyanilino)-2-(2,6-dichloro-4-pyridinyl)-6-trifluoromethyl-pyrimidine a. 4-Chloro-2-(2,6-dichloro-4-pyridinyl)-6-trifluoromethyl-pyrimidine. A mixture of POCl$_3$ (freshly distilled, 0.50 mL, 5.35 mmol) in 2.5 mL of DMF was stirred at 0° C. for 45 min. To the mixture was added 2-(2,6-dichloro-4-pyridinyl)-6-trifluoromethyl-4-pyrimidinol (98 mg, 0.317 mmol) in 0.5 mL of DMF and the mixture was allowed to warm to room temperature. The resulting mixture was heated overnight at 100° C. The reaction mixture was cooled to room temperature and it was extracted with ethyl acetate (10 mL×3). The combined extracts were washed with water (10 mL×3) and saturated NaCl, dried over $Na_2SO_4$, filtered and concentrated. The residue was purified by flash column chromatography (5% ethyl acetate/hexanes) to obtain the title compound as a white solid (74 mg, 0.226 mmol, 72%, mp 109–110° C.). $^1$H NMR ($CDCl_3$): 8.30 (s, 2H), 7.51 (s, 1H).

b. 4-(3,5-Dimethoxyanilino)-2-(2,6-dichloro-4-pyridinyl)-6-trifluoromethyl-pyrimidine. The title compound was prepared from 4-chloro-2-(2,6-dichloro-4-pyridinyl)-6-trifluoromethyl-pyrimidine (57 mg, 0.174 mmol) and 3,5-dimethoxyaniline (38 mg, 0.248 mmol) similar to Example 160 and was isolated as a yellow crystalline solid (58 mg, 0.130 mmol, 75%). $^1$H NMR ($CDCl_3$): 8.25 (s, 2H), 7.25 (s, br, 1H), 7.02 (s, 1H), 6.62 (m, 2H), 6.38 (t, J=1.8 Hz, 1H), 3.84 (s, 6H).

EXAMPLE 164

4-(2-Chloro-5-methoxyanilino)-2-(2,6-dichloro-4-pyridinyl)-6-trifluoromethyl-pyrimidine The title compound was prepared from 4-chloro-2-(2,6-dichloro-4-pyridinyl)-6-trifluoromethyl-pyrimidine (52 mg, 0.159 mmol) and 2-chloro-5-methoxyaniline (40 mg, 0.255 mmol) similar to Example 160 and was isolated as a yellow crystalline solid (13 mg, 0.029 mmol, 18%). $^1$H NMR ($CDCl_3$): 8.27 (s, 2H), 7.76 (s, br, 1H), 7.40 (s, 1H), 7.38 (s, 1H), 7.02 (s, 1H), 6.77 (m, 1H), 3.90 (s, 3H).

EXAMPLE 165

4-(2-Methoxy-5-methyl-4-nitroanilino)-2-(3-pyridinyl)-6-trifluoromethyl-pyrimidine The title compound was prepared from 4-chloro-2-(3-pyridinyl)-6-trifluoromethyl-pyrimidine (51 mg, 0.194 mmol) and 2-methoxy-5-methyl-4-nitroaniline (43 mg, 0.236 mmol) similar to Example 160 and was isolated as off-white crystalline solid (mp 128–133° C., 23 mg, 0.057 mmol, 29%). $^1$H NMR ($CDCl_3$/MeOH-d4): 9.42 (s, 1H), 8.75 (m, 1H), 8.62 (m, 1H), 7.77 (s, 1H), 7.68 (s, 1H), 7.42 (dd, J=4.8, 8.1 Hz, 1H), 6.82 (s, 1H), 4.01 (s, 3H), 2.01 (s, 3H).

EXAMPLE 166

4-(1H-5-Indolyl-amino)-2-(3-pyridinyl)-6-trifluoromethyl-pyrimidine

A mixture of 4-chloro-2-(3-pyridinyl)-6-trifluoromethyl-pyrimidine (42 mg, 0.162 mmol), 1H-5-indolylamine (31 mg, 235 mmol) and potassium carbonate (25 mg, 0.180 mmol) was heated overnight in 1 mL of DMF at 100° C. in a sealed tube. The reaction mixture was cooled to room temperature, diluted with 20 mL of ethyl acetate, washed with water (20 mL×3) and saturated NaCl. The organic layer was dried over $Na_2SO_4$, filtered, concentrated and the residue was purified by flash column chromatography (30% ethyl acetate/hexanes) to obtain the title compound as a white solid (mp 142–143° C., 45 mg, 0.127 mmol, 78%). $^1$H NMR ($CDCl_3$): 9.56 (d, J=1.5 Hz, 1H), 8.74 (dt, J=1.8, 8.1 Hz, 1H), 8.63 (dd, J=3, 5.1 Hz, 1H), 7.66 (m, 1H), 7.46 (m, 2H), 7.30 (d, J=3 Hz, 1H), 7.19 (m, 1H), 6.82 (s, 1H), 6.55 (d, J=3 Hz, 1H).

EXAMPLE 167

4-(5-Methoxy-2-methyl-4-nitroanilino)-2-(3-pyridinyl)-6-trifluoromethyl-pyrimidine The title compound was prepared from 4-chloro-2-(3-pyridinyl)-6-trifluoromethyl-pyrimidine (48 mg, 0.185 mmol) and 5-methoxy-2-methyl-4-nitroaniline (35 mg, 0.192 mmol) similar to Example 166 and was isolated as a white solid (mp 128–132° C., 11 mg, 0.027 mmol, 15%). $^1$H NMR ($CDCl_3$): 9.62 (s, 1H), 8.68 (m, 2H), 7.79 (s, 1H), 7.73 (s, 1H), 7.48 (m, 1H), 7.01 (s, 1H), 4.02 (s, 3H), 2.63 (s, 1H).

EXAMPLE 168

4-(3-Trifluoromethyl-1-pyrazolyl)-2-(3-pyridinyl)-6-trifluoromethyl-pyrimidine

The title compound was prepared from 4-chloro-2-(3-pyridinyl)-6-trifluoromethyl-pyrimidine (74 mg, 0.285 mmol) and 3-trifluromethyl-pyrazol (48 mg, 0.353 mmol) similar to Example 166 and was isolated as a white solid (mp 139–140° C., 53 mg, 0.148 mmol, 52%). $^1$H NMR ($CDCl_3$): 9.73 (s, 1H), 8.82 (m, 3H), 8.26 (s, 1H), 7.50 (m, 1H), 6.87 (d, J=2.7 Hz, 1H).

EXAMPLE 169

4-(4,5-Dihydro-2-thiazolyl-amino)-2-(3-pyridinyl)-6-trifluoromethyl-pyrimidine

The title compound was prepared from 4-chloro-2-(3-pyridinyl)-6-trifluoromethyl-pyrimidine (75 mg, 0.289 mmol) and 2-amino-2-thiazoline (37 mg, 0.362 mmol) similar to Example 166 and was isolated as a white solid (20 mg, 0.61 mmol, 21%). $^1$H NMR ($CDCl_3$/MeOH-$d_4$) 9.45 (s, 1H), 8.73 (dt, 1.8, 8.1 Hz, 1H), 8.58 (dd, J=1.8, 5.1 Hz, 1H), 7.47 (m, 1H), 6.70 (s, 1H), 3.93 (t, J=6.6 Hz, 2H), 3.04 (t, J=7.2 Hz, 2H).

EXAMPLE 170

4-(1-Pyrazolyl)-2-(3-pyridinyl)-6-trifluoromethyl-pyrimidine

The title compound was prepared from 4-chloro-2-(3-pyridinyl)-6-trifluoromethyl-pyrimidine (74 mg, 0.285 mmol) and pyrazole (28 mg, 0.425 mmol) similar to Example 166 and was isolated as a white solid (mp 151–152° C., 67 mg, 0.230 mmol, 81%). $^1$H NMR ($CDCl_3$) 9.71 (s, 1H), 8.77 (m, 3H), 8.19 (s, 1H), 7.88 (m, 1H), 7.47 (m, 1H), 6.61 (dd, J=1.5, 2.7 Hz, 1H).

EXAMPLE 171

4-(4,5,6,7-Tetrahydro-1H-indazolyl)-2-(3-pyridinyl)-6-trifluoromethyl-pyrimidine The title compound was prepared from 4-chloro-2-(3-pyridinyl)-6-trifluoromethyl-pyrimidine (76 mg, 0.293 mmol) and 4,5,6,7-tetrahydroindazole (44 mg, 0.360 mmol) similar to Example 166 and was isolated as a white solid (25 mg, 0.072 mmol, 25% %). $^1$H NMR (CDCl$_3$) 9.68 (d, J=1.2 Hz, 1H), 8.75 (m, 2H), 8.40 (s, 1H), 8.07 (s, 1H), 7.45 (ddd, J=1.2, 5.1, 9.0 Hz, 1H), 2.73 (m, 4H), 1.88 (m, 4H).

EXAMPLE 172

4-(1H-3-Pyrazolyl-amino)-2-(3-pyridinyl)-6-trifluoromethyl-pyrimidine

The title compound was prepared from 4-chloro-2-(3-pyridinyl)-6-trifluoromethyl-pyrimidine (75 mg, 0.289 mmol) and 3-amino pyrazole (31 mg, 0.373 mmol) similar to Example 166 and was isolated as a white solid (mp 230° C. decompose, 31 mg, 0.101 mmol, 35%). $^1$H NMR (DMSO-d$_6$) 9.62 (d, J=1.2 Hz, 1H), 8.77 (m, 3H), 7.71 (s, 1H), 7.62 (dd, J=4.5, 7.5 Hz, 1H), 6.09 (d, J=3 Hz, 1H), 5.89 (s, 1H).

EXAMPLE 173

6-Methyl-2-(2-pyridinyl)-4-(3-trifloromethylbenzylamino)-pyrimidine

A mixture of 4-chloro-6-methyl-2-(2-pyridinyl)pyrimidine (82.3 mg, 0.4 mmol), 3-trifluoromethylbenzylamine (70.1 mg, 0.4 mmol), water (5 ml) and 2N HCl (300 µl) was refluxed for two days. The resulting solution was basified to pH ~11 with ammonia and extracted with ethyl acetate (10 ml×3). The combined ethyl acetate extracts were dried with sodium sulfate, and evaporated under vacuum. The residue was purified by column chromatography (hexane/ethyl acetate: 1/1) to give the title compound as a solid (34 mg, 25%). $^1$H NMR (CD$_3$OD): 8.59 (d, J=4.2 Hz, 1H), 8.27 (m, 2H), 7.86 (m, 2H), 7.43 (m, 2H), 6.18 (s, 2H), 4.76 (s, 2H), 2.26 (s, 3H).

EXAMPLE 174

6-Methyl-4-(3-phenoxyanilino)-2-(2-pyridinyl)pyrimidine

The title compound was prepared from 4-chloro-6-methyl-2-(2-pyridinyl)pyrimidine (82.3 mg, 0.4 mmol) and 3-phenoxyaniline (74.0 mg, 0.4 mmol) similar to Example 173 and was isolated as a white solid. (96 mg, 68%). $^1$H NMR (CDCl$_3$): 8.62 (d, J=4.2 Hz, 1H), 8.25 (d, J=8.1 Hz, 1H), 7.65 (t, J=1.5 Hz, 1H), 7.21 (m, 5H), 6.94 (m, 5H), 6.64 (d, J=8.1 Hz, 1H), 6.49 (s, 1H), 2.33 (s, 3H),

EXAMPLE 175

4-(3-Chloroanilino)-6-methyl-2-(2-pyridinyl)pyrimidine

The title compound was prepared from 4-chloro-6-methyl-2-(2-pyridinyl)pyrimidine (82.3 mg, 0.4 mmol) and 3-chloroaniline (50.8 mg, 0.4 mmol) similar to Example 173 and was isolated as a white solid (99 mg, 84%). $^1$H NMR (CDCl$_3$): 8.59 (d, J=4.2 Hz, 1H), 8.29 (d, J=8.1 Hz, 1H), 7.80 (br, 1H), 7.67 (t, J=1.5 Hz, 1H), 7.38 (s, 1H), 7.19 (m, 1H), 7.10 (m, 2H), 6.91 (m, 1H), 6.41 (s, 1H), 2.28 (s, 3H).

EXAMPLE 176

4-(3,4-Dimethoxyanilino)-6-methyl-2-(2-pyridinyl) pyrimidine

The title compound was prepared from 4-chloro-6-methyl-2-(2-pyridinyl)pyrimidine (82.3 mg, 0.4 mmol) and 3,4-dimethoxyaniline (61.2 mg, 0.4 mmol) similar to Example 173 and was isolated as a white solid (108 mg, 84%). $^1$H NMR (CDCl$_3$): 8.63 (d, J=4.2 Hz, 1H), 8.29 (d, J=8.1 Hz, 1H), 7.65 (t, J=1.5 Hz, 1H), 7.18 (m, 2H), 6.7 (s, 1H), 6.71 (s, 2H), 6.28 (s, 1H), 3.73 (s, 3H), 3.71 (s, 3H), 2.29 (s, 3H).

EXAMPLE 177

4-(4-Fluoro-3-methoxyanilino)-6-methyl-2-(2-pyridinyl)pyrimidine

The title compound was prepared from 4-chloro-6-methyl-2-(2-pyridinyl)pyrimidine (82.3 mg, 0.4 mmol) and 4-fluoro-3-methoxyaniline (56.4 mg, 0.4 mmol) similar to Example 173 and was isolated as a white solid (96.7 mg, 78%). $^1$H NMR (CDCl$_3$): 8.63 (d, J=4.2 Hz, 1H), 8.29 (d, J=7.5 Hz, 1H), 7.65 (t, J=7.5 Hz, 1H), 7.42 (s, 1H), 7.20 (m, 1H), 7.0 (d, J=7.5 Hz, 1H), 6.90 (m, 1H), 6.69 (m, 1H), 3.71 (s, 3H), 2.30 (s, 3H),

EXAMPLE 178

4-(3-Isopropoxyanilino)-6-methyl-2-(2-pyridinyl) pyrimidine

The title compound was prepared from 4-chloro-6-methyl-2-(2-pyridinyl)pyrimidine (82.3 mg, 0.4 mmol) and 3-isopropoxyaniline (60.4 mg, 0.4 mmol) similar to Example 173 and was isolated as a white solid (88 mg, 69%). $^1$H NMR (CDCl$_3$): 8.64 (d, J=4.2 Hz, 1H), 8.35 (d, J=8.1 Hz, 1H), 7.7 (t, J=8.1 Hz, 1H), 7.24 (m, 1H), 7.15 (m, 1H), 6.96 (s, 1H), 6.76 (m, 2H), 6.60 (d, J=8.1 Hz, 1H), 6.18 (m, 1H), 4.45 (m, 1H), 2.37 (s, 3H), 1.25 (d, J=6.0 Hz, 6H).

EXAMPLE 179

4-(3,4-Dimethoxyanilino)-6-trifluoromethyl-2-(2-pyridinyl)pyrimidine a. 4-Hydroxy-2-(2-pyridinyl)-6-trifluoromethyl-pyrimidine. To a solution of pyridine-2-carboxamidine hydrochloride (5.0 g, 33.2 mmol) in 20 ml of water was added concentrated aqueous KOH and the resulting mixture was extracted with ethyl acetate (50 mL×3). The extract was evaporated under vacuum to afford 4.0 g of free base. To a solution of the free base and 4,4,4-trifluoro-but-2-ynoic acid ethyl ester (6.0 g, 36 mmol) in ethanol (50 mL) at 0° C.~60° C. was added dropwise potassium hydroxide solution (1.68 g in 40 mL water) in twenty minutes. The solution was then refluxed 2.5 h. The solvent was evaporated under vacuum and the residue was extracted with ethyl acetate (30 ml×3). The combined ethyl acetate extracts were dried with sodium sulfate, evaporated to give a solid. It was recrystallized with Hexane/methylene chloride/methanol: 6/2/1) to give the product as a white solid (2.50 g, 31.2%). $^1$H NMR (CD$_3$OD): 8.63 (d, J=4.8 Hz, 1H), 8.31 (d, J=7.8 Hz, 1H), 7.90 (t, J=7.8 Hz, 1H), 7.49 (m, 1H), 6.73 (s, 1H), 4.76 (s, 1H).

b. 4-Chloro-2-(2-pyridinyl)-6-trifluoromethyl-pyrimidine. A mixture of 4-hydroxy-2-(2-pyridinyl)-6-trifluoromethyl-pyrimidine (2.50 g, 10.37 mmol) and phosphorus oxychloride (20 mL) was refluxed for 3 h. The resulting solution was evaporated under vacuum and the residue was basified to pH ~11 with ammonia and extracted with ethyl acetate (15 ml×3). The combined ethyl acetate extracts were dried with sodium sulfate, evaporated to give a solid. The solid was purified by column chromatography (hexane/ethyl acetate: 2/1~1/3) to afford a yellow solid (2.30 g, 86%). $^1$H NMR (CDCl$_3$): 8.76 (d, J=2.7 Hz, 1H), 8.42 (d, J=7.8 Hz, 1H), 7.76 (t, J=1.8 Hz, 1H), 7.55 (d, J=2.4 Hz, 1H), 7.34 (t, J=5.1 Hz, 1H).

c. 4-(3,4-Dimethoxyanilino)-2-(2-pyridinyl)-6-trifluoromethylpyrimidine. The title compound was prepared from 4-chloro-2-(2-pyridinyl)-6-trifluoromethyl-pyrimidine (51.8 mg, 0.2 mmol) and 3,4-dimethoxyaniline (51.8 mg, 0.2 mmol) similar to Example 173 and was isolated as a white solid (61 mg, 81%). $^1$H NMR (CDCl$_3$): 8.71 (d, J=0.9 Hz, 1H), 8.43 (d, J=7.8 Hz, 1H), 7.45 (t, J=7.8 Hz, 1H), 7.50 (S, 1H), 7.35 (m, 1H), 6.77 (m, 4H), 3.80 (s, 3H), 3.77 (s, 3H).

EXAMPLE 180

4-(5-Chloro-2-methoxyanilino)-2-(3-pyridinyl)-6-trifluoromethylpyrimidine

A mixture of 4-chloro-2-(3-pyridinyl)-6-trifluoromethylpyrimidine (100 mg, 0.385 mmol), 2-methoxy-5-chloroaniline (90 mg, 0.577 mmol) and 2N HCl (150 μl) in 1:1 ethanol/water (5 ml) was refluxed for 48 h. The resulting yellow solid was collected by filtration, washed with water, ethanol/water (1:4) and then dried under vacuum to give the title compound (100 mg, 67%). $^1$H NMR (CDCl$_3$): 9.66 (d, J=1.8 Hz, 1H), 8.70–8.76 (m, 2H), 7.68 (dd, J=7.5, 1.0 Hz, 1H), 7.44 (dd, J=7.5, 1.0 Hz, 1H), 7.09 (dd, J=8.7, 2.7 Hz, 1H), 6.92 (s, 1H), 6.87 (d, J=8.7 Hz, 1H), 3.91 (s, 3H).

EXAMPLE 181

4-(2-Methoxy-5-nitroanilino)-2-(2-pyrazinyl)-6-trifluoromethylpyrimidine

The title compound was prepared from 4-chloro-2-(2-pyrazinyl)-6-trifluoromethylpyrimidine (40 mg, 0.153 mmol) and 2-methoxy-5-nitroaniline (39 mg, 0.230 mmol), similar to Example 180 and was isolated as a yellow solid (30 mg, 51%). $^1$H NMR (CDCl$_3$): 9.760 (d, J=1.5 Hz, 1H), 8.86 (dd, J=1.8, 2.7 Hz, 1H), 8.74 (d, J=2.4 Hz, 1H), 8.10 (dd, J=2.7, 9.0 Hz, 1H), 7.34 (s, 1H), 7.07 (d, J=9.0 Hz, 1H), 4.08 (s, 3H).

EXAMPLE 182

4-(5-Methoxy-2-nitroanilino)-2-(2-pyrazinyl)-6-trifluoromethylpyrimidine

The title compound was prepared from 4-chloro-2-(2-pyrazinyl)-6-trifluoromethylpyrimidine (40 mg, 0.153 mmol) and 5-methoxy-2-nitroaniline (39 mg, 0.230 mmol), similar to Example 180 and was isolated as an off white solid (35 mg, 58%). $^1$H NMR (CDCl$_3$): 9.69 (d, J=1.5 Hz, 1H), 8.83 (dd, J=1.5, 2.4 Hz, 1H), 8.72 (d, J=2.4 Hz, 1H), 8.08 (d, J=9.6 Hz, 1H), 7.11 (s, 1H), 6.27 (dd, J=2.7, 9.6 Hz, 1H), 6.15 (d, J=2.7 Hz, 1H), 3.83 (s, 3H).

EXAMPLE 183

4-(3,5-Dimethoxyanilino)-2-(2-pyrazinyl)-6-trifluoromethylpyrimidine

The title compound was prepared from 4-chloro-2-(2-pyrazinyl)-6-trifluoromethylpyrimidine (40 mg, 0.153 mmol) and 3,5-dimethoxyaniline (35 mg, 0.23 mmol), similar to Example 180 and was isolated as a pale solid (30 mg, 52%). $^1$H NMR (CDCl$_3$): 9.74 (d, J=1.5 Hz, 1H), 7.78 (m, 1H), 8.72 (d, J=2.4 Hz, 1H), 7.48 (s, 1H), 7.10 (s, 1H), 6.53 (d, J=2.1 Hz, 2H) 6.39 (t, J=2.1 Hz, 1H), 3.83 (s, 6H).

EXAMPLE 184

4-(5-Carboxy-2-methoxyanilino)-2-(2-pyrazinyl)-6-trifluoromethylpyrimidine

The title compound was prepared from 4-chloro-2-(2-pyrazinyl)-6-trifluoromethylpyrimidine (40 mg, 0.154 mmol) and 5-carboxy-2-methoxyaniline (38 mg, 0.231 mmol), similar to Example 180 and was isolated as an off white solid (20 mg, 33%). $^1$H NMR (CDCl$_3$): 9.99 (brs, 1H), 9.660 (d, J=1.5 Hz, 1H), 8.86 (m, 3H), 7.80 (d, 2H), 7.2 (m, 2H), 3.94 (s, 3H).

EXAMPLE 185

4-(5-Hydroxy-2-nitroanilino)-2-(3-pyridinyl)-6-trifluoromethylpyrimidine

The title compound was prepared from 4-chloro-2-(3-pyridinyl)-6-trifluoromethylpyrimidine (60 mg, 0.23 mmol) and 5-hydroxy-2-nitroaniline (52 mg, 0.34 mmol) similar to Example 180. The reaction mixture was neutralized with 2N NaOH to pH 7.0 and the solvent was removed under vacuo. The product was purified by column chromatography (20% ethyl acetate in hexane) to give 55 mg (63%) of the title compound as a light yellow solid. $^1$H NMR (CDCl$_3$): 9.40 (d, J=1.2 Hz, 1H), 8.71 (dd, J=1.2, 4.8 Hz, 1H), 8.57 (ddd, J=2.1, 3.9, 7.8 Hz, 1H), 8.04 (d, J=2.7 Hz, 1H), 7.42 (dd, J=3.9, 8.7 Hz, 1H), 7.32 (dd, J=6.0, 9.0 Hz, 1H), 7.23 (s, 1H), 6.92 (d, J=9.0 Hz, 1H), 6.19 (s, 2H).

EXAMPLE 186

4-(2-Ethylsulfonyl-5-hydroxyanilino)-2-(2-pyrazinyl)-6-trifluoromethylpyrimidine The title compound was prepared from 4-chloro-2-(2-pyrazinyl)-6-trifluoromethylpyrimidine (40 mg, 0.154 mmol) and 2-ethylsulfonyl-5-hydroxyaniline (46 mg, 0.231 mmol) similar to Example 180. The reaction mixture was evaporated under vacuum to give a residue. The residue was precipitated using acetone to give the product as a yellow solid (30 mg, 46%). $^1$H NMR (DMSO-d$_6$): 9.45 (s, 1H), 8.71 (m, 3H), 7.84 (brs, 1H), 7.0 (brd, 1H), 6.08 (brd, 1H), 3.0 (q, 2H), 1.0 (t, 3H).

EXAMPLE 187

4-(2-Methoxy-5-methylanilino)-2-(2-pyrazinyl)-6-trifluoromethylpyrimidine

The title compound was prepared from 4-chloro-2-(2-pyrazinyl)-6-trifluoromethylpyrimidine (40 mg, 0.152 mmol) and 2-methoxy-5-methylaniline (28 mg, 0.231 mmol) similar to example 180 and was isolated as a solid (43 mg, 81%). $^1$H NMR (CDCl$_3$): 9.73 (m, 1H), 8.44–8.41 (m, 1H), 7.81–7.75 (m, 1H), 7.46 (s, 1H), 7.34–7.28 (m, 2H), 7.23 (t, J=8.1 Hz, 1H), 7.09–7.06 (m, 1H), 7.00–6.97 (m, 1H), 6.55 (d, J=0.6 Hz, 1H), 2.44 (s, 3H), 2.43 (d, J=0.6, 3H).

EXAMPLE 188

4-(5-Hydroxy-2-methylanilino)-2-(2-pyridinyl)-6-trifluoromethylpyrimidine

The title compound was prepared from 4-chloro-2-(2-pyridinyl)-6-trifluoromethylpyrimidine (40 mg, 0.154 mmol) and 5-hydroxy-2-methylaniline (28 mg, 0.231 mmol) similar to example 185 and was isolated as a pale solid (40 mg, 75%). $^1$H NMR (CDCl$_3$): 9.73 (m, 1H), 8.44–8.41 (m, 1H), 7.81–7.75 (m, 1H), 7.46 (s, 1H), 7.34–7.28 (m, 2H), 7.23 (t, J=0.1 Hz, 1H), 7.09–7.06 (m, 1H), 7.00–6.97 (m, 1H), 6.55 (d, J=0.6 Hz, 1H), 2.44 (s, 3H), 2.43 (d, J=0.6, 3H).

EXAMPLE 189

4-(2-Chloro-5-hydroxyanilino)-2-(2-pyridinyl)-6-trifluoromethylpyrimidine

The title compound was prepared from 4-chloro-2-(2-pyridinyl)-6-trifluoromethylpyrimidine (40 mg, 0.154 mmol) and 2-chloro-5-hydroxyaniline (30 mg, 0.231 mmol) similar to Example 185 and was isolated as an off white solid (15 mg, 28%). $^1$H NMR (DMSO-d$_6$): 9.89 (s, 1H), 9.85 (brs, NH), 8.74 (d, J=5.7, 1H), 8.22 (d, J=7.8 Hz, 1H), 7.97 (ddd, J=1.8, 5.7, 7.8 Hz, 1H), 7.54 (ddd, J=4.5, 6.0, 7.8 Hz, 1H), 7.35 (m, 2H), 7.19 (s, 1H), 6.70 (dd, J=2.7, 5.7 Hz, 1H).

EXAMPLE 190

4-(2-Methoxy-5-methylanilino)-2-(2-pyridinyl)-6-trifluoromethylpyrimidine

The title compound was prepared from 4-chloro-2-(2-pyridinyl)-6-trifluoromethylpyrimidine (60 mg, 0.23 mmol) and 2-methoxy-5-methylaniline (46 mg, 0.34 mmol) similar to Example 180. After completion of the reaction the solvent was removed under reduced pressure. The product was purified (5 mg) by preparative TLC plate using 1:1 hexane/ethyl acetate as mobile phase. $^1$H NMR (DMSO-d$_6$): 9.68 (s, 1H), 8.75 (d, J=3.6, 1H), 8.26 (d, J=7.2 Hz, 1H), 8.00 (t, J=7.2 Hz, 1H), 7.55 (dd, J=4.0, 7.2 Hz, 1H), 7.04 (m, 2H), 3.82 (s, 3H), 2.02 (s, 3H).

EXAMPLE 191

4-(2-Ethylsulfonyl-5-hydroxyanilino)-2-(2-pyridinyl)-6-trifluoromethylpyrimidine The title compound was prepared from 4-chloro-2-(2-pyridinyl)-6-trifluoromethylpyrimidine (40 mg, 0.154 mmol) and 2-ethylsulfonyl-5-hydroxyaniline (46 mg, 0.231 mmol) similar to Example 186 and was isolated as a yellow solid (35 mg, 54%). $^1$H NMR (CDCl$_3$): 8.88 (s, 1H), 8.60 (brt, 2H), 8.01 (t, 1H), 7.52 (m, 2H), 7.01 (m, 2H), 3.02 (q, 2H), 1.22 (t, 3H).

EXAMPLE 192

4-(2-Hydroxy-5-isopropylanilino)-2-(2-pyridinyl)-6-trifluoromethylpyrimidine

The title compound was prepared from 4-chloro-2-(2-pyridinyl)-6-trifluoromethylpyrimidine (40 mg, 0.154 mmol) and 2-hydroxy-5-isopropylaniline (35 mg, 0.231 mmol) similar to Example 185 and was isolated as a solid (32 mg, 55%). $^1$H NMR (DMSO-d$_6$): 8.74 (s, 1H), 8.73 (d, J=0.9 Hz, 1H), 8.35 (d, J=7.8 Hz, 2H), 7.95 (t, J=8.1 Hz, 2H), 7.54 (m, 2H), 6.60 (m, 2H), 2.78 (sep, J=6.9 Hz, 1H), 1.20 (d, J=6.9 Hz, 6H).

EXAMPLE 193

4-(5-Hydroxy-2-methylanilino)-2-(2-pyrazinyl)-6-trifluoromethylpyrimidine

The title compound was prepared from 4-chloro-2-(2-pyrazinyl)-6-trifluoromethylpyrimidine (40 mg, 0.154 mmol) and 5-hydroxy-2-methylaniline (34 mg, 0.231 mmol) similar to Example 190 and was isolated as a solid (3 mg). $^1$H NMR (CDCl$_3$): 9.74 (d, J=1.2 Hz, 1H), 8.76–8.71 (m, 2H), 7.30 (brs, 1H), 7.18 (d, J=8.4 Hz, 1H), 6.87 (brd, 1H), 6.78 (dd, J=8.4, 2.4 Hz, 1H), 6.73 (s, 1H), 2.21 (s, 3H).

EXAMPLE 194

4-(2-Chloro-5-hydroxyanilino)-2-(2-pyrazinyl)-6-trifluoromethylpyrimidine

The title compound was prepared from 4-chloro-2-(2-pyrazinyl)-6-trifluoromethylpyrimidine (40 mg, 0.154 mmol) and 2-chloro-5-hydroxyaniline (33 mg, 0.231 mmol) similar to Example 190 and was isolated as a solid (6 mg). $^1$H NMR (CDCl$_3$): 9.72 (d, J=1.5 Hz, 1H), 8.78 (dd, J=5.7, 1.5 Hz, 1H), 8.73 (d, J=1.2 Hz, 1H), 7.33 (d, J=8.7 Hz, 1H), 7.05 (s, 1H), 7.04 (d, J=8.7 Hz, 1H), 6.73 (dd, J=8.7, 2.7 Hz, 1H), 6.29 (d, J=2.7 Hz, 1H), 6.19 (dd, J=8.4, 2.7 Hz, 1H).

EXAMPLE 195

4-(3,5-Dimethoxyanilino)-2-(2-pyridinyl)-6-trifluoromethylpyrimidine

The title compound was prepared from 4-chloro-2-(2-pyridinyl)-6-trifluoromethylpyrimidine (30 mg, 0.115 mmol) and 3,5-dimethoxyaniline (26 mg, 0.172 mmol) similar to Example 180 and was isolated as a light yellow solid (16 mg, 37% yield). $^1$H NMR (CDCl$_3$): 8.85 (dd, J=4.8, 1.5 Hz, 1H), 8.56 (d, J=6.9 Hz, 1H), 7.89 (ddd, J=9.3, 7.5, 1.5 Hz, 1H), 7.65 (brs, 1H), 7.45 (dd, J=9.3, 4.5 Hz, 1H), 7.09 (s, 1H), 6.51 (d, J=1.8 Hz, 1H), 6.37 (t, J=1.8 Hz, 1H), 3.93 (s, 6H).

EXAMPLE 196

4-(2,5-Dimethylanilino)-2-(2-pyrazinyl)-6-trifluoromethylpyrimidine

The title compound was prepared similar to 4-chloro-2-(2-pyrazinyl)-6-trifluoromethylpyrimidine (30 mg, 0.115 mmol) and 2,5-dimethylaniline (21 mg, 0.172 mmol) similar to Example 180 and was isolated as an off white solid (35 mg, 80% yield). $^1$H NMR (CDCl$_3$): 9.74 (d, J=1.5 Hz, 1H), 8.76 (dd, J=1.5, 2.4 Hz, 1H), 8.71 (d, J=2.4 Hz, 1H), 7.48 (brs, 1H), 7.22 (d, J=8.1 Hz, 1H), 7.12 (m, 2H), 6.65 (s, 1H), 2.36 (s, 3H), 2.23 (s, 3H).

EXAMPLE 197

4-(5-Chloro-2-methoxyanilino)-2-(2-pyrazinyl)-6-trifluoromethylpyrimidine

The title compound was prepared from 4-chloro-2-(2-pyrazinyl)-6-trifluoromethylpyrimidine (30 mg, 0.115 mmol) and 5-chloro-2-methoxyaniline (27 mg, 0.173 mmol) similar to Example 185 and was isolated as a solid (10 mg, 23% yield). $^1$H NMR (CDCl$_3$): 9.72 (d, J=1.2 Hz, 1H), 8.82 (t, J=1.8 Hz, 1H), 8.72 (d, J=2.4 Hz, 1H), 8.23 (brs, 1H), 7.71 (brs, 1H), 7.15 (dd, J=8.4, 2.4 Hz, 1H), 7.04 (s, 1H), 6.88 (d, J=8.4 Hz, 1H), 3.90 (s, 3H).

EXAMPLE 198

4-(5-Chloro-2-hydroxyanilino)-2-(2-pyrazinyl)-6-trifluoromethylpyrimidine

The title compound was prepared from 4-chloro-2-(2-pyrazinyl)-6-trifluoromethylpyrimidine (30 mg, 0.115 mmol) and 5-chloro-2-hydroxyaniline (25 mg, 0.173 mmol) similar to Example 185 and was isolated as a solid (7 mg, 16% yield). $^1$H NMR (CDCl$_3$): 9.68 (d, J=0.9 Hz, 1H), 8.84 (t, J=2.4 Hz, 1H), 8.60 (d, J=2.4 Hz, 1H), 7.89 (brs, 1H), 7.41 (s, 1H), 7.07 (m, 2H), 6.91 (d, J=8.7 Hz, 1H).

EXAMPLE 199

4-(5-Hydroxy-2-isopropylanilino)-2-(2-pyrazinyl)-6-trifluoromethypyrimidine

The title compound was prepared from 4-chloro-2-(2-pyrazinyl)-6-trifluoromethylpyrimidine (30 mg, 0.115 mmol) and 5-hydroxy-2-isopropylaniline (26 mg, 0.173 mmol) similar to Example 190 and was isolated as a solid. $^1$H NMR (CDCl$_3$): 9.75 (d, J=1.2 Hz, 1H), 8.77 (t, J=1, 8 Hz, 1H), 8.72 (d, J=2.7 Hz, 1H), 7.29 (brs, 1H), 7.27 (s, 1H), 6.91 (dd, J=8.4, 2.4 Hz, 1H), 6.79 (d, J=2.7 Hz, 1H), 6.70 (s, 1H), 4.13 (sep, J=6.9 Hz, 1H), 1.20 (d, J=6.9 Hz, 6H).

EXAMPLE 200

4-(2,5-Dimethoxyphenylethylamino)-2-(3-pyridinyl)-6-trifluoromethylpyrimidine

The title compound was prepared from 4-chloro-2-(3-pyridinyl)-6-trifluoromethylpyrimidine (40 mg, 0.154 mmol) and 2,5-dimethoxyphenylethylamine (28 mg, 0.232 mmol) similar to Example 186 and was isolated as an off white solid (35 mg, 54% yield). $^1$H NMR (CDCl$_3$): 9.59 (brs, 1H), 8.69 (d, J=4.8 Hz, 1H), 7.37 (dd, J=4.8, 8.4 Hz, 1H), 6.76 (m, 3H), 3.95 (s, 3H), 3.90 (s, 3H), 3.00 (t, 2H), 1.67 (s, 2H).

EXAMPLE 201

4-(2,5-Dimethyl-4-hydroxyanilino)-2-(3-pyridinyl)-6-trifluoromethylpyrimidine

The title compound was prepared from 4-chloro-2-(3-pyridinyl)-6-trifluoromethylpyrimidine (50 mg, 0.192 mmol) and 2,5-dimethyl-4-hydroxyaniline (40 mg, 0.288 mmol) similar to Example 190 and was isolated as a solid. $^1$H NMR (CDCl$_3$): 9.51 (brs, 1H), 8.72 (d, J=8.4 Hz, 1H), 8.63 (d, J=3.6 Hz, 1H), 7.45 (dd, J=7.5, 3.5 Hz, 1H), 7.33 (s, 1H), 7.00 (s, 1H), 6.74 (s, 1H), 6.45 (brs, 1H), 2.25 (s, 3H), 2.16 (s, 3H).

EXAMPLE 202

4-(3,4,5-Trichloroanilino)-2-(3-pyridinyl)-6-trifluoromethylpyrimidine

The title compound was prepared from 4-chloro-2-(3-pyridinyl)-6-trifluoromethylpyrimidine (50 mg, 0.192 mmol) and 3,4,5-trichloroaniline (56 mg, 0.288 mmol) similar to Example 180 and was isolated as a white solid (30 mg, 37%). $^1$H NMR (CDCl$_3$): 9.58 (d, J=1.5 Hz, 1H), 8.99 (ddd, J=8.4, 4.9, 1.5 Hz, 1H), 8.79 (dd, J=5.4, 1.5 Hz, 1H), 7.99 (s, 1H), 7.76 (dd, J=7.8, 5.1 Hz, 1H), 7.40 (s, 1H).

EXAMPLE 203

4-(2-Cyano-4,5-dimethoxyanilino)-2-(3-pyridinyl)-6-trifluoromethylpyrimidine

The title compound was prepared from 4-chloro-2-(3-pyridinyl)-6-trifluoromethylpyrimidine (50 mg, 0.192 mmol) and 2-cyano-4,5-dimethoxyaniline (48 mg, 0.288 mmol) similar to Example 185 and isolated as a solid (8 mg, 10%). $^1$H NMR (CDCl$_3$): 9.62 (d, J=1.4 Hz, 1H), 8.69 (m, 2H), 7.43 (dd, J=5.4, 1.5 Hz, 1H), 7.07 (s, 1H), 6.93 (s, 1H), 6.70 (s, 1H).

EXAMPLE 204

4-(3-Methoxy-dibenzofuran-4-ylamino)-2-(3-pyridinyl)-6-trifluoromethylpyrimidine The title compound was prepared from 4-chloro-2-(3-pyridinyl)-6-trifluoromethylpyrimidine (50 mg, 0.192 mmol) and 4-amino-3-methoxydibenzofuran (61 mg, 0.288 mmol) similar to Example 185 and was isolated as a solid (6 mg, 7%). $^1$H NMR (CDCl$_3$): 9.73 (brs, 1H), 8.88 (d, J=7.8 Hz, 1H), 8.77 (brs, 1H), 7.89 (m, 1H), 7.19–7.59 (m, 6H), 7.02 (s, 1H), 4.05 (s, 3H).

EXAMPLE 205

4-(1,5,6-Trimethyl-benzimidazol-4-ylamino)-2-(3-pyridinyl)-6-trifluoromethylpyrimidine The title compound was prepared from 4-chloro-2-(3-pyridinyl)-6-trifluoromethylpyrimidine (50 mg, 0.192 mmol) and 1,5,6-trimethyl-4-aminobenzimidazole (50 mg, 0.288 mmol) similar to Example 185 and was isolated as a solid (5 mg, 6%). $^1$H NMR (CDCl$_3$): 9.36 (ddd, J=7.8, 3.0, 1,2 Hz, 1H), 9.68 (s, 1H), 9.01 (ddd, J=5.7, 2.7, 1.2 Hz, 1H), 8.87 (s, 1H), 8.46 (dd, J=8.4, 6.0 Hz, 1H), 8.04 (s, 1H), 7.71 (s, 1H), 7.48 (s, 1H), 6.93 (s, 1H), 2.62 (s, 3H), 2.24 (s, 3H), 2.21 (s, 3H).

EXAMPLE 206

4-(2,6-Dimethoxypyridin-3-ylamino)-2-(3-pyridinyl)-6-trifluoromethylpyrimidine

The title compound was prepared from 4-chloro-2-(3-pyridinyl)-6-trifluoromethylpyrimidine (50 mg, 0.192 mmol) and 3-amino-2,6-dimethoxypyridine (44 mg, 0.288 mmol) similar to Example 180 and was isolated as a yellow solid (15 mg, 20%). $^1$H NMR (CDCl$_3$): 9.62 (brs, 1H), 8.72–8.67 (m, 2H), 7.42 (dd, J=8.1, 5.4 Hz, 1H), 7.09 (s, 1H), 6.75 (s, 1H), 6.43 (d, J=8.7 Hz, 1H), 4.08 (s, 3H), 4.02 (s, 3H).

EXAMPLE 207

4-(2-Methoxy-pyridin-5-ylamino)-2-(3-pyridinyl)-6-trifluoromethylpyrimidine

The title compound was prepared from 4-chloro-2-(3-pyridinyl)-6-trifluoromethylpyrimidine (50 mg, 0.192 mmol) and 5-amino-2-methoxypyridine (35 mg, 0.288 mmol) similar to Example 180 and was isolated as a solid (30 mg, 45%). $^1$H NMR (CDCl$_3$): 9.65 (brs, 1H), 8.72–8.69 (m, 2H), 8.26 (d, J=2.7 Hz, 1H), 7.71 (d, J=6.9 Hz, 1H), 7.44–7.40 (m, 2H), 6.86 (d, J=9.0 Hz, 1H), 6.74 (s, 1H), 3.98 (s, 3H).

EXAMPLE 208

4-(4,6-Dimethoxy-pyrimidin-2-ylamino)-2-(3-pyridinyl)-6-trifluoromethylpyrimidine The title compound was prepared from 4-chloro-2-(3-pyridinyl)-6-trifluoromethylpyrimidine (50 mg, 0.192 mmol) and 2-amino-4,6-dimethoxypyrimidine (27 mg, 0.288 mmol) similar to Example 190 and was isolated as a solid. $^1$H NMR (CDCl$_3$): 9.65 (brs, 1H), 8.71–8.70 (m, 2H), 7.54 (brs, 1H), 7.44 (dd, J=7.8, 4.8 Hz, 1H), 7.25 (s, 1H), 7.04 (s, 1H), 6.07 (t, J=5.4 Hz, 1H).

EXAMPLE 209

4-(5-Chloro-2-methyl-pyrimidin-4-ylamino)-2-(3-pyridinyl)-6-trifluoromethylpyrimidine The title compound was prepared from 4-chloro-2-(3-pyridinyl)-6-trifluoromethylpyrimidine (50 mg, 0.192 mmol) and 4-amino-5-chloro-2-methylpyrimidine (42 mg, 0.288 mmol) similar to Example 190 and was isolated as a solid. $^1$H NMR (CDCl$_3$): 9.58 (d, J=1.5 Hz, 1H), 8.72–8.65 (m, 2H), 7.42 (dd, J=6, 5.1 Hz, 1H), 6.70 (s, 1H), 5.32 (s, 2H), 1.70 (s, 3H).

EXAMPLE 210

4-(2-Hydroxy-5-methyl-pyrimidin-4-ylamino)-2-(3-pyridinyl)-6-trifluoromethylpyrimidine The title compound was prepared from 4-chloro-2-(3-pyridinyl)-6-trifluoromethylpyrimidine (50 mg, 0.192 mmol) and 4-amino-2-hydroxy-5-methylpyrimidine (36 mg, 0.288 mmol) similar to Example 190 and was isolated as a solid. $^1$H NMR (CDCl$_3$): 9.47 (brs, 1H), 8.59–8.54 (m, 2H), 7.28 (dd, J=8.1, 5.1 Hz, 1H), 6.59 (s, 1H), 5.18 (s, 2H), 1.70 (s, 3H).

EXAMPLE 211

4-(1,3,4-Triazol-1-ylamino)-2-(3-pyridinyl)-6-trifluoromethylpyrimidine

The title compound was prepared from 4-chloro-2-(3-pyridinyl)-6-trifluoromethylpyrimidine (50 mg, 0.192 mmol) and 1-amino-1,3,4-triazole (24 mg, 0.288 mmol) similar to Example 190 and was isolated as a solid. $^1$H NMR (CDCl$_3$): 9.61 (brs, 1H), 8.71–8.66 (m, 4H), 7.41 (m, 2H), 6.69 (s, 1H), 5.18 (s, 2H).

EXAMPLE 212

4-(Indol-4-ylamino)-2-(2-pyridinyl)-6-trifluoromethylpyrimidine

The title compound was prepared from 4-chloro-2-(3-pyridinyl)-6-trifluoromethylpyrimidine (50 mg, 0.192 mmol) and 4-aminoindole (37 mg, 0.288 mmol) similar to Example 180 and was isolated as a solid (55 mg, 80%). $^1$H NMR (CDCl$_3$): 8.76 (brs, 1H), 8.58 (d, J=8.1 Hz, 1H), 7.93 (t, J=7.5 Hz, 1H), 7.51–7.39 (m, 3H), 7.28–7.16 (m, 3H), 6.94 (s, 1H), 6.45 (s, 1H).

EXAMPLE 213

4-(2-Methyl-indol-5-ylamino)-2-(3-pyridinyl)-6-trifluoromethylpyrimidine

The title compound was prepared from 4-chloro-2-(3-pyridinyl)-6-trifluoromethylpyrimidine (50 mg, 0.192 mmol) and 5-amino-2-methylindole (41 mg, 0.288 mmol) similar to Example 190 and was isolated as a solid. $^1$H NMR (CDCl$_3$): 9.66 (s, 1H), 8.75–8.72 (m, 2H), 8.08 (s, 1H), 7.46–7.34 (m, 4H), 7.10 (d, J=8.4 Hz, 1H), 6.78 (s, 1H), 6.45 (s, 1H).

EXAMPLE 214

4-(2-Chloro-5-methoxy-anilino)-2-(2-pyrimidinyl)-6-trifluoromethylpyrimidine hydrochloride a. 2-Amidinopyrimidine: A solution of 2-cyanopyrimidine (4 g, 38.06 mmol) in 7N ammonia in methanol (300 ml) was stirred at room temperature for 48 h. The mixture was rotary evaporated to dryness. The residue was washed with hexane, filtered, and dried under vacuo to give a pale white solid (3.5 g, 76%). $^1$H NMR (DMSO-d$_6$): 8.96 (d, J=4.8 Hz, 2H), 7.63 (t, J=4.8 Hz, 1H), 7.10 (bs, 3H).

b. 2-(2-Pyrimidinyl)-6-trifluoromethylpyrimidin-4-ol: To a stirring solution of ethanolic sodium ethoxide (100 mg of sodium ethoxide in 20 ml of ethanol) was added 2-amidinopyrimidine (500 mg, 4.09 mmol) and ethyl 4,4,4-trifluoroacetoacetate (897 ul, 6.14 mmol). The mixture was refluxed for 24 h. The mixture was cooled to room temperature and then rotary evaporated to dryness. To the residue was added water (40 ml) and the mixture was extracted with chloroform (2×60 ml). The chloroform solution was dried over anhydrous sodium sulfate and then concentrated in vacuo. The residue was purified by column chromatography to give the product as a yellow solid (350 mg, 35%). $^1$H NMR (CDCl$_3$): 11.21 (s, 1H), 9.04 (d, J=5.1 Hz, 2H), 7.58 (t, J=5.1 Hz, 1H), 6.98 (s, 1H).

c. 4-Chloro-2-(2-pyrimidinyl)-6-trifluoromethylpyrimidine: A solution of 2-(2-pyrimidinyl)-6-trifluoromethylpyrimidin-4-ol (135 mg, 0.557 mmol) in phosphorus oxychloride (3 ml) was refluxed for 3 h. The mixture was cooled to room temperature and then rotary evaporated to leave a brown oil. The oil was extracted with ethyl acetate (75 ml), and the extracts were washed with water (2×20 ml), and dried over anhydrous sodium sulfate. The ethyl acetate solution was rotary evaporated to dryness to give a yellow solid (120 mg, 83%). $^1$H NMR (CDCl$_3$): 9.08 (d, J=4.5 Hz, 2H), 7.83 (s, 1H), 7.51 (t, J=4.5 Hz, 1H).

d. 4-(2-Chloro-5-methoxy-anilino)-2-(2-pyrimidinyl)-6-trifluoromethylpyrimidine hydrochloride: A mixture of 4-chloro-2-(2-pyrimidinyl)-6-trifluoromethylpyrimidine (50 mg, 0.192 mmol) and 2-chloro-5-methoxyaniline hydrochloride (56 mg, 0.288 mmol) in water:ethanol (2:1, 10 ml) was refluxed for 48 h. The mixture was cooled to room temperature and basified with aqueous 2N NaOH to pH 10–12. The resulting precipitate was collected by filtration and purified by column chromatography to give a yellow solid (21 mg, 28%). $^1$H NMR (CDCl$_3$): 9.01 (d, J=4.8 Hz, 2H), 7.71 (s, 1H), 7.67 (s, 1H), 7.44 (t, J=4.8 Hz, 1H), 7.36 (d, J=9.3 Hz, 1H), 7.09 (s, 1H), 6.75 (dd, J=3.0, 9.0 Hz, 1H), 3.86 (s, 3H).

EXAMPLE 215

4-(2-Chloro-5-methoxyanilino)-2-(3-pyridinyl)-6-(t-butyl)pyrimidine a. 4-Chloro-2-(3-pyridinyl)-6-(t-butyl)pyrimidine: The title compound was prepared from 6-tert-butyl-2-pyridin-3-yl-pyrimidin-4-ol (400 mg, 1.75 mmol) and phosphorus oxychloride (10 ml) similar to Example 214c and isolated as a tan solid (333 mg, 77%). $^1$H NMR (CDCl$_3$): 9.68 (d, J=1.5 Hz, 1H), 8.80–8.76 (m, 1H), 8.73 (dd, J=1.5, 4.8 Hz, 1H), 7.49–7.44 (m, 1H), 7.28 (s, 1H), 1.41 (s, 9H).

b. 4-(2-Chloro-5-methoxyanilino)-2-(3-pyridinyl)-6-(t-butyl)pyrimidine: The title compound was prepared from a mixture of 4-chloro-2-(3-pyridinyl)-6-(tert-butyl)pyrimidine (50 mg, 0.202 mmol) and 2-chloro-5-methoxyaniline hydrochloride (59 mg, 0.303 mmol) similar to Example 117 and isolated as a yellow oil (12 mg, 15%). $^1$H NMR (CDCl$_3$): 9.70 (s, 1H), 8.75–8.68 (m, 2H), 8.13 (d, J=2.7 Hz, 1H), 7.42–7.39 (m, 1H), 7.31 (d, J=8.7 Hz, 1H), 7.11 (s, 1H), 6.65 (s, 1H), 6.60 (dd, J=3.0, 8.7 Hz, 1H), 3.87 (s, 3H), 1.39 (s, 9H).

EXAMPLE 216

4-(3-Methoxyanilino)-2-(2-piperidinyl)-6-(trifluoromethyl)pyrimidine

To a solution of 4-(3-methoxyanilino)-2-(2-pyridinyl)-6-(trifluoromethyl)pyrimidine (50 mg, 0.144 mmol) in methanol (20 ml) was added concentrated hydrochloric acid (200 ul). The mixture was hydrogenated over palladium (5 wt % on activated carbon) at 50 psi for 6 h. The mixture was filtered through Celite. The filtrate was rotary evaporated to dryness and purified by column chromatography to give a brown oil (3 mg, 6%). $^1$H NMR (CDCl$_3$): 7.83 (s, 1H), 7.31 (d, J=7.8 Hz, 1H), 6.90–6.85 (m, 3H), 6.77 (dd, J=1.8, 7.8 Hz, 1H), 3.90 (dd, J=3.0, 10.5 Hz, 1H), 3.81 (s, 3H), 3.29 (d, J=11.4 Hz, 1H), 2.88–2.80 (m, 2H), 2.25 (d, J=10.5 Hz, 1H), 1.92 (s, 1H), 1.69–1.56 (m, 4H).

EXAMPLE 217

4-(2-Chloro-5-methoxyanilino)-2-(4-pyridinyl-N-oxide)-6-(trifluoromethyl)pyrimidine To a stirring solution of 4-(2-chloro-5-methoxyanilino)-2-(4-pyridinyl)-6-(trifluoromethyl)pyrimidine (50 mg, 0.131 mmol) in dichloromethane (5 ml) was added m-chloroperbenzoic acid (23 mg, 0.131 mmol). The mixture was stirred at room temperature for 30 minutes and then rotary evaporated to dryness. The residue was purified by column chromatography to give a white solid (19 mg, 36%). $^1$H NMR (CDCl$_3$): 8.35 (d, J=7.5 Hz, 2H), 8.28 (d, J=7.5 Hz, 2H), 7.64 (d, J=2.4 Hz, 1H), 7.40 (d, J=9.0 Hz, 1H), 7.30 (s, 1H), 6.94 (s, 1H), 6.76 (dd, J=3.0, 9.0 Hz, 1H), 3.85 (s, 3H).

EXAMPLE 218

4-(4-Chloro-2-methoxy-5-methylanilino)-2-(3-pyridinyl)-6-(trifluoromethyl)pyrimidine The title compound was prepared from a mixture of 4-chloro-2-(3-pyridinyl)-6-(trifluoromethyl)pyrimidine (50 mg, 0.193 mmol) and 4-chloro-2-methoxy-5-methylaniline (50 mg, 0.289 mmol) similar to Example 117 and isolated as a tan solid (26 mg, 34%). $^1$H NMR (CDCl$_3$): 9.65–9.63 (m, 1H), 8.75–8.70 (m, 2H), 8.18 (s, 1H), 7.46–7.41 (m, 1H), 7.36 (s, 1H), 6.97 (s, 1H), 6.87 (s, 1H), 3.91 (s, 3H), 2.42 (s, 3H).

EXAMPLE 219

4-(2,4,5-Trimethylanilino)-2-(3-pyridinyl)-6-(trifluoromethyl)pyrimidine a. 2,4,5-Trimethylphenylamine: A solution of 5-nitropseudocumene (400 mg, 2.42 mmol) in methanol (30 ml) was hydrogenated over palladium (5 wt % on activated carbon) at 50 psi for 3 h. The mixture was filtered through Celite. The filtrate was rotary evaporated to leave a light purple residue (246 mg, 75%). $^1$H NMR (CDCl$_3$): 6.82 (s, 1H), 6.50 (s, 1H), 3.42 (s, 2H), 2.16 (s, 3H), 2.14 (s, 3H), 2.11 (s, 3H).

b. 4-(2,4,5-Trimethylanilino)-2-(3-pyridinyl)-6-(trifluoromethyl)pyrimidine: The title compound was prepared from a mixture of 4-chloro-2-(3-pyridinyl)-6-(trifluoromethyl)pyrimidine (50 mg, 0.193 mmol) 2,4,5-trimethylphenylamine (39 mg, 0.289 mmol) similar to Example 117 and isolated as a yellow solid (21 mg, 30%). $^1$H NMR (CDCl$_3$): 9.70 (d, J=1.8 Hz, 1H), 8.73–8.70 (m, 1H), 8.67 (dd, J=1.5, 4.8 Hz, 1H), 7.65 (s, 1H), 7.42–7.38 (m, 1H), 7.11 (s, 1H), 7.10 (s, 1H), 6.51 (s, 1H), 2.29 (s, 3H), 2.27 (s, 3H), 2.22 (s, 3H).

EXAMPLE 220

4-(2,4-Dichloro-5-hydroxyanilino)-2-(3-pyridinyl)-6-(trifluoromethyl)pyrimidine

The title compound was prepared from a mixture of 4-chloro-2-(3-pyridinyl)-6-(trifluoromethyl)pyrimidine (50 mg, 0.193 mmol) and 5-amino-2,4-dichlorobenzenol (51 mg, 0.289 mmol) similar to Example 117 and isolated as a white solid (24 mg, 31%). $^1$H NMR (DMSO-d$_6$): 10.80 (s, 1H), 9.90 (s, 1H), 9.39–9.38 (m, 1H), 8.75–8.72 (m, 1H), 8.57–8.53 (m, 1H), 7.63 (s, 1H), 7.61 (s, 1H), 7.59–7.55 (m, 1H), 7.31 (s, 1H).

EXAMPLE 221

Identification of 4-(3-Methoxyanilino)-2-(2-pyridinyl)-6-(trifluoromethyl)pyrimidine and Analogs as Caspase Cascade Activators and Inducers of Apoptosis in Solid Tumor Cells Human breast cancer cell lines T-47D and ZR-75-1 were grown according to media component mixtures designated by American Type Culture Collection+10% FCS (Invitrogen Corporation, Life Technologies division), in a 5% CO$_2$-95% humidity incubator at 37° C. T-47D and ZR-75-1 cells were maintained at a cell density between 50 and 80% confluency at a cell density of 0.1 to 0.6×10$^6$ cells/ml. Cells were harvested at 600×g and resuspended at 0.65×10$^6$ cells/ml into appropriate media+10% FCS. An aliquot of 45 μl of cells was added to a well of a 96-well microtiter plate containing 2.5 μl of a 10% DMSO in RPMI-1640 media solution containing 0.16 to 100 μM of 4-(3-methoxyanilino)-2-(2-pyridinyl)-6-(trifluoromethyl)pyrimidine or other test compound (0.016 to 10 μM final). An aliquot of 22.5 μl of cells was added to a well of a 384-well microtiter plate containing 2.5 μl of a 10% DMSO in RPMI-1640 media solution without test compound as the control sample. The samples were mixed by agitation and then incubated at 37° C. for 48 h in a 5% $CO_2$-95% humidity incubator. After incubation, the samples were removed from the incubator and 25 μl of a solution containing 14 μM of N-(Ac-DEVD)-N'-ethoxycarbonyl-R110 fluorogenic substrate (Cytovia, Inc.; WO99/18856), 20% sucrose (Sigma), 20 mM DTT (Sigma), 200 mM NaCl (Sigma), 40 mM Na PIPES buffer pH 7.2 (Sigma), and 500 μg/ml lysolecithin (Calbiochem) was added. The samples were mixed by agitation and incubated at room temperature. Using a fluorescent plate reader (Model SpectraMax Gemini, Molecular Devices), an initial reading (T=0) was made approximately 1–2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$$RFU_{(T=3h)} - \text{Control } RFU_{(T=0)} = \text{Net } RFU_{(T=3h)}$$

The activity of caspase cascade activation was determined by the ratio of the net RFU value for 4-(3-methoxyanilino)-2-(2-pyridinyl)-6-(trifluoromethyl)pyrimidine or other test compound to that of control samples. The $EC_{50}$ (nM) was determined by a sigmoidal dose-response calculation (Prism 2.0, GraphPad Software Inc.). The caspase activity (Ratio) and potency ($EC_{50}$) are summarized in Table I:

TABLE I

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| A | 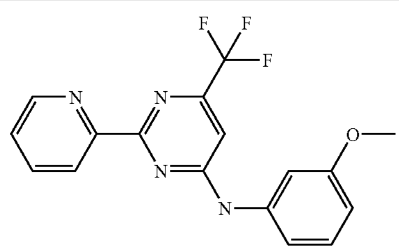 | 29.3 | 433 | 3.6 | 140 |
| 19 | 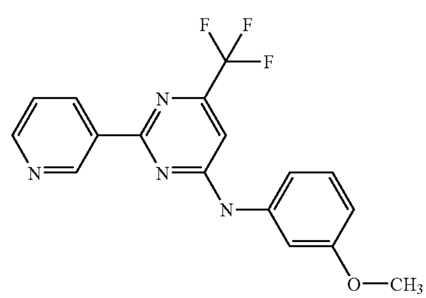 | 16.7 | 471 | 8.9 | 214 |
| 41 | 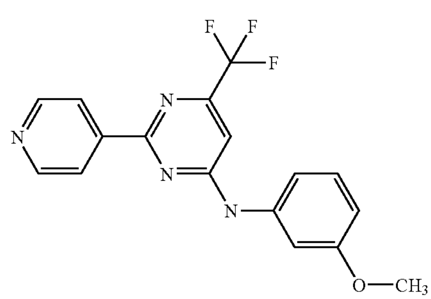 | 7.5 | 521 | 1.6 | >5000 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
| --- | --- | --- | --- | --- | --- |
| 74 | 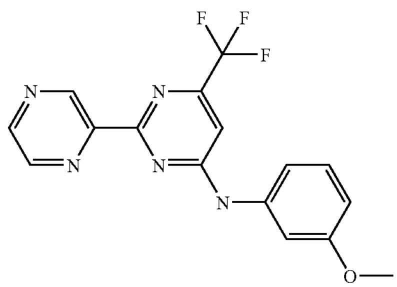 | 16.4 | 364 | 13.1 | 326 |
| 73 | 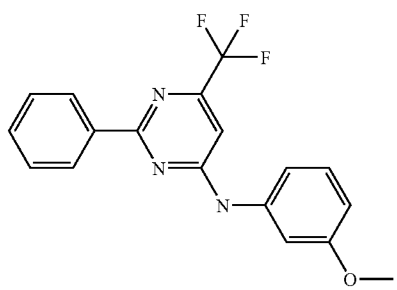 | 1.6 | >5000 | 2.6 | 10000 |
| 131 | 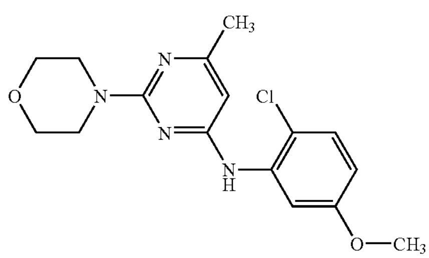 | 1.2 | >5000 | 1.2 | >5000 |
| 164 | 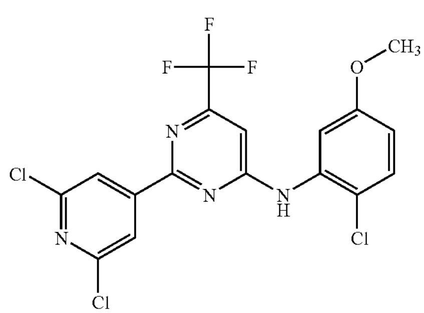 | 1.3 | >5000 | 1.3 | >5000 |
| 125 | 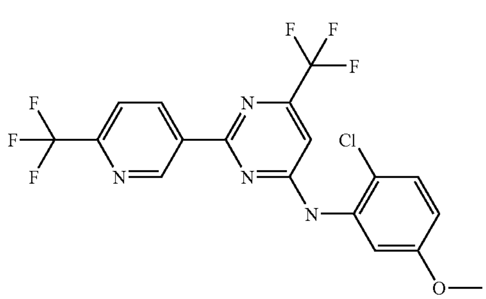 | 4.4 | 3467 | 8.1 | 2239 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 163 | 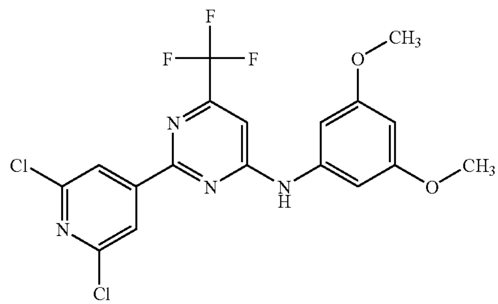 | 1.1 | >5000 | 1.6 | >5000 |
| 75 | 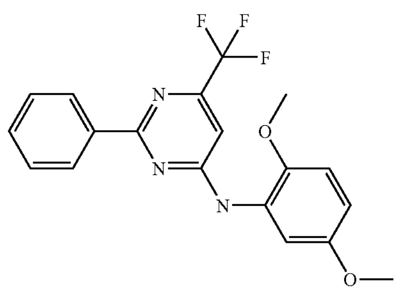 | 16.3 | 2292 | 7.8 | 3276 |
| 81 | 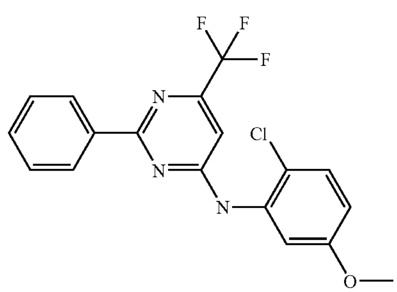 | 12.7 | 5052 | 5.0 | 5497 |
| 44 | 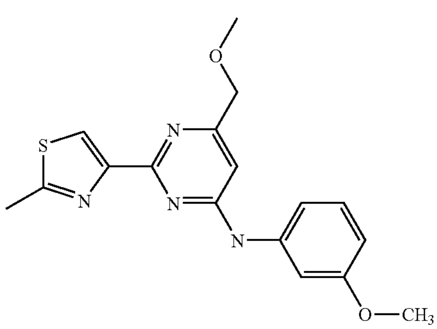 | 1.6 | >5000 | 1.9 | >5000 |

TABLE I-continued
CASPASE ACTIVITY AND POTENCY
| Compd # | Structure | T47 Ratio 48 hr | T47 EC50 (nM) | ZR Ratio 48 hr | ZR EC50 (nM) |
|---|---|---|---|---|---|
| 45 | 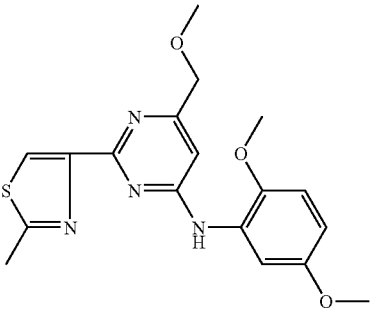 | 21.6 | 329 | 17.3 | 387 |
| 16 | 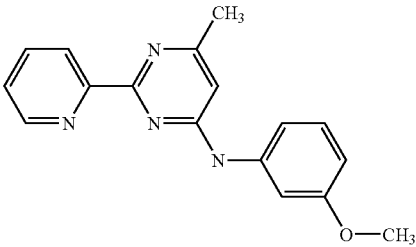 | 19.5 | 288 | 3.3 | 292 |
| 109 | 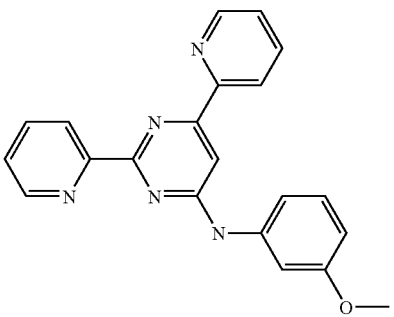 | 3.9 | 1495 | 3.6 | 2594 |
| 110 | 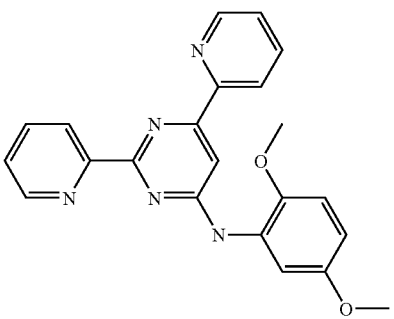 | 8.9 | 576 | 11.6 | 648 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 111 | 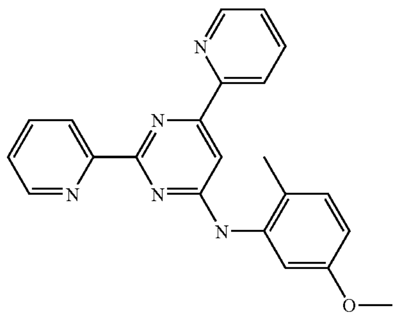 | 4.0 | 1421 | 3.9 | 2569 |
| 112 | 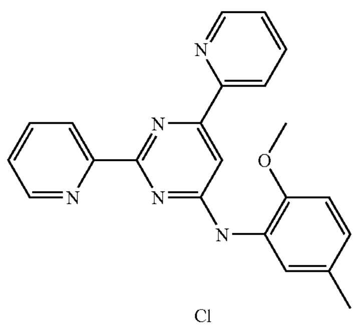 | 3.3 | 1860 | 2.9 | 2371 |
| 113 | 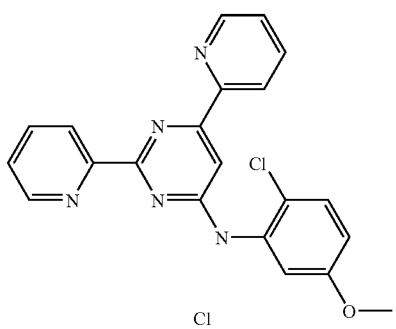 | 4.4 | 1426 | 4.1 | 2733 |
| 114 | 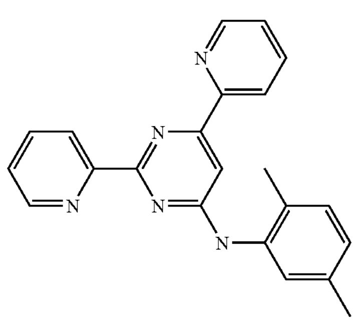 | 3.6 | 2539 | 3.7 | 2800 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 15 | 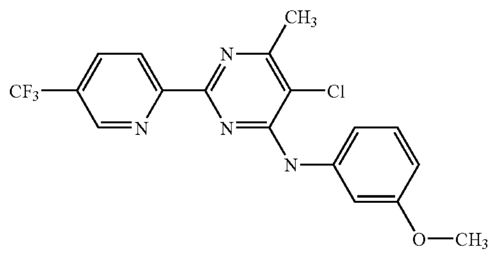 | 2.5 | >5000 | 2.7 | >5000 |
| 18 | 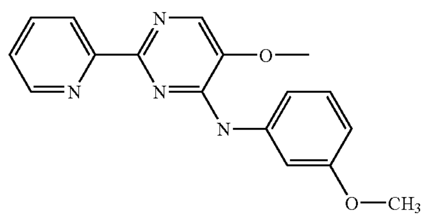 | 1.9 | >5000 | 7.8 | 4901 |
| 46 | 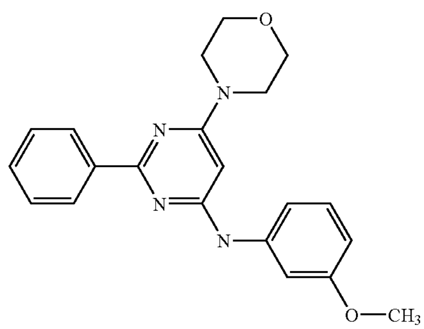 | 1.5 | >5000 | 1.4 | >5000 |
| 20 | 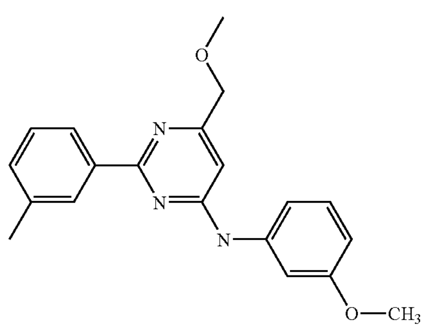 | 1.6 | >5000 | 1.1 | >5000 |
| 160 | 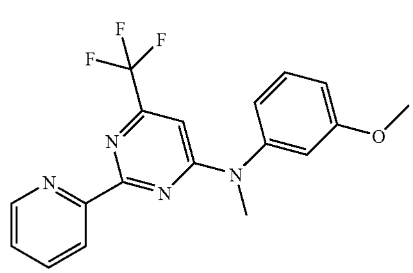 | 1.0 | >5000 | 1.4 | >5000 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 104 | 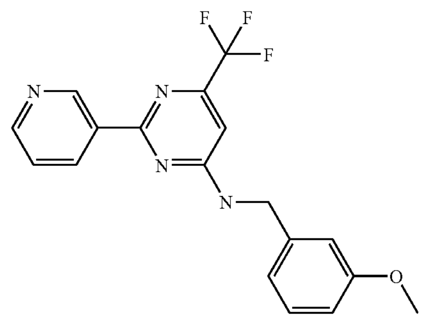 | 1.1 | >5000 | 1.7 | >5000 |
| 200 | 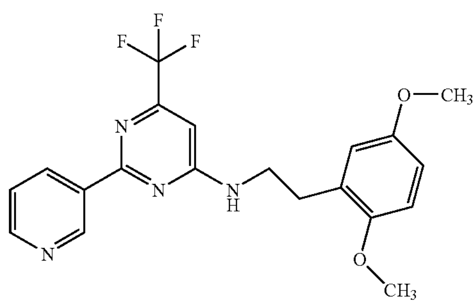 | 1.2 | >5000 | 1.4 | >5000 |
| 69 | 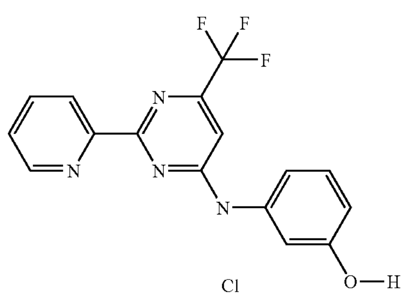 | 14.2 | 382 | 10.9 | 127 |
| 92 | 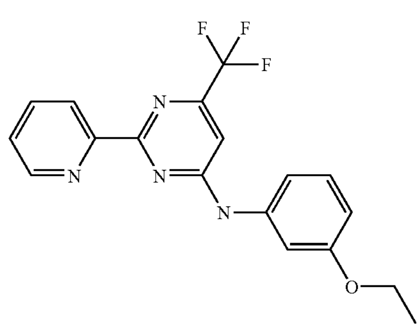 | 16.8 | 363 | 12.4 | 285 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 156 | 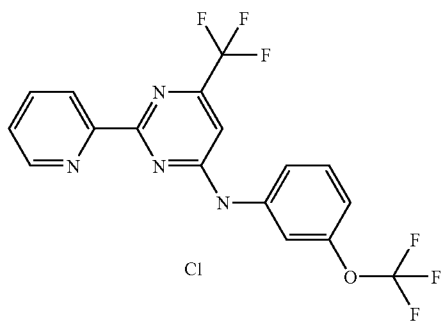 | 1.7 | >5000 | 4.1 | 2261 |
| 96 | 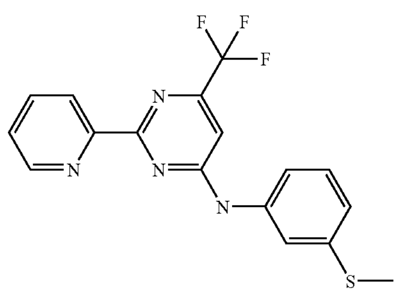 | 1.4 | >5000 | 4.9 | 2759 |
| 93 | 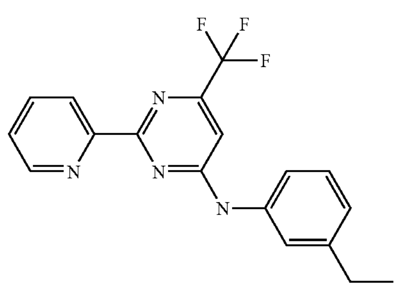 | 2.0 | >5000 | 8.2 | 2032 |
| 97 | 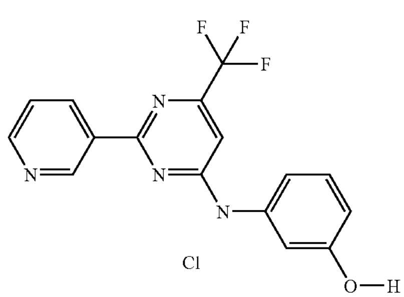 | 14.5 | 659 | 6.7 | 717 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 60 | 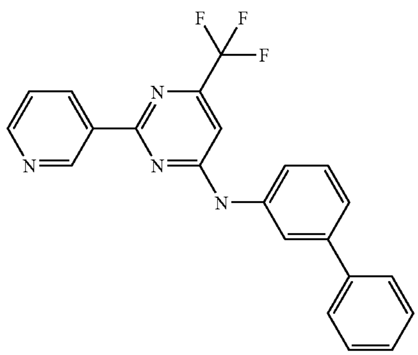 | 1.8 | >5000 | 1.4 | >5000 |
| 62 | 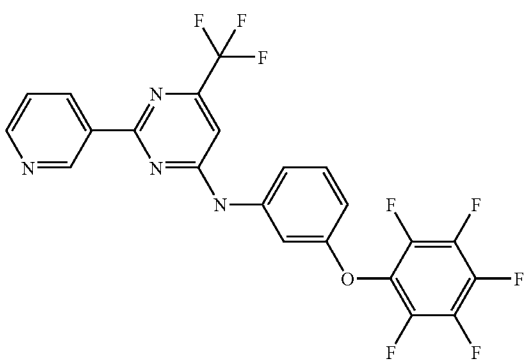 | 1.6 | >5000 | 1.3 | >5000 |
| 65 | 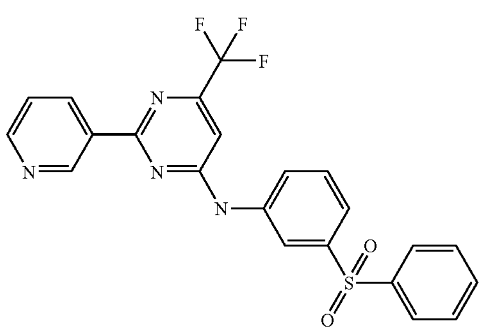 | 1.7 | >5000 | 1.7 | >5000 |
| 61 | 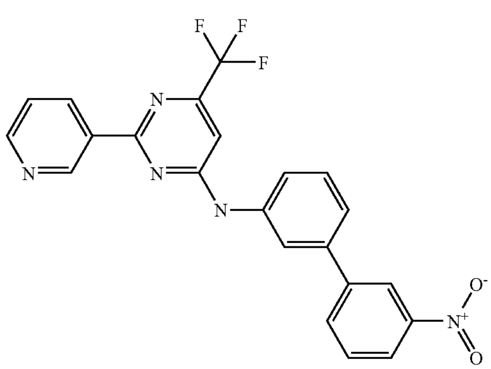 | 1.8 | >5000 | 1.2 | >5000 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 59 | 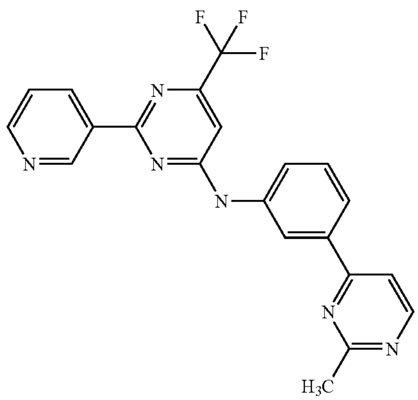 | 1.6 | >5000 | 1.1 | >5000 |
| 58 | 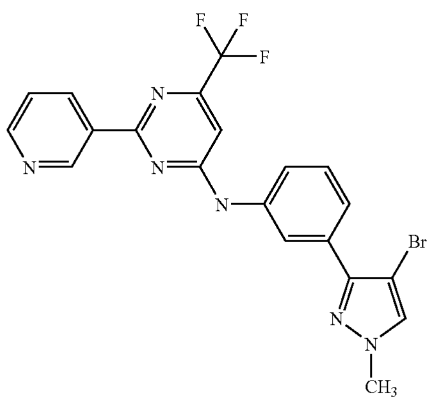 | 1.5 | >5000 | 1.1 | >5000 |
| 66 | 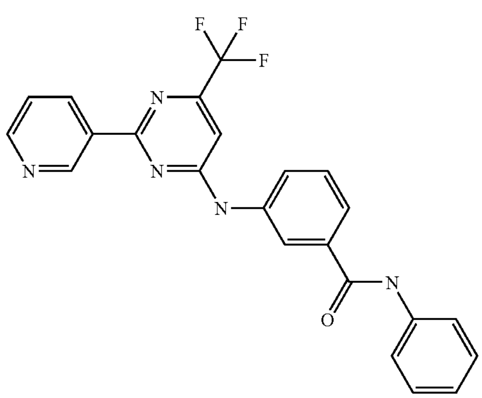 | 1.2 | >5000 | 0.9 | >5000 |
| 67 | 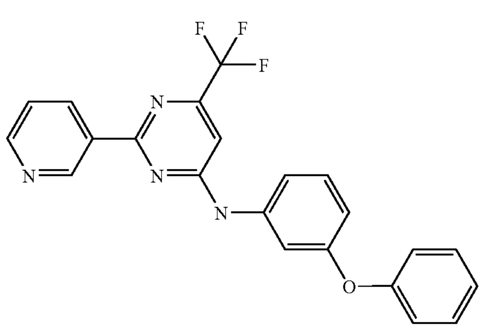 | 1.5 | >5000 | 1.2 | >5000 |

TABLE I-continued
CASPASE ACTIVITY AND POTENCY
| Compd # | Structure | T47 Ratio 48 hr | T47 EC50 (nM) | ZR Ratio 48 hr | ZR EC50 (nM) |
|---|---|---|---|---|---|
| 63 | 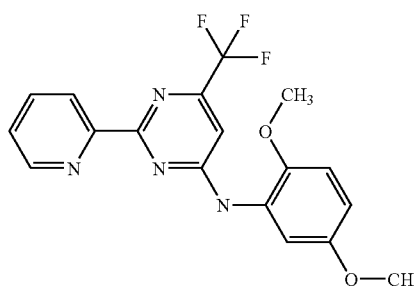 | 8.9 | 18 | 9.6 | 43 |
| 38 | 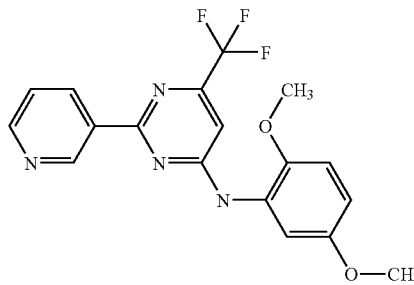 | 8.8 | 19 | 12.4 | 69 |
| 42 | 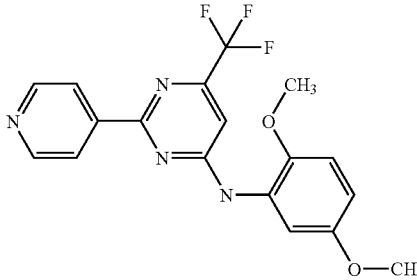 | 5.8 | 43 | 2.5 | 145 |
| 76 | 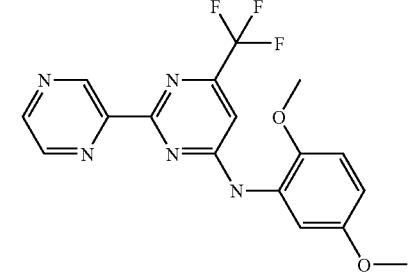 | 8.5 | <150 | ND[a] | ND |
| 102 | 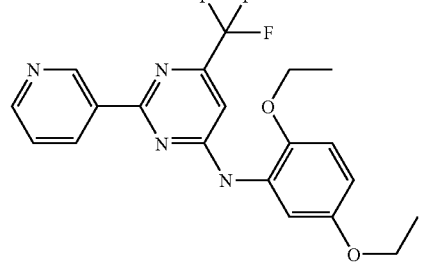 | 8.0 | 512 | 7.4 | 701 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 85 | 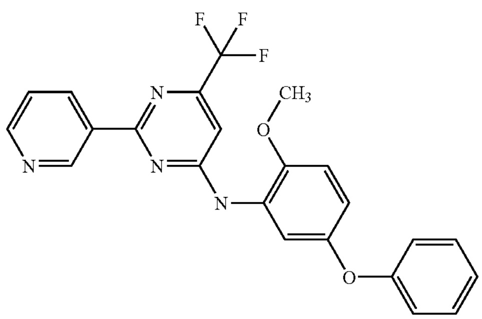 | 1.7 | >5000 | 6.7 | 2834 |
| 51 | 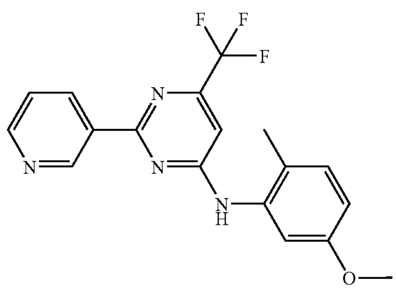 | 11 | 29 | 5.9 | 56 |
| 99 | 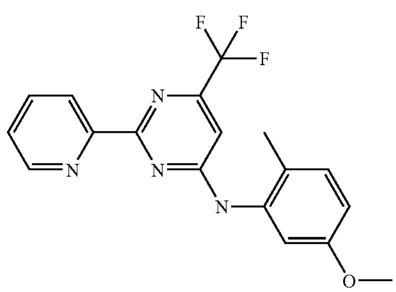 | 11.1 | 34 | 12.0 | 50 |
| 55 | 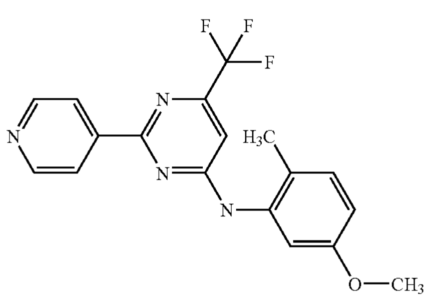 | 8.4 | 21 | 7.1 | 18 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 80 | 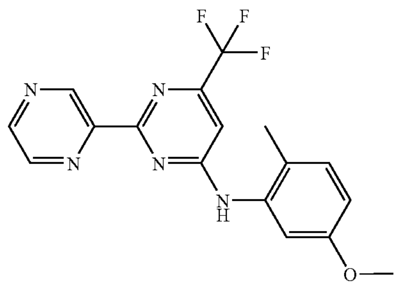 | 8.5 | 64 | 5.9 | 243 |
| 180 | 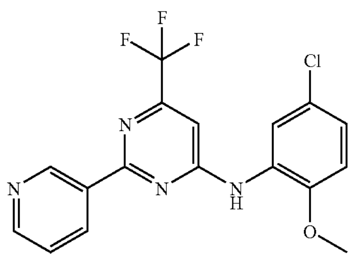 | 15.1 | 637 | 8.7 | 698 |
| 50 | 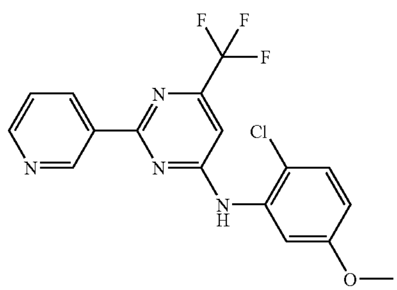 | 10 | 172 | 5.3 | 322 |
| 95 | 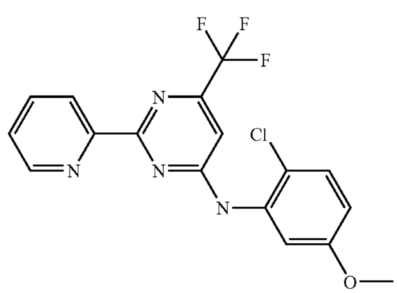 | 11.6 | 113 | 8.6 | 148 |
| 82 | 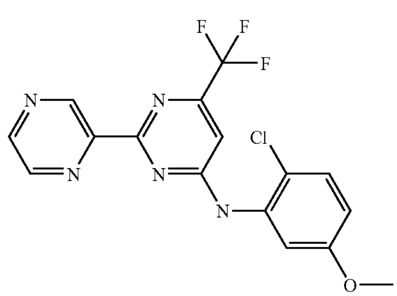 | 15.3 | 254 | ND | ND |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
| --- | --- | --- | --- | --- | --- |
| 54 | (4-pyridyl)-pyrimidine-CF3 with NH-(2-Cl,5-OMe-phenyl) | 10.5 | 99 | 5.9 | 101 |
| 127 | (3-pyridyl)-pyrimidine-CF3 with NH-(2-Br,5-OCH3-phenyl) | 10.3 | 279 | 5.3 | 550 |
| 188 | (2-pyridyl)-pyrimidine-CF3 with NH-(2-Me,5-OH-phenyl) | 3.6 | 429 | 9.3 | 271 |
| 117 | (3-pyridyl)-pyrimidine-CF3 with NH-(2-Me,5-OH-phenyl) | 11.3 | 138 | 6.3 | 276 |
| 118 | (4-pyridyl)-pyrimidine-CF3 with NH-(2-Me,5-OH-phenyl) | 8.8 | 34 | 9.9 | 31 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 194 | 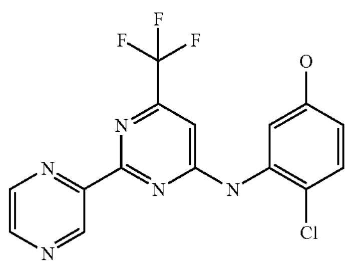 | 11.7 | 107 | ND | ND |
| 106 | 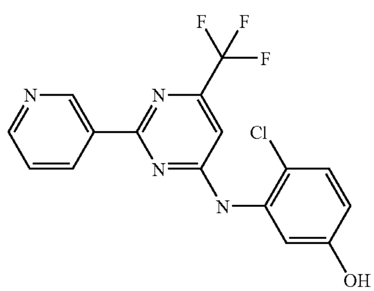 | 9.0 | 183 | 2.4 | 982 |
| 107 | 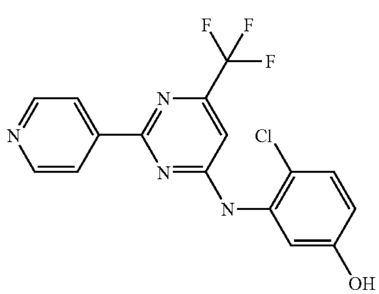 | 8.0 | 63 | 5.3 | 123 |
| 21 | 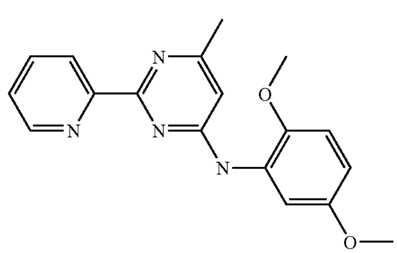 | 15.5 | <156 | 12.0 | <156 |
| 53 | 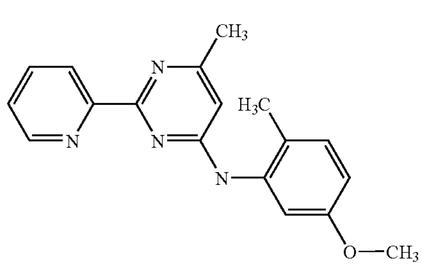 | 20.4 | 115 | 6.6 | 599 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 52 | 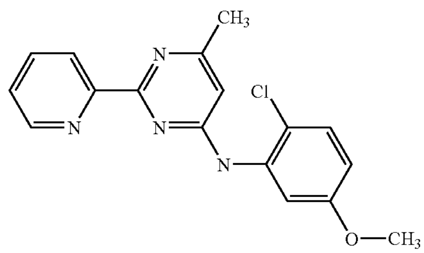 | 20.9 | 108 | 7.2 | 98 |
| 190 | 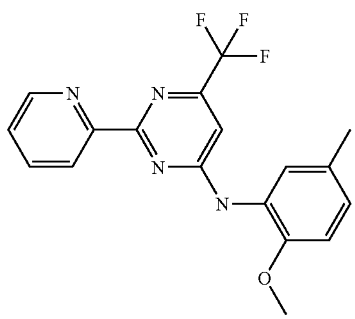 | 19.3 | 29 | 16.7 | 32 |
| 198 | 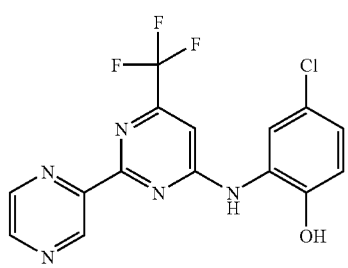 | 3.3 | 419 | 1.8 | >5000 |
| 162 | 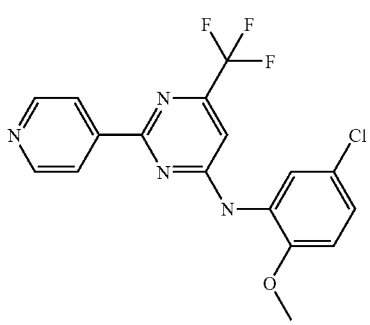 | 11.3 | 272 | 7.3 | 360 |
| 87 | 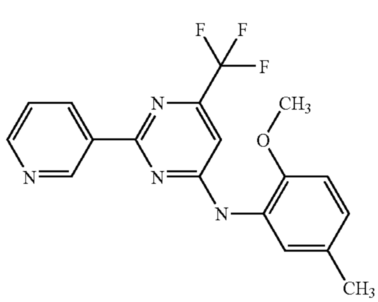 | 19.2 | <75 | 16.9 | <75 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 88 | 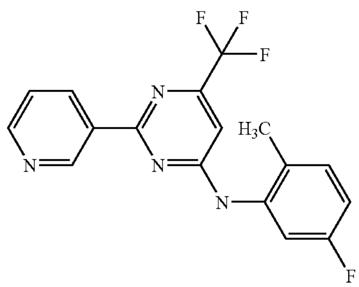 | 9.8 | 2315 | 8.0 | 1216 |
| 89 | 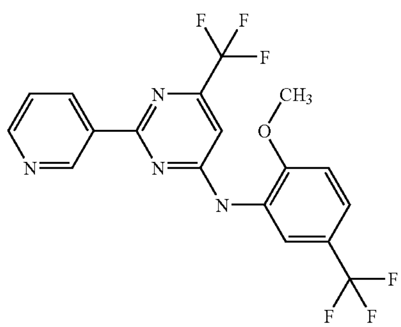 | 8.7 | 2737 | 9.8 | 1603 |
| 126 | 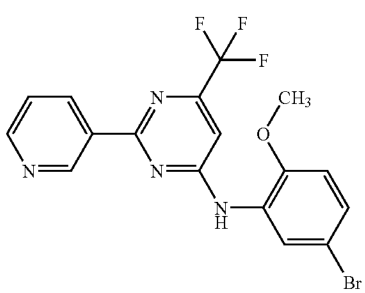 | 12.0 | 222 | 5.9 | 353 |
| 123 | 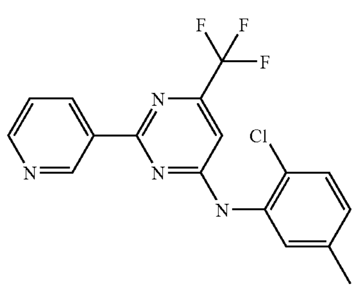 | 21.2 | 763 | 15.8 | 725 |
| 116 | 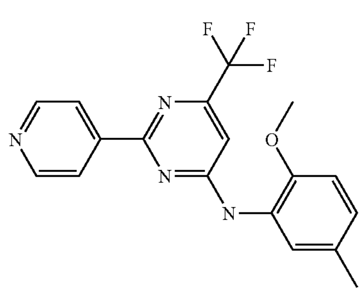 | 13.7 | 71 | 8.8 | 73 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
| --- | --- | --- | --- | --- | --- |
| 196 | 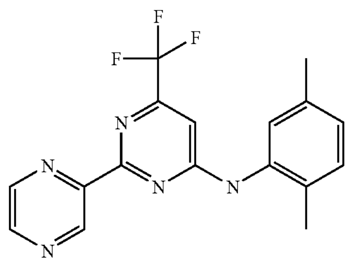 | 11.3 | 527 | ND | ND |
| 68 | 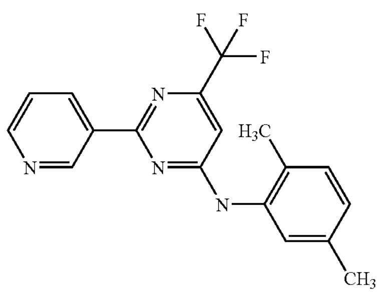 | 20.9 | 247 | 17.9 | 130 |
| 115 | 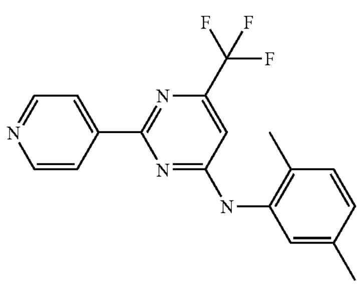 | 14.2 | 112 | 11.6 | 59 |
| 91 | 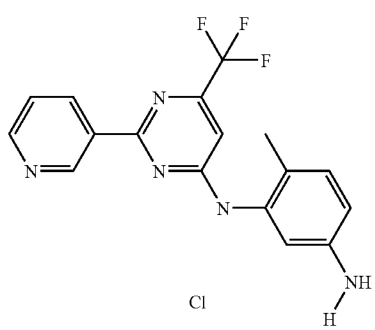 | 11.7 | 1442 | 8.8 | 788 |
| 120 | 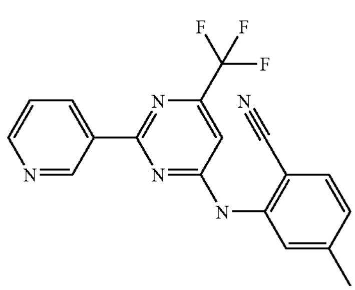 | 8.2 | 2694 | 4.5 | 2397 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 183 | 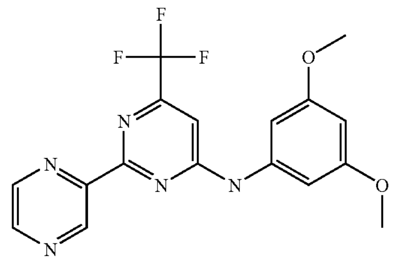 | 17.3 | 82 | 11.5 | 75 |
| 161 | 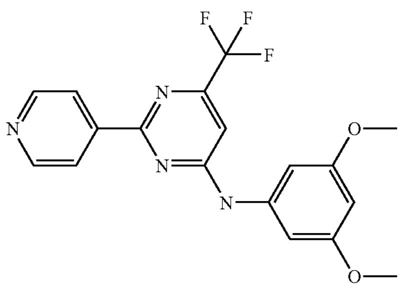 | 10.7 | 79 | 5.1 | 86 |
| 122 | 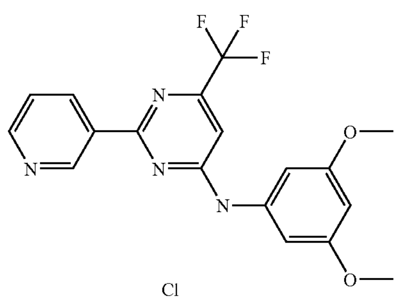 | 11.1 | 44 | 10.1 | 192 |
| 195 | 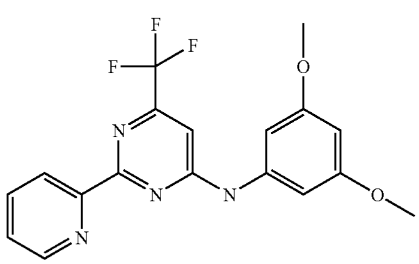 | 8.4 | 20 | ND | ND |
| 121 | 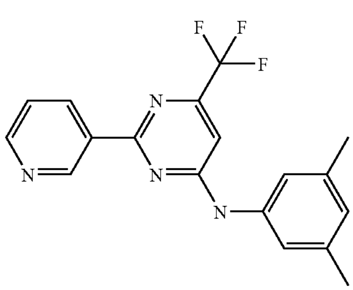 | 11.2 | 480 | 9.9 | 380 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 128 | [structure: 2-(pyridin-3-yl)-6-(trifluoromethyl)-N-(3-methyl-5-(trifluoromethyl)phenyl)pyrimidin-4-amine] | 1.4 | >5000 | 1.5 | >5000 |
| 124 | [structure: 2-(pyridin-3-yl)-6-(trifluoromethyl)-N-(3-methoxy-5-(trifluoromethyl)phenyl)pyrimidin-4-amine] | 19.9 | 720 | 16.3 | 688 |
| 176 | [structure: 6-methyl-2-(pyridin-2-yl)-N-(3,4-dimethoxyphenyl)pyrimidin-4-amine] | 4.5 | 149 | 1.9 | >5000 |
| 179 | [structure: 6-methyl-2-(pyridin-2-yl)-N-(4-fluoro-3-methoxyphenyl)pyrimidin-4-amine] | 10.8 | 1474 | 1.3 | >5000 |
| 108 | [structure: 6-methyl-2-(pyridin-2-yl)-N-(2,6-dimethylphenyl)pyrimidin-4-amine] | 0.9 | >5000 | 2.4 | 4367 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 22 | 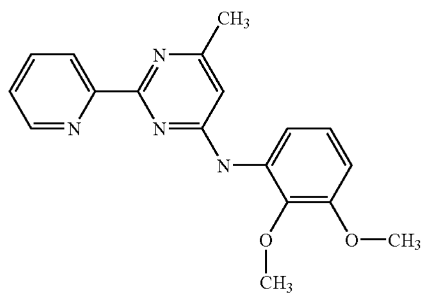 | 1.9 | >5000 | 3.5 | 6049 |
| 130 | 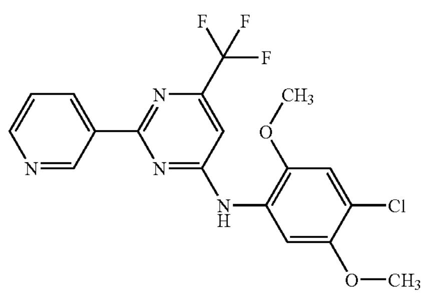 | 11.3 | 295 | 9.7 | 167 |
| 134 | 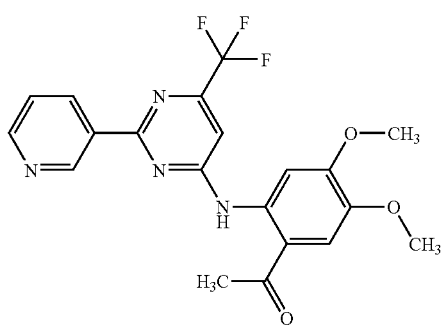 | 16.5 | 807 | 1.5 | >5000 |
| 133 | 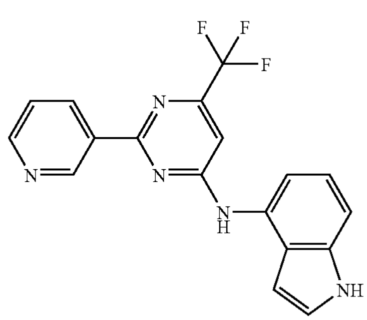 | 16.8 | 1286 | 4.5 | 354 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 157 | 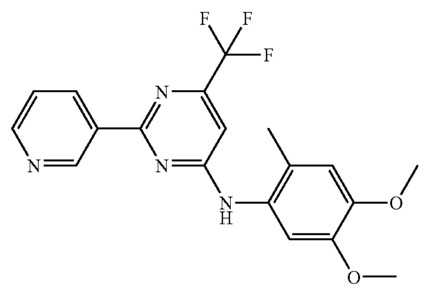 | 6.6 | 43 | 6.4 | 197 |
| 201 | 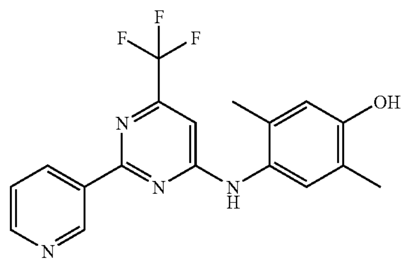 | 15.7 | 333 | 4.8 | 173 |
| 166 | 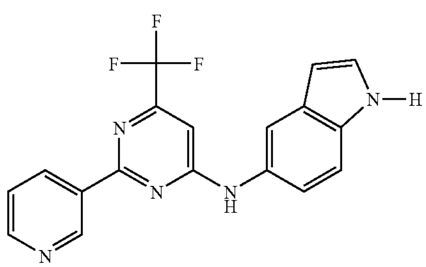 | 8.0 | 870 | 3.3 | 532 |
| 206 | 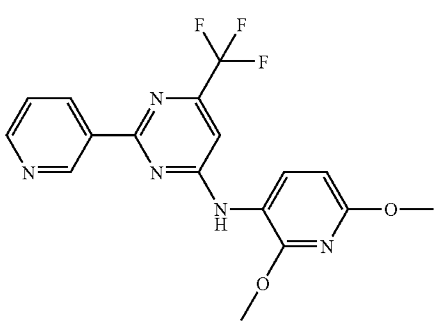 | 6.9 | 802 | 2.9 | 583 |
| 158 | 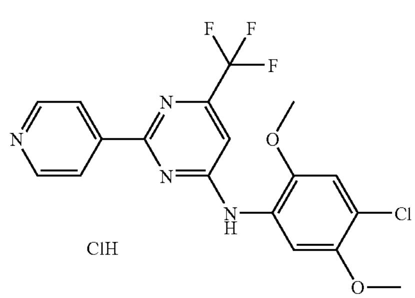 | 9.5 | 509 | 6.0 | 133 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 203 | 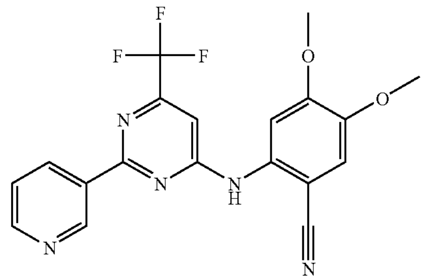 | 10.7 | 843 | 3.4 | 2627 |
| 212 | 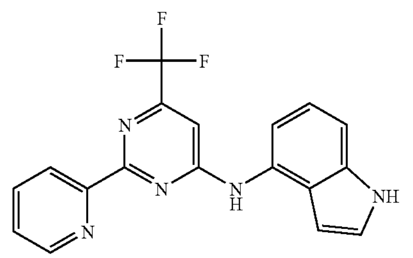 | 5.8 | 3114 | 6.1 | 2781 |
| 213 | 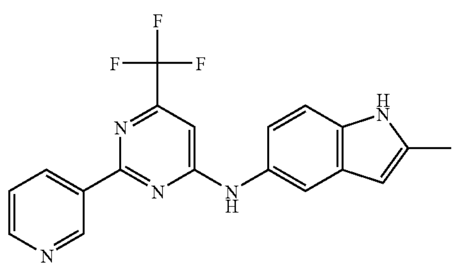 | 14.1 | 2685 | 9.9 | 1768 |
| 147 | 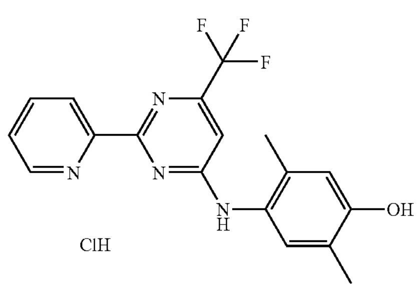 | 13.3 | 335 | 8.4 | 204 |
| 148 | 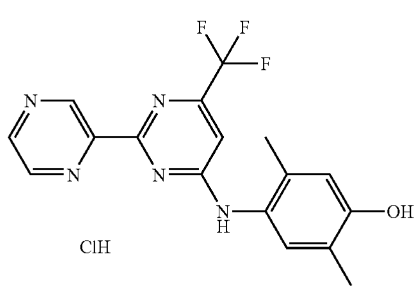 | 13.8 | 412 | 8.4 | 243 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 149 | 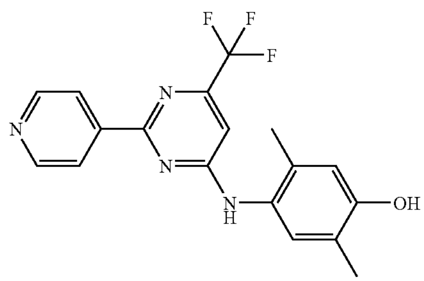 | 16.0 | 75 | 10.0 | 46 |
| 150 | 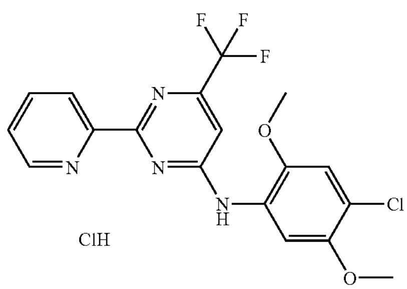 | 11.0 | 135 | 9.7 | 133 |
| 151 | 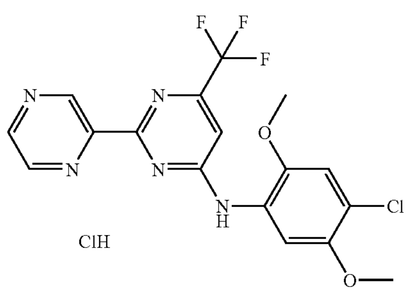 | 12.0 | 388 | 8.6 | 276 |
| 152 | 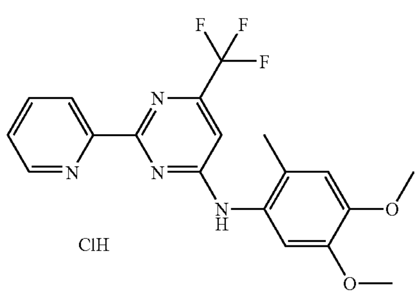 | 14.6 | 35 | 8.6 | 212 |
| 153 | 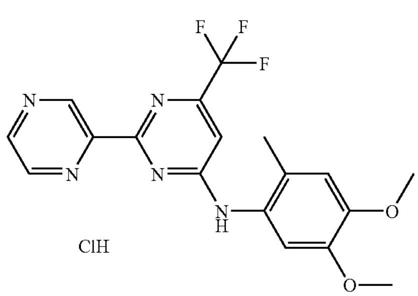 | 15.7 | 43 | 9.3 | 146 |

TABLE I-continued

CASPASE ACTIVITY AND POTENCY

| Compd # | Structure | T47 Ratio 48 hr | T47 EC50 (nM) | ZR Ratio 48 hr | ZR EC50 (nM) |
|---|---|---|---|---|---|
| 154 | (structure) | 6.1 | 22 | 7.9 | 14 |

[a]ND, not determined.

Thus, 4-(3-methoxyanilino)-2-(2-pyridinyl)-6-(trifluoromethyl)pyrimidine (Compound A) and related compounds are identified as potent caspase cascade activators and inducer of apoptosis in solid tumor cells.

EXAMPLE 222

Identification of 4-(3-Methoxyanilino)-2-(2-pyridinyl)-6-(trifluoromethyl)pyrimidine as Antineoplastic Compound that Inhibits Cell Proliferation ($GI_{50}$)

T-47D cells were grown and harvested as in Example 221. An aliquot of 90 µl of cells ($2.2 \times 10^4$ cells/ml) was added to a well of a 96-well microtiter plate containing 10 µl of a 10% DMSO in RPMI-1640 media solution containing 1 nM to 100 µM of 4-(3-methoxyanilino)-2-(2-pyridinyl)-6-(trifluoromethyl)pyrimidine (0.1 nM to 10 µM final). An aliquot of 90 µl of cells was added to a well of a 96-well microtiter plate containing 10 µl of a 10% DMSO in RPMI-1640 media solution without compound as the control sample for maximal cell proliferation ($A_{Max}$). The samples were mixed by agitation and then incubated at 37° C. for 48 h in a 5% $CO_2$-95% humidity incubator. After incubation, the samples were removed from the incubator and 20 µl of CellTiter 96 $AQ_{UEOUS}$ One Solution Cell Proliferation™ reagent (Promega) was added. The samples were mixed by agitation and incubated at 37° C. for 2–4 h in a 5% $CO_2$-95% humidity incubator. Using an absorbance plate reader (Model 1420 Wallac Instruments), an initial reading (T=0) was made approximately 1–2 min after addition of the solution, employing absorbance at 490 nm. This determines the possible background absorbance of the test compounds. No absorbance for 4-(3-methoxyanilino)-2-(2-pyridinyl)-6-(trifluoromethyl)pyrimidine was found at 490 nm. After the 2–4 h incubation, the samples were read for absorbance as above ($A_{Test}$).

Baseline for $GI_{50}$ (dose for 50% inhibition of cell proliferation) of initial cell numbers were determined by adding an aliquot of 90 µl of cells or 90 µl of media, respectively, to wells of a 96-well microtiter plate containing 10 µl of a 10% DMSO in RPMI-1640 media solution. The samples were mixed by agitation and then incubated at 37° C. for 0.5 h in a 5% $CO_2$-95% humidity incubator. After incubation, the samples were removed from the incubator and 20 µl of CellTiter 96 $AQ_{UEOUS}$ One Solution Cell Proliferation™ reagent (Promega) was added. The samples were mixed by agitation and incubated at 37° C. for 2–4 h in a 5% $CO_2$-95% humidity incubator. Absorbance was read as above, ($A_{Start}$) defining absorbance for initial cell number used as baseline in $GI_{50}$ determinations.

Calculation:

$GI_{50}$ (dose for 50% inhibition of cell proliferation) is the concentration where $[(A_{Test}-A_{Start})/(A_{Max}-A_{Start})]=0.5$ The $GI_{50}$ (nM) are summarized in Table II

TABLE II

| | $GI_{50}$ in T-47D Cancer Cells | |
|---|---|---|
| Cell lines | | Compound A GI50 (nM) |
| T-47D | | 30 |

Thus, 4-(3-methoxyanilino)-2-(2-pyridinyl)-6-(trifluoromethyl)pyrimidine (Compound A) is identified as antineoplastic compound that inhibits cell proliferation.

EXAMPLE 223

Identification of 4-(3-methoxyanilino)-2-(2-pyridinyl)-6-(trifluoromethyl)pyrimidine as Antineoplastic Compound that Selectively Inhibits the Proliferation of Breast Cancer Cells ($G_{I50}$)

T-47D, ZR-75-1, MX-1, SK-Br-3, MCF-7, MDA-MB-435 (all breast cancer cell lines), Panc-1 (pancreatic cancer cell line), MES-SA (sarcoma cell line), and PC-3 (prostate cancer cell line) cells were grown according to the conditions recommended by American Type Culture Collection. SW620 (colorectal cancer cell line), and P388 (mouse leukemia cell line) were grown according to the conditions provided by the National Cancer Institute. The cell proliferation assay and the calculations of $GI_{50}$S were performed as in Example 222 and the results were summarized in Tables III and IV.

TABLE III

GI50 in human breast cancer cell lines.

| | Cell Line | | | | |
|---|---|---|---|---|---|
| | T47D | ZR 75-1 | MCF-7 | MDA-MB-435 | SK—Br-3 |
| $GI_{50}$(nM) | 30 | 100 | 100 | 4500 | 60 |

TABLE IV

GI50 in non-breast cancer cell lines.

| | Cell Line | | | | |
|---|---|---|---|---|---|
| | PC-3 | Panc-1 | SW620 | P388 | MES-SA |
| $GI_{50}$(nM) | >10,000 | >10,000 | >10,000 | >10,000 | >10,000 |

Thus, 4-(3-methoxyanilino)-2-(2-pyridinyl)-6-(trifluoromethyl)pyrimidine was identified as antineoplastic compound that selectively inhibits the growth of human breast cancer cells.

EXAMPLE 224

Treatment with 4-(3-methoxyanilino)-2-(2-pyridinyl)-6-(trifluoromethyl)pyrimidine Leads to Cell Cycle Arrest and Apoptosis in T-47D Cells T-47D, a breast cancer cell line, was maintained and harvested as described in Example 221. $5 \times 10^5$ Cells were treated with 0.2 µM of 4-(3-methoxyanilino)-2-(2-pyridinyl)-6-(trifluoromethyl)pyrimidine for 48 h at 37° C. As a control, cells were also incubated with equivalent amount of solvent (DMSO). Cells were harvested at 1,200 rpm and then transferred to 12×75 mm polystyrene tubes. Cells were then resuspended in 500 µl of 1% Na Citrate, 0.1% Triton X-100, and 50 µg/ml of propidium iodide and incubated at room temperature for 30 min followed by flow cytometer analysis. All flow cytometry analyses were performed on FACScalibur (Becton Dickinson) using Cell Quest analysis software. The x-axis plotted the amount of fluorescence and the y-axis is plotted the number of cells with the indicated fluorescence. The T-47D control cell population profile is seen in FIG. 1A and the increase in G2/M DNA content cells that is seen when treated with 4-(3-methoxyanilino)-2-(2-pyridinyl)-6-(trifluoromethyl)pyrimidine at 0.2 µM is seen in FIG. 1B. An increase in the sub-diploid DNA content of cells (FIG. 1) is also seen to increase from 2% to 25% with compound treatment. The sub-diploid amount of DNA is indicative of apoptotic cells which have undergone DNA degradation or fragmentation.

EXAMPLE 225

4-(3-Methoxyanilino)-2-(2-pyridinyl)-6-(trifluoromethyl)pyrimidine Inhibit the Clonogenic Survival of T47D and MX-1, Solid Tumor Cell Lines T47D and MX-1 cells were grown according to the conditions according conditions recommended by American Type Culture Collection. In a well of a 96 well plate, 30,000 cells were seeded and treated with tested compound at the indicated concentrations for 48 hr in a 5% $CO_2$-95% humidity incubator at 37° C. Control wells were treated with the same amount of solvent (DMSO) as the compound samples. After the 48 h treatment, the supernatant was removed to a sterile culture tube and the wells washed with phosphate buffered saline, and the adherent cells trypsinized for 5 min. The trypsinzed cells were added to the culture supernatant, cells were collected (1,200 rpm, 10 min), washed with phosphate buffered saline, and resuspended in fresh media. The cells were counted for trypan blue negative cells, and the cells diluted with fresh media to 1,000 cells/ml. To a well of a 24-well plate, 0.1 ml of the cell suspension was added along with 1 ml of fresh media (cell suspensions were passed through a 22G needle several times just before plating to form single cell suspensions). Plates are incubated in a 5% $CO_2$-95% humidity incubator at 37° C. for 7–10 days. Colonies are counted when the sizes reached greater than 50 cells per colony. Cells are washed with phosphate buffered saline, fixed with 100% methanol for 15 min, and then stained with 0.5% gentian violet for 15 min. Colonies are rinsed with water and the colonies counted and the fraction surviving expressed as the percentage of the number of control colonies.

The results showed that a 48 hr treatment with 4-(3-methoxyanilino)-2-(2-pyridinyl)-6-(trifluoromethyl)pyrimidine inhibited the ability of T47D and MX-1 cells to proliferate and their colony forming ability with an $IC_{50}$ of about 100 and 300 nM, respectively.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A method of treating breast cancer, lung cancer or colon cancer, comprising administering to an animal in need of such treatment an effective amount of a compound of Formula I:

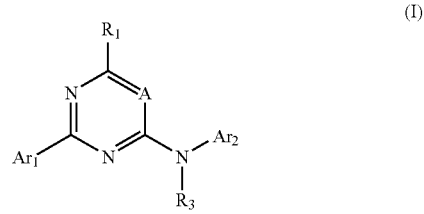

(I)

or a pharmaceutically acceptable salt or prodrug thereof, wherein:

$Ar_1$ is optionally substituted pyridinyl, pyridinyl N-oxide, pyrazinyl, pyrimidinyl or phenyl and $Ar_2$ is optionally substituted pyridinyl, indolyl or:

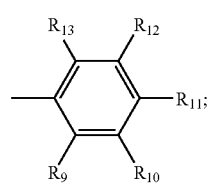

A is C—$R_2$;

R₁ and R₂ are independently hydrogen, halo, haloalkyl, aryl, fused aryl, carbocyclic, morpholinyl, pyridinyl, alkyl, alkenyl, alkynyl, arylalkyl, arylalkenyl, arylalkynyl, carbocycloalkyl, nitro, amino, cyano, acylamido, hydroxy, thiol, acyloxy, azido, alkoxy, alkoxyalkyl, aryloxy, arylalkoxy, haloalkoxy, carbonylamido or alkylthiol;

R₃ is hydrogen, optionally substituted alkyl or optionally substituted cycloalkyl; and R₉–R₁₃ are independently hydrogen, halo, haloalkyl, aryl, fused aryl, carbocyclic, alkyl, alkenyl, alkynyl, arylalkyl, arylalkenyl, arylalkynyl, carbocycloalkyl, hydroxyalkyl, nitro, amino, cyano, acylamido, hydroxy, thiol, acyloxy, azido, alkoxy, aryloxy, arylalkoxy, haloalkoxy, carboxy, carbonylamido or alkylthiol.

2. The method of claim 1, wherein said animal is a mammal.

3. The method of claim 1, wherein R₃ is hydrogen.

4. The method of claim 1, wherein said compound has the Formula II:

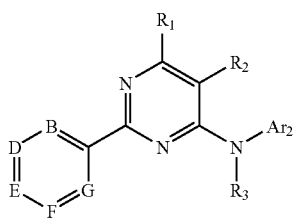

(II)

or a pharmaceutically acceptable salt or prodrug thereof, wherein R₁–R₃, and Ar₂ are as defined in claim 1;

B is N or C—R₄;
D is N or C—R₅;
E is N or C—R₆;
F is N or C—R₇;
G is N or C—R₈; and R₄–R₈ are independently hydrogen, halo, haloalkyl, aryl, fused aryl, carbocyclic, C₁₋₁₀ alkyl, alkenyl, alkynyl, arylalkyl, arylalkenyl, arylalkynyl, carbocycloalkyl, hydroxyalkyl, nitro, amino, cyano, acylamido, hydroxy, thiol, acyloxy, azido, alkoxy, aryloxy, arylalkoxy, haloalkoxy, carboxy, carbonylamido or alkylthiol;

provided that not more than two of B, D, E, F or G are N.

5. The method of claim 4, wherein R₁ is optionally substituted alkyl or haloalkyl.

6. The method of claim 4, wherein Ar₂ is:

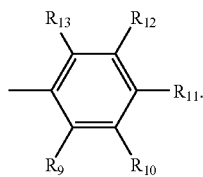

7. The method of claim 4, wherein B is N.

8. The method of claim 1, wherein said compound is selected from the group consisting of:

4-(3-Methoxyanilino)-2-(2-pyridinyl)-6-(trifluoromethyl)pyrimidine;
4-(2-Fluoroanilino)-2-(4-pyridinyl)-6-(trifluoromethyl)pyrimidine;
4-(4-Methoxyanilino)-2-(4-pyridinyl)-6-(trifluoromethyl)pyrimidine;
4-(4-Methoxyanilino)-2-(2-pyridinyl)-6-(trifluoromethyl)pyrimidine;
4-(3,5-Dichloroanilino)-2-(4-pyridinyl)-6-(trifluoromethyl)pyrimidine;
4-(2,4-Difluoroanilino)-2-(4-pyridinyl)-6-(trifluoromethyl)pyrimidine;
4-(2-Methylanilino)-2-phenyl-6-methylpyrimidine;
4-(4-Methoxyanilino)-2-(2-hydroxyphenyl)-6-methylpyrimidine;
4-(4-(Trifluoromethoxy)anilino)-2-(pyridinyl)-6-(trifluoromethyl)pyrimidine;
4-(3-Fluoroanilino)-2-(2-pyridinyl)-6-(trifluoromethyl)pyrimidine;
4-(3,5-Dichloroanilino)-2-(2-pyridinyl)-6-(trifluoromethyl)pyrimidine;
4-(2-Fluoroanilino)-2-(2-pyridinyl)-6-(trifluoromethyl)pyrimidine;
4-(3-(Trifluoromethyl)anilino)-2-(2-pyridinyl)-6-(trifluoromethyl)pyrimidine;
4-(4-(Trifluoromethyl)anilino)-2-(2-pyridinyl)-6-(trifluoromethyl)pyrimidine;
4-(4-Fluoroanilino)-2-(2-pyridinyl)-6-(trifluoromethyl)pyrimidine;
4-(2,4-Dichloroanilino)-2-(2-pyridinyl)-6-(trifluoromethyl)pyrimidine;
4-(3-Chloroanilino)-2-(2-pyridinyl)-6-(trifluoromethyl)pyrimidine;
4-(3,4-Dichloroanilino)-2-(2-pyridinyl)-6-(trifluoromethyl)pyrimidine;
4-(4-Chloroanilino)-2-(2-pyridinyl)-6-(trifluoromethyl)pyrimidine;
4-(4-Fluoroanilino)-2-(3-pyridinyl)-6-(trifluoromethyl)pyrimidine;
4-(4-Methoxyanilino)-2-(3-pyridinyl)-6-(trifluoromethyl)pyrimidine;
4-(2-Fluoroanilino)-2-(3-pyridinyl)-6-(trifluoromethyl)pyrimidine;
4-(3-(Trifluoromethyl)anilino)-2-(3-pyridinyl)-6-(trifluoromethyl)pyrimidine;
4-(3-Chloroanilino)-2-(3-pyridinyl)-6-(trifluoromethyl)pyrimidine;
4-(4-Chloroanilino)-2-(2-pyridinyl)-6-(methoxymethyl)pyrimidine;
4-(4-Methoxyanilino)-2-(2-pyridinyl)-6-(methoxymethyl)pyrimidine;
4-(3-Chloroanilino)-2-(2-pyridinyl)-6-(methoxymethyl)pyrimidine;
4-(4-(Trifluoromethoxy)anilino)-2-(2-pyridinyl)-6-t-butylpyrimidine;
4-(4-Methoxyanilino)-2-(2-pyridinyl)-6-t-butylpyrimidine;
4-(3-Methoxyanilino)-2-phenyl-6-chloropyrimidine;
4-(3-Methoxyanilino)-6-methyl-2-(2-pyridinyl)pyrimidine;
4-(3-Fluoroanilino)-6-methyl-2-(2-pyridinyl)pyrimidine;
4-(3-Methylanilino)-6-methyl-2-(2-pyridinyl)pyrimidine;
4-(4-Methoxyanilino)-2-(3-methylphenyl)-6-(methoxymethyl)pyrimidine;
4-(2,5-Dimethoxyanilino)-6-methyl-2-(2-pyridinyl)pyrimidine;
4-(3-Dimethylaminoanilino)-6-methyl-2-(2-pyridinyl)pyrimidine;

4-(3-Isopropylanilino)-6-methyl-2-(2-pyridinyl)pyrimidine;
4-(2,5-Dimethoxyanilino)-2-(3-pyridinyl)-6-(trifluoromethyl)pyrimidine;
4-(2,5-Dimethoxyanilino)-6-(methoxymethyl)-2-(3-methylphenyl)pyrimidine;
4-(3-Methoxyanilino)-2-(4-pyridinyl)-6-(trifluoromethyl)pyrimidine;
4-(2,5-Dimethoxyanilino)-2-(4-pyridinyl)-6-(trifluoromethyl)pyrimidine;
4-(2-Chloro-5-methoxyanilino)-2-(3-pyridinyl)-6-(trifluoromethyl)pyrimidine;
4-(5-Methoxy-2-methylanilino)-2-(3-pyridinyl)-6-(trifluoromethyl)pyrimidine;
4-(2-Chloro-5-methoxyanilino)-6-methyl-2-(2-pyridinyl)pyrimidine;
4-(5-Methoxy-2-methylanilino)-6-methyl-2-(2-pyridinyl)pyrimidine;
4-(2-Chloro-5-methoxyanilino)-2-(4-pyridinyl)-6-(trifluoromethyl)pyrimidine;
4-(5-Methoxy-2-methylanilino)-2-(4-pyridinyl)-6-(trifluoromethyl)pyrimidine;
4-(2-Chloro-5-methoxyanilino)-6-(methoxymethyl)-2-(3-methylphenyl)pyrimidine;
4-(5-Methoxy-2-methylanilino)-6-(methoxymethyl)-2-(3-methylphenyl)pyrimidine;
4-(2,5-Dimethoxyanilino)-2-(2-pyridinyl)-6-(trifluoromethyl)pyrimidine;
4-(2,5-Dimethylanilino)-2-(3-pyridinyl)-6-(trifluoromethyl)pyrimidine;
4-(3-Hydroxyanilino)-2-(2-pyridinyl)-6-(trifluoromethyl)pyrimidine hydrochloride;
4-(3-Methoxyanilino)-2-phenyl-6-(trifluoromethyl)pyrimidine;
4-(2,5-Dimethoxyanilino)-2-phenyl-6-(trifluoromethyl)pyrimidine;
4-(3,4-Dimethoxyanilino)-2-phenyl-6-(trifluoromethyl)pyrimidine;
4-(5-Methoxy-2-methylanilino)-2-phenyl-6-(trifluoromethyl)pyrimidine;
4-(2-Chloro-5-methoxyanilino)-2-phenyl-6-(trifluoromethyl)pyrimidine;
4-(2-Methoxy-5-phenoxyanilino)-2-(3-pyridinyl)-6-(trifluoromethyl)pyrimidine;
4-(2-Methoxy-5-methylanilino)-2-(3-pyridinyl)-6-(trifluoromethyl)pyrimidine;
4-(5-Fluoro-2-methylanilino)-2-(3-pyridinyl)-6-(trifluoromethyl)pyrimidine;
4-(2-Methoxy-5-trifluoromethylanilino)-2-(3-pyridinyl)-6-(trifluoromethyl)pyrimidine;
4-(2-Methyl-5-nitroanilino)-2-(3-pyridinyl)-6-(trifluoromethyl)pyrimidine;
4-(5-Amino-2-methylanilino)-2-(3-pyridinyl)-6-(trifluoromethyl)pyrimidine hydrochloride;
4-(3-Ethoxyanilino)-2-(2-pyridinyl)-6-(trifluoromethyl)pyrimidine;
4-(3-Ethylanilino)-2-(2-pyridinyl)-6-(trifluoromethyl)pyrimidine;
4-(5-Methoxy-2-methylanilino)-2-(2-pyridinyl)-6-(trifluoromethyl)pyrimidine;
4-(2-Chloro-5-methoxyanilino)-2-(2-pyridinyl)-6-(trifluoromethyl)pyrimidine;
4-(3-Methylmercaptoanilino)-2-(2-pyridinyl)-6-(trifluoromethyl)pyrimidine;
4-(3-Hydroxyanilino)-2-(3-pyridinyl)-6-(trifluoromethyl)pyrimidine hydrochloride;
4-(3-Hydroxyanilino)-2-(4-pyridinyl)-6-(trifluoromethyl)pyrimidine hydrochloride;
4-(2,4-Dimethoxyanilino)-6-methyl-2-(2-pyridinyl)-pyrimidine hydrochloride;
4-(3,5-Dimethoxyanilino)-6-methyl-2-(2-pyridinyl)-pyrimidine hydrochloride;
4-(2,5-Diethoxyanilino)-2-(3-pyridinyl)-6-(trifluoromethyl)pyrimidine;
4-(5-Carboxyl-2-methoxyanilino)-2-(3-pyridinyl)-6-(trifluoromethyl)pyrimidine hydrochloride;
4-(2-Chloro-5-hydroxyanilino)-2-(3-pyridinyl)-6-(trifluoromethyl)pyrimidine;
4-(2-Chloro-5-hydroxyanilino)-2-(4-pyridinyl)-6-(trifluoromethyl)pyrimidine;
4-(2,6-Dimethylanilino)-6-methyl-2-(2-pyridinyl)pyrimidine;
4-(2,5-Dimethylanilino)-2-(4-pyridinyl)-6-(trifluoromethyl)pyrimidine hydrochloride;
4-(2-Methoxy-5-methylanilino)-2-(4-pyridinyl)-6-(trifluoromethyl)pyrimidine;
4-(5-Hydroxy-2-methylanilino)-2-(3-pyridinyl)-6-(trifluoromethyl)pyrimidine;
4-(5-Hydroxy-2-methylanilino)-2-(4-pyridinyl)-6-(trifluoromethyl)pyrimidine;
4-(2-Cyano-5-methylanilino)-2-(3-pyridinyl)-6-(trifluoromethyl)pyrimidine;
4-(3,5-Dimethylanilino)-2-(3-pyridinyl)-6-(trifluoromethyl)pyrimidine;
4-(3,5-Dimethoxyanhlino)-2-(3-pyridinyl)-6-(trifluoromethyl)pyrimidine hydrochloride;
4-(2-Chloro-5-methylanilino)-2-(3-pyridinyl)-6-(trifluoromethyl)pyrimidine;
4-(3-Methoxy-5-trifluoromethylanilino)-2-(3-pyridinyl)-6-(trifluoromethyl)pyrimidine;
4-(2-Chloro-5-methoxyanilino)-2-[6-(trifluoromethyl)-3-pyridinyl]-6-(trifluoromethyl)pyrimidine;
4-(5-Bromo-2-methoxyanilino)-2-(3-pyridinyl)-6-(trifluoromethyl)pyrimidine;
4-(2-Bromo-5-methoxyanilino)-2-(3-pyridinyl)-6-(trifluoromethyl)pyrimidine;
4-[3-Methyl-5-(trifluoromethyl)anilino]-2-(3-pyridinyl)-6-(trifluoromethyl)pyrimidine;
4-(5-Chloro-2-hydroxyanilino)-2-(3-pyridinyl)-6-(trifluoromethyl)pyrimidine;
4-(4-Chloro-2,5-dimethoxyanilino)-2-(3-pyridinyl)-6-(trifluoromethyl)pyrimidine hydrochloride;
4-(2,4-Dichloro-5-methoxyanilino)-2-(3-pyridinyl)-6-(trifluoromethyl)pyrimidine;
4-(2-Acetyl-4,5-dimethoxyanilino)-2-(3-pyridinyl)-6-(trifluoromethyl)pyrimidine;
4-(2-Methyl-5-nitroanilino)-2-(4-pyridinyl)-6-(trifluoromethyl)pyrimidine;
4-(5-Amino-2-methylanilino)-2-(4-pyridinyl)-6-(trifluoromethyl)pyrimidine;
N-[4-Methyl-3-(2-pyridin-3-yl-6-(trifluoromethyl)pyrimidin-4-ylamino)-phenyl]benzamide;
4-Methyl-N-[4-methyl-3-(2-pyridin-4-yl-6-(trifluoromethyl)pyrimidin-4-ylamino)-phenyl]benzamide;
N-[4-Methyl-3-(2-pyridin-4-yl-6-(trifluoromethyl)pyrimidin-4-ylamino)-phenyl]nicotinamide;
6-Chloro-N-[4-methyl-3-(2-pyridin-4-yl-6-(trifluoromethyl)pyrimidin-4-ylamino)-phenyl]nicotinamide;

N-[4-Methyl-3-(2-pyridin-4-yl-6-(trifluoromethyl)pyrimidin-4-ylamino)-phenyl]-4-morpholino-benzamide;
4-Chloro-N-[4-methyl-3-(2-pyridin-4-yl-6-(trifluoromethyl)pyrimidin-4-ylamino)-phenyl]benzamide;
4-Methoxy-N-[4-methyl-3-(2-pyridin-4-yl-6-(trifluoromethyl)pyrimidin-4-ylamino)-phenyl]benzamide;
4-Chloromethyl-N-[4-methyl-3-(2-pyridin-4-yl-6-(trifluoromethyl)pyrimidin-4-ylamino)-phenyl]benzamide;
4-(4-Methyl-piperazin-1-ylmethyl)-N-[4-methyl-3-(2-pyridin-4-yl-6-(trifluoromethyl)pyrimidin-4-ylamino)-phenyl]benzamide;
4-(2,5-Dimethyl-4-hydroxyanilino)-2-(2-pyridinyl)-6-(trifluoromethyl)pyrimidine hydrochloride;
4-(2,5-Dimethyl-4-hydroxyanilino)-2-(4-pyridinyl)-6-(trifluoromethyl)pyrimidine;
4-(4-Chloro-2,5-dimethoxyanilino)-2-(2-pyridinyl)-6-(trifluoromethyl)pyrimidine hydrochloride;
4-(4,5-Dimethoxy-2-methylanilino)-2-(2-pyridinyl)-6-(trifluoromethyl)pyrimidine hydrochloride;
4-(4,5-Dimethoxy-2-methylanilino)-2-(4-pyridinyl)-6-(trifluoromethyl)pyrimidine hydrochloride;
4-(3-Trifluoromethoxyanilino)-2-(2-pyridinyl)-6-(trifluoromethyl)pyrimidine hydrochloride;
4-(4,5-Dimethoxy-2-methylanilino)-2-(3-pyridinyl)-6-(trifluoromethyl)pyrimidine;
4-(4-Chloro-2,5-dimethoxyanilino)-2-(4-pyridinyl)-6-(trifluoromethyl)pyrimidine hydrochloride;
4-(2-Hydroxy-5-methylanilino)-2-(3-pyridinyl)-6-(trifluoromethyl)pyrimidine;
4-(3,5-Dimethoxyanilino)-2-(4-pyridinyl)-6-trifluoromethyl-pyrimidine;
4-(5-Chloro-2-methoxyanilino)-2-(4-pyridinyl)-6-trifluoromethyl-pyrimidine;
6-Methyl-4-(3-phenoxyanilino)-2-(2-pyridinyl)pyrimidine;
4-(3-Chloroanilino)-6-methyl-2-(2-pyridinyl)pyrimidine;
4-(3,4-Dimethoxyanilino)-6-methyl-2-(2-pyridinyl)pyrimidine;
4-(4-Fluoro-3-methoxyanilino)-6-methyl-2-(2-pyridinyl)pyrimidine;
4-(3-Isopropoxyanilino)-6-methyl-2-(2-pyridinyl)pyrimidine;
4-(3,4-Dimethoxyanilino)-6-trifluoromethyl-2-(2-pyridinyl)pyrimidine;
4-(5-Chloro-2-methoxyanilino)-2-(3-pyridinyl)-6-trifluoromethylpyrimidine;
4-(5-Hydroxy-2-methylanilino)-2-(2-pyridinyl)-6-trifluoromethylpyrimidine;
4-(2-Chloro-5-hydroxyanilino)-2-(2-pyridinyl)-6-trifluormethylpyrimidine;
4-(2-Methoxy-5-methylanilino)-2-(2-pyridinyl)-6-trifluoromethylpyrimidine;
4-(2-Hydroxy-5-isopropylanilino)-2-(2-pyridinyl)-6-trifluoromethylpyrimidine;
4-(3,5-Dimethoxyanilino)-2-(2-pyridinyl)-6-trifluoromethylpyrimidine;
4-(2,5-Dimethyl-4-hydroxyanilino)-2-(3-pyridinyl)-6-trifluoromethylpyrimidine;
4-(2-Cyano-4,5-dimethoxyanilino)-2-(3-pyridinyl)-6-trifluoromethylpyrimidine;
4-(2-Chloro-5-methoxyanilino)-2-(3-pyridinyl)-6-(t-butyl)pyrimidine;
4-(4-Chloro-2-methoxy-5-methylanilino)-2-(3-pyridinyl)-6-(trifluoromethyl)pyrimidine;
4-(2,4,5-Trimethylanilino)-2-(3-pyridinyl)-6-(trifluoromethyl)pyrimidine; and
4-(2,4-Dichloro-5-hydroxyanilino)-2-(3-pyridinyl)-6-(trifluoromethyl)pyrimidine.

9. The method of claim 1, wherein said compound is selected from the group consisting of:
4-(3-Methoxyanilino)-2,6-di(2-pyridinyl)pyrimidine;
4-(2,5-Dimethoxyanilino)-2,6-di(2-pyridinyl)pyrimidine;
4-(5-Methoxy-2-methylanilino)-2,6-di(2-pyridinyl)pyrimidine;
4-(2-Methoxy-5-methylanilino)-2,6-di(2-pyridinyl)pyrimidine;
4-(2-Chloro-5-methoxyanilino)-2,6-di(2-pyridinyl)pyrimidine;
4-(2,5-Dimethylanilino)-2,6-di(2-pyridinyl)pyrimidine;
4-(Indol-4-ylamino)-2-(3-pyridinyl)-6-(trifluoromethyl)pyrimidine;
4-(Indol-5-ylamino)-2-(3-pyridinyl)-6-trifluoromethylpyrimidine;
4-(2,6-Dimethoxypyridin-3-ylamino)-2-(3-pyridinyl)-6-trifluoromethylpyrimidine;
4-(2-Methoxy-pyridin-5-ylamino)-2-(3-pyridinyl)-6-trifluoromethylpyrimidine;
4-(Indol-4-ylamino)-2-(2-pyridinyl)-6-trifluoromethylpyrimidine;
4-(2-Methyl-indol-5-ylamino)-2-(3-pyridinyl)-6-trifluoromethylpyrimidine;
4-(3-Methoxyanilino)-2-(2-pyrazinyl)-6-(trifluoromethyl)pyrimidine;
4-(2,5-Dimethoxyanilino)-2-(2-pyrazinyl)-6-(trifluoromethyl)pyrimidine;
4-(3,4-Dimethoxyanilino)-2-(2-pyrazinyl)-6-(trifluoromethyl)pyrimidine;
4-(5-Methoxy-2-methylanilino)-2-(2-pyrazinyl)-6-(trifluoromethyl)pyrimidine;
4-(2-Chloro-5-methoxyanilino)-2-(2-pyrazinyl)-6-(trifluoromethyl)pyrimidine;
4-(3-Hydroxyanilino)-2-(2-pyrazinyl)-6-(trifluoromethyl)pyrimidine hydrochloride;
4-(2,5-Dimethyl-4-hydroxyanilino)-(2-pyrazinyl)-6-(trifluoromethyl)pyrimidine hydrochloride;
4-(4-Chloro-2,5-dimethoxyanilino)-(2-pyrazinyl)-6-(trifluoromethyl)pyrimidine hydrochloride;
4-(4,5-Dimethoxy-2-methylanilino)-2-(2-pyrazinyl)-6-(trifluoromethyl)pyrimidine hydrochloride;
4-(2-Methoxy-5-nitroanilino)-2-(2-pyrazinyl)-6-trifluoromethylpyrimidine;
4-(5-Methoxy-2-nitroanilino)-2-(2-pyrazinyl)-6-trifluoromethylpyrimidine;
4-(3,5-Dimethoxyanilino)-2-(2-pyrazinyl)-6-trifluoromethylpyrimidine;
4-(5-Carboxy-2-methoxyanilino)-2-(2-pyrazinyl)-6-trifluoromethylpyrimidine;
4-(2-Methoxy-5-methylanilino)-2-(2-pyrazinyl)-6-trifluoromethylpyrimidine;
4-(5-Hydroxy-2-methylanilino)-2-(2-pyrazinyl)-6-trifluoromethylpyrimidine;
4-(2-Chloro-5-hydroxyanilino)-2-(2-pyrazinyl)-6-trifluoromethylpyrimidine;
4-(2,5-Dimethylanilino)-2-(2-pyrazinyl)-6-trifluoromethylpyrimidine;
4-(5-Chloro-2-methoxyanilino)-2-(2-pyrazinyl)-6-trifluoromethylpyrimidine;
4-(5-Chloro-2-hydroxyanilino)-2-(2-pyrazinyl)-6-trifluoromethylpyrimidine;
4-(5-Hydroxy-2-isopropylanilino)-2-(2-pyrazinyl)-6-trifluoromethypyrimidine;
4-(2-Chloro-5-methoxyanilino)-2-(4-pyridinyl-N-oxide)-6-(trifluoromethyl)pyrimidine; and 4-(2-Chloro-5-methoxy-anilino)-2-(2-pyrimidinyl)-6-trifluoromethylpyrimidine hydrochloride.

10. The method of claim 1, wherein said animal is a mammal.

11. A method for the treatment of drug resistant breast cancer, lung cancer or colon cancer, comprising administering to an animal in need of such treatment an effective amount of a compound of the Formula I:

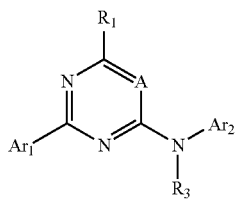

(I)

or a pharmaceutically acceptable salt or prodrug thereof, wherein:

$Ar_1$ is optionally substituted pyridinyl, pyridinyl N-oxide, pyrazinyl, pyrimidinyl or phenyl and $Ar_2$ is optionally substituted pyridinyl, indolyl or:

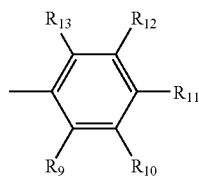

A is —C—$R_2$;

$R_1$ and $R_2$ are independently hydrogen, halo, haloalkyl, aryl, fused aryl, carbocyclic, morpholinyl pyridinyl $C_{1-10}$ alkyl, alkenyl, alkynyl, arylalkyl, arylalkenyl, arylalkynyl, carbocycloalkyl, nitro, amino, cyano, acylamido, hydroxy, thiol, acyloxy, azido, alkoxy, alkoxyalkyl, aryloxy, arylalkoxy, haloalkoxy, carbonylamido or alkylthiol;

$R_3$ is hydrogen, optionally substituted alkyl or optionally substituted cycloalkyl; and $R_9$–$R_{13}$ are independently hydrogen, halo, haloalkyl, aryl, fused aryl, carbocyclic, alkyl, alkenyl, alkynyl, arylalkyl, arylalkenyl, arylalkynyl, carbocycloalkyl, hydroxyalkyl, nitro, amino, cyano, acylamido, hydroxy, thiol, acyloxy, azido, alkoxy, aryloxy, arylalkoxy, haloalkoxy, carboxy, carbonylamido or alkylthiol.

12. The method of claim 11, wherein said animal is a mammal.

13. The method of claim 1 or 11, additionally comprising administering at least one known cancer chemotherapeutic agent, or a pharmaceutically acceptable salt of said agent.

14. The method of claim 13, wherein said known cancer therapeutic agent is selected from the group consisting of busulfan, cis-platin, mitomycin C, carboplatin, colchicine, vinblastine, paclitaxel, docetaxel, camptothecin, topotecan, doxorubicin, etoposide, 5-azacytidine, 5-fluorouracil, methotrexate, 5-fluoro-2'-deoxy-uridine, ara-C, hydroxyurea, thioguanine, melphalan, chlorambucil, cyclophosphamide, ifosfamide, vincristine, mitoguazone, epirubicin, aclarubicin, bleomycin, mitoxantrone, elliptinium, fludarabine, octreotide, retinoic acid, tamoxifen, Herceptin®, Rituxan® and alanosine.

15. The method of claim 1 or 11, additionally comprising treating said animal with radiation-therapy.

16. The method of claim 1 or 11, wherein said compound is administered after surgical treatment of said animal for cancer.

17. A method of treating breast cancer, lung cancer or colon cancer, comprising administering to an animal in need of such treatment an effective amount of a compound selected from the group consisting of:

4-(3-Methoxyanilino)-6-(methoxymethyl)-2-(2-methyl-1-3-thiazol-4-yl)pyrimidine;

4-(2,5-Dimethoxyanilino)-6-(methoxymethyl)-2-(2-methyl-1-3-thiazol-4-yl)pyrimidine;

4-(2-Chloro-5-methoxyanilino)-6-(methoxymethyl)-2-(2-methyl-1,3-thiazol-4-yl)pyrimidine;

4-(5-Methoxy-2-methylanilino)-6-(methoxymethyl)-2-(2-methyl-1,3-thiazol-4-yl)pyrimidine;

4-(3,4-Methylenedioxyanilino)-2-(2-pyridinyl)-6-(trifluoromethyl)pyrimidine;

4-(3,4-Methylenedioxyanilino)-2-(4-pyridinyl)-6-(trifluoromethyl)pyrimidine;

4-(3,4-Methylenedioxyanilino)-2-(3-pyridinyl)-6-(trifluoromethyl)pyrimidine;

4-[2-Methyl-5-(carboxymethylester)anilino]-2-(3-pyridinyl)-6-(trifluoromethyl)pyrimidine;

4-(3,4-Methylenedioxyanilino)-2-(2-pyrazinyl)-6-(trifluoromethyl)pyrimidine; and 4-(3-Methoxyanilino)-2-(2-piperidinyl)-6-(trifluoromethyl)pyrimidine.

18. The method of claim 1, wherein said cancer is lung carcinoma.

19. The method of claim 1, wherein said cancer is colon carcinoma.

20. The method of claim 1, wherein said cancer is breast carcinoma.

* * * * *